(12) United States Patent
Shalon

(10) Patent No.: US 11,766,249 B2
(45) Date of Patent: Sep. 26, 2023

(54) DEVICES AND METHODS FOR COLLECTING GASTROINTESTINAL SAMPLES

(71) Applicant: ENVIVO BIO INC, San Carlos, CA (US)

(72) Inventor: Tidhar Dari Shalon, Los Altos Hills, CA (US)

(73) Assignee: ENVIVO BIO INC., San Carlos, CA (US)

( * ) Notice: Subject to any disclaimer, the term of this patent is extended or adjusted under 35 U.S.C. 154(b) by 659 days.

(21) Appl. No.: 16/611,477

(22) PCT Filed: May 18, 2018

(86) PCT No.: PCT/US2018/033434
§ 371 (c)(1),
(2) Date: Nov. 7, 2019

(87) PCT Pub. No.: WO2018/213729
PCT Pub. Date: Nov. 22, 2018

(65) Prior Publication Data
US 2020/0138416 A1    May 7, 2020

Related U.S. Application Data

(60) Provisional application No. 62/509,014, filed on May 19, 2017, provisional application No. 62/510,247, filed on May 23, 2017, provisional application No. 62/512,719, filed on May 30, 2017, provisional application No. 62/517,841, filed on Jun. 9, 2017, provisional application No. 62/522,078, filed on Jun.
(Continued)

(51) Int. Cl.
*A61B 10/00* (2006.01)
*A61B 10/04* (2006.01)

(52) U.S. Cl.
CPC .......... *A61B 10/0045* (2013.01); *A61B 10/04* (2013.01); *A61B 2010/0061* (2013.01)

(58) Field of Classification Search
CPC ............... A61B 10/0045; A61B 10/04; A61B 2010/0061
See application file for complete search history.

(56) References Cited

U.S. PATENT DOCUMENTS 2,508,690 A * 5/1950 Schmerl ................ A61M 25/01
206/438
2,907,326 A * 10/1959 Gerarde ................ A61M 5/282
600/578

(Continued)

FOREIGN PATENT DOCUMENTS

| CN | 105050500 A | 11/2015 |
|---|---|---|
| JP | 5376584 A | 7/1978 |

(Continued)

OTHER PUBLICATIONS

International Search Report and Written Option issued in PCT Application No. PCT/US2018/033434, dated Oct. 22, 2018, in 16 pages.

*Primary Examiner* — Rene T Towa
(74) *Attorney, Agent, or Firm* — Knobbe, Martens, Olson & Bear LLP

(57) ABSTRACT

Embodiments of devices and methods for collecting gastrointestinal samples using a capsule-shaped device that is swallowed are provided.

10 Claims, 18 Drawing Sheets

Related U.S. Application Data 19, 2017, provisional application No. 62/525,183, filed on Jun. 26, 2017, provisional application No. 62/528,406, filed on Jul. 3, 2017, provisional application No. 62/541,379, filed on Aug. 4, 2017, provisional application No. 62/578,289, filed on Oct. 27, 2017, provisional application No. 62/595,576, filed on Dec. 6, 2017, provisional application No. 62/627,175, filed on Feb. 6, 2018.

(56) References Cited

U.S. PATENT DOCUMENTS

| | | | |
|---|---|---|---|
| 3,315,660 A | 4/1967 | Abella | |
| 3,485,235 A | 12/1969 | Felson | |
| 3,528,429 A * | 9/1970 | Beal | A61B 10/02 600/572 |
| 3,683,890 A * | 8/1972 | Beal | A61B 10/02 600/431 |
| 4,186,730 A * | 2/1980 | Bucalo | C12Q 1/24 435/309.1 |
| 4,187,860 A * | 2/1980 | Villari | A61B 5/15003 600/580 |
| 4,481,952 A | 11/1984 | Pawelec | |
| 4,735,214 A | 4/1988 | Berman | |
| 5,611,787 A * | 3/1997 | Demeter | A61J 15/003 604/270 |
| 5,738,110 A | 4/1998 | Beal et al. | |
| 5,971,942 A | 10/1999 | Gu | |
| 6,149,607 A | 11/2000 | Simpson et al. | |
| 7,037,275 B1 | 5/2006 | Marshall et al. | |
| 2004/0039350 A1* | 2/2004 | McKittrick | A61J 15/0003 604/270 |
| 2004/0097834 A1 | 5/2004 | Stoltz | |
| 2007/0161928 A1* | 7/2007 | Sprenkels | B01L 3/502707 600/573 |
| 2007/0173738 A1 | 7/2007 | Stoltz | |
| 2008/0208077 A1* | 8/2008 | Iddan | A61B 5/14546 600/582 |
| 2011/0060189 A1 | 3/2011 | Belson | |
| 2011/0208011 A1* | 8/2011 | Ben-Horin | A61B 1/00156 600/300 |
| 2015/0064241 A1 | 3/2015 | Conrad | |
| 2016/0038086 A1 | 2/2016 | Wrigglesworth et al. | |

FOREIGN PATENT DOCUMENTS

| | | |
|---|---|---|
| JP | 05228128 A | 9/1993 |
| WO | WO 79/00811 | 10/1979 |
| WO | WO 88/09162 | 12/1988 |
| WO | WO 2005/046485 | 5/2005 |
| WO | WO 2013/120184 | 8/2013 |
| WO | WO 2014/140334 | 9/2014 |

* cited by examiner

DEVICES AND METHODS FOR COLLECTING GASTROINTESTINAL SAMPLES

CROSS REFERENCE TO RELATED APPLICATIONS

This application is a national stage application of the Patent Cooperation Treaty (PCT) international application titled "Devices And Methods For Collecting Gastrointestinal Samples", international application number PCT/US2018/033434, filed in the United States Patent and Trademark Office on May 18, 2018, which claims priority to and the benefit of the provisional patent application titled "Devices And Methods For Collecting Gastrointestinal Samples", application No. 62/509,014, filed in the United States Patent and Trademark Office on 19 May 2017, the provisional patent application titled "Devices And Methods For Collecting Gastrointestinal Samples", application No. 62/510,247, filed in the United States Patent and Trademark Office on 23 May 2017, the provisional patent application titled "Devices And Methods For Collecting Gastrointestinal Samples", application No. 62/512,719, filed in the United States Patent and Trademark Office on 30 May 2017, the provisional patent application titled "Devices And Methods For Collecting Gastrointestinal Samples", application No. 62/517,841, filed in the United States Patent and Trademark Office on 9 Jun. 2017, the provisional patent application titled "Devices And Methods For Collecting Gastrointestinal Samples", application No. 62/522,078, filed in the United States Patent and Trademark Office on 19 Jun. 2017, the provisional patent application titled "Devices And Methods For Collecting Gastrointestinal Samples", application No. 62/525,183, filed in the United States Patent and Trademark Office on 26 Jun. 2017, the provisional patent application titled "Devices And Methods For Collecting Gastrointestinal Samples", application No. 62/528,406, filed in the United States Patent and Trademark Office on 3 Jul. 2017, the provisional patent application titled "Devices And Methods For Collecting Gastrointestinal Samples", application No. 62/541,379, filed in the United States Patent and Trademark Office on 4 Aug. 2017, the provisional patent application titled "Devices And Methods For Collecting Gastrointestinal Samples", application No. 62/578,289, filed in the United States Patent and Trademark Office on 27 Oct. 2017, the provisional patent application titled "Devices And Methods For Collecting Gastrointestinal Samples", application No. 62/595,576, filed in the United States Patent and Trademark Office on 6 Dec. 2017, and the provisional patent application titled "Devices And Methods For Collecting Gastrointestinal Samples", application No. 62/627,175, filed in the United States Patent and Trademark Office on 6 Feb. 2018.

INCORPORATION BY REFERENCE

All publications and patent applications mentioned in this specification are herein incorporated by reference in their entirety to the same extent as if each individual publication or patent application was specifically and individually indicated to be incorporated by reference.

FIELD

This application relates to the field of gastrointestinal diagnosis and treatment.

BACKGROUND

It has recently been recognized that mammalian gastrointestinal (GI) tract microbiomes perform many vital physiological functions that benefit their host organism, comprising digestion, producing essential amino acids and vitamins, regulating the immune system, providing resistance to disease, and even modifying appetite, and behavior. Yet we know very little about the functions of hundreds or thousands of microbial species in mammalian GI tracts. The variety of microbes in a single individual at different points of the GI tract is staggering. Due to the complexity of this microbial ecology in a single individual and the variability among individuals, there exists a need to routinely sample and analyze the microbial community living in all regions of the GI tract, along with their associated metabolites, as well as their interactions with the host. The metabolites and secondary metabolites play a key role in the two way communication between the microbes and their hosts and can greatly impact the physiological state of the host. Furthermore, the analyses of the gut microbes can correlate to states of health and disease, as well as guide and measure the effect of treatment.

SUMMARY OF THE DISCLOSURE

The present invention relates to devices and methods for collecting gastrointestinal samples using a capsule-shaped device that is swallowed.

In an initial aspect, a device for collecting gastrointestinal samples is provided. The device comprises a capsule; and a tube-shaped body wound, twisted or folded within said capsule, the body comprising an open end and a closed end.

In some embodiments, the tube-shaped body comprises a narrowed portion configured to limit a sampling rate of the device. The tube-shaped body can comprise an internal diameter of about 0.2 to 2.5 mm. In some embodiments, the tube-shaped body comprises an external diameter of about 0.4 to 3.0 mm. In some embodiments, the tube-shaped body comprises an external diameter of about 5.0 to 7.0 mm. The tube-shaped body can comprise a length of about 1 to 200 cm. In some embodiments, the tube-shaped body has an aspect ratio of 5 or greater. In some embodiments, movement of gastrointestinal samples into the tube-shaped body is driven by a pressure differential between a radially collapsed and radially expanded body.

In some embodiments, the open end of the tube-shaped body can comprise a one way valve. The cracking pressure of the one way valve can be in the range of about 0.03 to 15 pounds per square inch. The maximal outward radial pressure exerted by expanding tube-shaped body can be in the range of about 10 to 150 grams-force per cm length of body. The flow of fluid sample through the open end of the body can be between 1 to 500 microliters per hour.

Spatial resolution of the sampling of the device can be about +/−1 foot of a 30 foot long gastrointestinal tract. The tube-shaped body can be hollow. The tube-shaped body can comprise a collapsed internal lumen. In some embodiments, the tube-shaped body is wound as a spiral around a central axis. The spiral can be axially offset around the central axis. In some embodiments, the tube-shaped body is twisted around a central axis to form a helix or coil. The tube-shaped body can be twisted around a central axis to form a superhelix or super-coil. In some embodiments, the tube-shaped body is folded into an accordion configuration. The tube-shaped body can be folded along a central axis into a creased configuration. The tube shaped body is not invaginated when placed within the capsule. The maximal diameter of the tube-shaped body is smaller than the diameter of the capsule.

The tube-shaped body can be configured to transition to its relaxed state upon dissolution of the capsule. In some embodiments, the capsule is ruptured by expansion force of the tube-shaped body. The tube-shaped body can be configured to transition to its relaxed state upon degradation of a covering element on the tube-shaped body. In some embodiments, wherein the capsule comprises one or more covering elements surrounding the tube-shaped body. The capsule can comprise at least a first and a second pH sensitive degradable covering element surrounding the tube-shaped body. In some embodiments, at least one of the first and second covering elements degrades at a pH of about 6.4-7 or lower. The device can be configured to sample gastrointestinal contents for about 1 minute to 1 hour. In some embodiments, the device is configured to sample gastrointestinal contents for about 1 hour to 8 hours. Different portions of the wound, twisted or folded tube-shaped body can comprise different degradable covering elements. In some embodiments, covering elements positioned closer to the open end are configured to degrade faster than covering elements positioned farther from the open end. In some embodiments, covering elements positioned closer to the open end are configured to degrade at a lower pH than covering elements positioned farther from the open end.

In some embodiments, a second end of the tube-shaped body is in fluid communication with an opening in the capsule.

The tube shaped body can be coiled to form a plurality of flat disks. In some embodiments, the tube-shaped body is coiled to form three flat disks. Each disk can be configured to uncoil at a different rate to target different portions of the gastrointestinal tract. In some embodiments, the open end is positioned on an inside of the wound, twisted, or folded tube-shaped body. The open end can be positioned on an outside of the wound, twisted, or folded tube-shaped body. In some embodiments, the capsule comprises a split capsule configured to split in the right colon. In some embodiments, the capsule can comprise a tube-shaped body configured to unfold in the right colon. The tube shaped body can comprise an open end of a tube-shaped body configured to open in the right colon.

A collection volume percentage of the device can be at least 50%. In some embodiments, a collection volume percentage of the device is at least 100%. A dead volume of the device can be less than about 15%. In some embodiments, a volume of the device is less than about 2 ml. The volume of the device can be less than about 1 ml.

In some embodiments, the device comprises a detector configured to detect a location identification parameter. The location identification parameter can comprise at least one of pH, color, bacterial count, bacterial identity, hormones, dissolved gases, enzymatic activity, biochemical markers, capsule movement patterns, and intraluminal pressure.

In some embodiments, the device comprises an actuator. The actuator can comprise an elastic material. In some embodiments, the actuator comprises a hollow bladder. The actuator can be spaced apart from an end of the capsule, creating a space between the actuator and the capsule. In some embodiments, the capsule comprises an orifice that is positioned on the body within the space. The orifice can comprise a movable seal configured to open or close the orifice. In some embodiments, the orifice comprise a degradable covering element. The actuator can comprise a first collapsed state and a second expanded state. The space can comprise a fluid.

In some embodiments, a length of the tube-shaped body does not change during the sample collection process.

In another aspect, a method of producing a device for sampling gastrointestinal contents is provided. The method comprises winding, twisting or folding a tube-shaped body; and placing said wound, twisted or folded tube-shaped body inside a capsule.

In some embodiments, the internal lumen of the wound, twisted or folded tube-shaped body is radially collapsed. The tube-shaped body or an opening of the tube-shaped body can be covered with an enteric degradable material.

In another aspect, a method of sampling gastrointestinal contents is provided. The method comprises delivering the device of claim 1 into the gastrointestinal tract; allowing flow of gastrointestinal contents into said tube-shaped body; and recovering said device from the stool.

In some embodiments, radial expansion of the collapsed internal lumen of said tube-shaped body causes said flow of gastrointestinal contents into said tube-shaped body.

In yet another aspect, a method of sampling gastrointestinal contents is provided. The method comprises delivering a device comprising a capsule; and tube-shaped body wound, twisted, or folded within the capsule, into the gastrointestinal tract; and allowing flow of gastrointestinal contents into the tube-shaped body, and recovering the device from the stool.

In some embodiments, allowing flow comprises radially expanding the tube-shaped body. In some embodiments, radially expanding the tube-shaped body comprises dissolving the capsule. In some embodiments, radially expanding the tube-shaped body comprises degradation of a covering element on the tube-shaped body or on the capsule.

In yet another aspect, a device for collecting gastrointestinal samples is provided. The device comprises a body; an opening on a sidewall of the body; a plurality of plates mounted along a spindle running along a longitudinal axis of the body, adjacent plates comprising a space between them; and an actuator configured to displace the plurality of plates along the longitudinal axis of the body, wherein longitudinal displacement causes each space between the plates to align with the opening. The plates can be disk shaped. In some embodiments, the plates comprise a same shape as a cross section of the body and seal against an inner wall of the body. The opening can be slit shaped. The body can be capsule shaped. In some embodiments, the body comprises a covering. The device can comprise a cavity for stool collection. In some embodiments, the actuator comprises an elastic tensile member.

In another aspect, a device for collecting gastrointestinal samples is provided. The device comprises an outer body; a covering element over the outer body; an opening in a sidewall of the outer body; a hollow piston shaped to mate to an inner surface of the outer body, the piston positioned at an end of the body; and an actuator configured to advance piston to an opposite end of the body to cover the opening in the sidewall.

In some embodiments, the device comprises a second opening positioned diametrically opposed to the opening. The device can comprise an opening in the body. In some embodiments, the actuator comprises material that expands when wet. The piston can be cup shaped. In some embodiments, the actuator comprises a spring compressed by a moisture degradable restraint.

In yet another aspect, a device for collecting gastrointestinal samples. The device comprises a body; a collecting member within the body; and opening on the body; a sealing element movable from a first position where the opening is open to a second position where the opening is sealed by the sealing element; and an actuator configured to move the sealing element.

In some embodiments, the collecting member comprises a porous material. The actuator can be a wet actuator. In some embodiments, the actuator comprises a dehydrated sponge or superabsorbent material. The device can comprise a wick near the opening. In some embodiments, the collecting member is movable from a first position in which the opening is not in fluid communication with the collecting member to a second position in which the opening is in fluid communication with the collecting member. The collecting member can be movable from a second position in which the opening is in fluid communication with the collecting member to a third position in which the collecting member seals the opening. In some embodiments, the collecting member is the sealing element. The actuator can comprise a moisture degradable restraint mechanism. In some embodiments, the actuator comprises a double trigger moisture degradable restraint mechanism. The actuator can be the sealing element. The device can comprise one or more additional openings. In some embodiments, the actuator comprises a plurality of actuator elements. In some embodiments, the actuator moves the sealing element into a sealing position within about 1-60 minutes. The device can comprise a covering element. In some embodiments, the device comprises a pH sensitive degradable covering element configured to cover the opening. The device can comprise a second opening covered by a second pH sensitive degradable covering element.

In another aspect, a device for collecting gastrointestinal samples is provided. The device comprises a body; an opening in fluid communication with the body configured to allow gastrointestinal samples to enter the body; and an external pH sensitive degradable covering element covering the opening; and an internal pH sensitive degradable covering element covering the opening.

In some embodiments, the external covering element is configured to degrade at or above a target pH level. The internal covering element can be configured to degrade at or below a target pH level. In some embodiments, the external covering element is configured to degrade at a pH of about 6.4-7 or above. The internal covering element can be configured to degrade at a pH of about 6.4-7 or below. In some embodiments, the external covering element is configured to dissolve in small intestines. The internal covering element can be configured to dissolve in the right colon. In some embodiments, the external covering element comprises anionic acrylic polymers with methacrylic acid as a functional group. The internal covering element can comprise cationic polymer with dimethylaminoethyl methacrylate as a functional group.

In another aspect, a system for collecting gastrointestinal samples is provided. The system comprises a first stomach-targeting capsule; a second small intestine targeting capsule; and a third colon targeting capsule, wherein the three capsules are configured to be ingested at the same time.

In some embodiments, at least one of the capsules comprises a pH sensitive degradable material configured to degrade at an area to be targeted. At least one of the capsules can comprise an internal pH sensitive degradable covering element and an external pH sensitive degradable material. In some embodiments, at least one of the capsules comprises a degradable covering element with a thickness selected to degrade at an area to be targeted. The capsules can comprise a pH sensitive degradable covering element. In some embodiments, the covering element is configured to degrade at a pH of about 5.5 or higher. The capsules can be connected by a flexible connection element.

In another aspect, a system of collecting gastrointestinal samples is provided. The system comprises a capsule; a plurality of collecting members each comprising a hollow body within the capsule and a degradable covering element, the collecting members linked together by connecting members to form a chain, wherein filling of a collecting member with sample triggers collection by a subsequent collecting member in the chain. The collecting members can each comprise an opening. The degradation or dissolution of a moisture degradable material exposes the openings of the plurality of the collecting members in a serial manner.

In some embodiments, a length of each collecting member is about 1-30 mm A length of each connecting member can be about 1-100 mm. In some embodiments, the collecting members are arranged linearly or centrally around a spoke. At least some of the collecting members can comprise a seal or one way valve. In some embodiments, a negative pressure differential is used to collect a sample. The negative pressure differential can be caused by capillary forces or expansion of a collapsed member. In some embodiments, the covering element is configured to degrade based on one of hydration time or pH. Filling of a collecting member can trigger closure or sealing of the collecting member. In some embodiments, filling is detected by a target volume, a target duration, or a specific pH. Some of the collecting members can comprise a seal. In some embodiments, some of the collecting members comprise a flow sensor.

BRIEF DESCRIPTION OF THE DRAWINGS

The novel features of the invention are set forth with particularity in the claims that follow. A better understanding of the features and advantages of the present invention will be obtained by reference to the following detailed description that sets forth illustrative embodiments, in which the principles of the invention are utilized, and the accompanying drawings of which:

DETAILED DESCRIPTION

Figure 1:
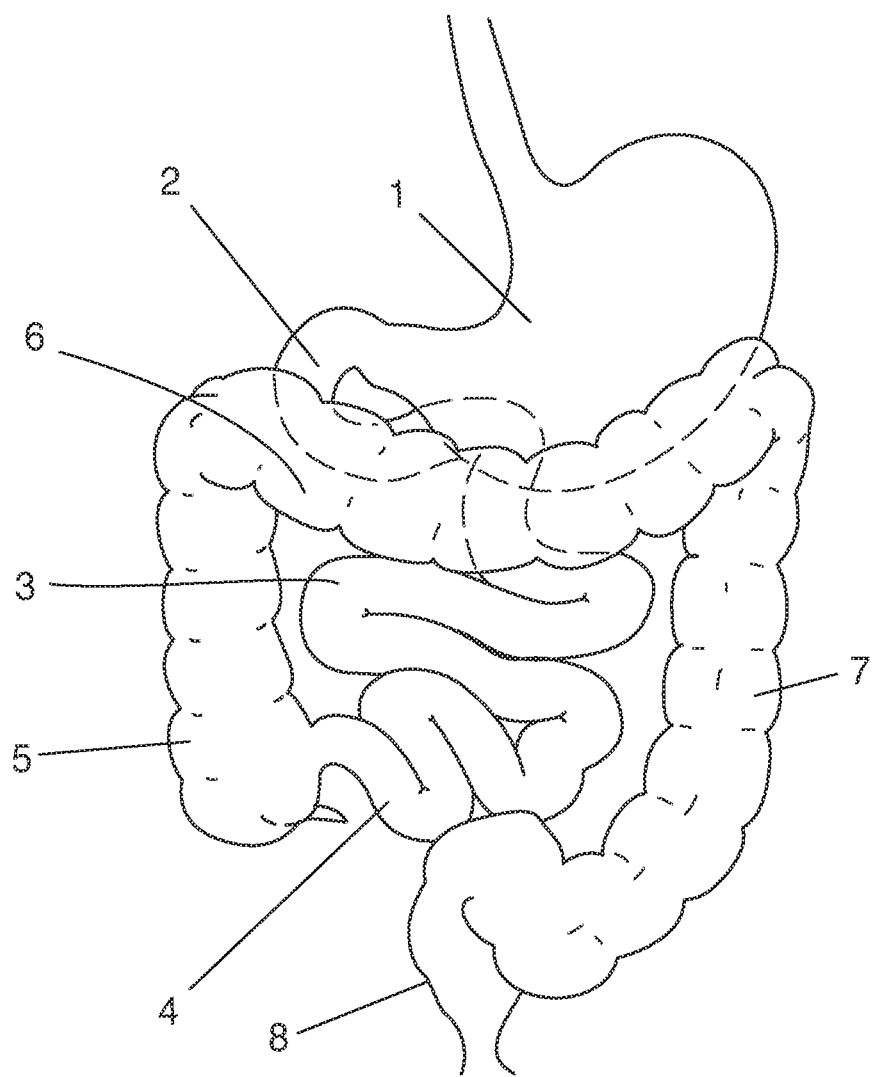
FIG. 1 illustrates the anatomy of the human gastrointestinal tract.

As used herein, the terms "analysis", "analyses" and "analytical techniques" refer to techniques comprising pH measurement, visual inspection, spectral analysis, pressure measurement, oxygen content, colorimetry, phylogenetic, proteomic, metabolomics, mass spectrometry (MS), nuclear magnetic resonance (NMR), chromatography, electrophoresis, presence of hemoglobin, immunoassay, protein-protein interactions, fluorescence, flow cytometry, host-microbiome interactions, nucleic acid hybridization, mRNA or cDNA transcription analysis, and sequencing of nucleic acids comprising entire genomes, random fragments, or specific sections such as the 16S rRNA of microbes and any combination of the techniques above, whether in parallel or sequentially. Overlaying all or a subset of these analyses on top of clinical or phenotypical information will provide a comprehensive picture of the physiology of the GI tract and the state of the microbiome in health and disease, as well as the safety and efficacy of treatment. The ability to combine information about the identities and diversity of microbial community members obtained from 16S rRNA sequencing, the metabolic potential obtained from meta-genome sequence data, and gene expression and protein production obtained from meta-proteome data, enables exploration of the gut microbiota at multiple molecular levels simultaneously.

As used herein, the term "gastrointestinal samples" comprises liquids, digestive juices, mucus, microbes, metabolites, cells, cell fragments, carbohydrates, fats, lipids, proteins, peptides, immune system molecules, immune system cells, blood, hemoglobin, food particles, acids, bases, gases, small molecules, hormones, nucleic acids, drugs, pro-drugs, drug metabolites, volatile molecules, dissolved or free gases, and other molecules present in the GI tract from the mouth to the anus. As used herein, the term "microbe" comprises one or more species or strains of microscopic agents from the three domains eubacteria, eukarya and archaea as well as viruses such as phages. As used herein, a group of microbes, or a microbial population, taken as a whole is referred to as a "microbiota" and when the group is quantitated or measured in some manner it is referred to as a "microbiome." As used herein, the terms "immune system molecules or immune system cells" comprise all forms of lymphocytes, leukocytes, antigen-presenting cells, antibodies, antigens, markers of inflammation, c-reactive protein (CRP), antimicrobial molecules, proteases, cell signaling proteins, cytokines, chemokines, hormones, neurotransmitters, interleukins, vitamins, major histocompatibility (MHC) molecules, complement system molecules, anti-viral molecules, and the like.

As used herein, the term "degradable material" comprises "moisture degradable material" and also "enteric degradable material" as described more fully below.

As used herein, the term "moisture degradable material" means a material that dissolves, degrades, hydrolyzes, hydrates, softens, or otherwise loses strength when exposed to moisture at a broad range of pH levels, or in a narrow range of pH levels, at a broad range of times or in a narrow range of times, and in the presence or absence of human or microbial enzymes that can metabolize or degrade such a material. Moisture degradable materials comprise polyvinyl alcohol (PVA), polyvinyl acetate phthalate (PVAP), polyvinyl chloride, polyvinylpyridine acrylic acid, fatty acids, waxes, shellac, plant fibers, paper, cellulosic material, starch, methyl acrylate-methacrylic acid copolymers, cellulose acetate phthalate (CAP), cellulose acetate succinate, hydroxypropyl methyl cellulose phthalate, hydroxypropyl methyl cellulose acetate succinate, methyl methacrylate, methacrylic acid, polyacryl, cellulose acetate, trimellitate, sodium alginate, zein, starch, pectin, gelatin, cross-linked gelatin, carbohydrates, gum arabic, salts, sodium hypochlorite, lithium hypochlorite, calcium hypochlorite, dichlor, trichlor, sugars, proteins, hydrogels, as well as polymers, copolymers, acetates, sheets, coatings, foams, mixtures, or derivatives thereof. The functionalities of the moisture degradable material comprise protecting the device from exposure to gastrointestinal content until the desired location in the GI tract is reached, allowing motion of the actuator to start or stop the sampling of gastrointestinal fluids after sufficient sample has been collected, and/or acting as a sanitizing bactericide to stop all metabolic processes when dissolved in the collected samples. By way of example, solid salt such as sodium chloride that is in fluid communication with the collecting member will dissolve when gastrointestinal fluids are introduced into the sampling capsule. The solid salt acts to resist the motion of an actuator. When dissolved, the salt can no longer physically prevent the sealing of the sampling capsule by the actuator. Furthermore, the resulting high dissolved salt concentrations in the collecting member kills the microbes in the device, thereby helping preserve the biomolecules therein for analysis at a later time.

As used herein, the term "enteric degradable material" refers to compounds and coating techniques that enable the collecting member of a device to only come into fluid communication with a portion of the GI tract that is distal to the stomach. Sample enteric degradable materials comprise methyl acrylate-methacrylic acid copolymers, cellulose acetate phthalate (CAP), cellulose acetate succinate, hydroxypropyl methyl cellulose phthalate, hydroxypropyl methyl cellulose acetate succinate (hypromellose acetate succinate), polyvinyl acetate phthalate (PVAP), methyl methacrylate-methacrylic acid copolymers, shellac, cellulose acetate trimellitate, sodium alginate, zein, and combinations or derivatives thereof. The enteric degradable materials disclosed herein control the flow of fluid into a device at a point distal to the stomach. This is in contrast to enteric and enteric delivery technologies used in drug delivery that control the flow of substances out of the capsule and into the body at a point distal to the stomach. For example, flow of substances out of a capsule can be achieved via diffusion through a swollen and hydrated, but not dissolved, enteric coating. In contrast, flow of gastrointestinal samples into a device requires bulk flow of liquid into the device through a fully dissolved or ruptured coating. Therefore, enteric coatings that work for drug delivery may not work well for controlling the function of a sample collection device. By way of example, the sampling device can be made of an elastic material that is compacted inside a delivery capsule, which is then coated by an enteric degradable material. The elastic sampling device exerts radial or axial pressure on the enteric coating from the inside the capsule to rupture the enteric coating and start bulk flow of liquid samples into the sampling device.

Enteric degradable materials further comprise timed release or time degradable materials that degrade mainly after the device has had sufficient time to traverse the small intestines and enter into the colon. By way of example, a device is coated with a time release coating such as guar gum and then further coated with an enteric degradable material such as methacrylic acid that only dissolves at a pH present in the small intestine. The external enteric degradable material protects the device during the transit through an acidic stomach. The enteric degradable material degrades in the pH of the small intestine, thereby exposing the next coating of guar gum. The guar gum coating takes 2 hours to degrade which protects the device through the remaining 2 hour transit through the small intestines. Finally, when the guar gum coating degrades in the colon, the device collects a gastrointestinal sample in the colon. As used herein, the term "colonic targeting" refers to compounds and coating techniques that enable the collecting member of a device to only come into fluid communication with a portion of the GI tract that is distal to the small intestine. Colonic targeting materials comprise materials that are preferentially degraded at pH levels, gas content, color, lumen size, enzymes, metabolism or microbes that are preferentially present in the colon relative to the small intestines. Example materials that are useful coatings for colonic targeting comprise methacrylic acid, methyl methacrylate-methacrylic acid copolymers, starch, pectin, chitosan, guar gum, dextran, and combinations or derivatives thereof.

As used herein, the term "porous" means any open cell structure. Such materials comprise open cell foams, fibers, channeled materials, papers, cellulosics, acetates, cotton, cloth, gauze, sponges and the like.

As used herein, the term "active agent" comprises drugs, pro-drugs, nutritional supplements, prebiotics, probiotics, postbiotics, synbiotics, microbes, immune system molecules, immune system cells, immune system modifiers, dyes, combinations of the above, and the like. As used herein, the term "hydrophilic" means water forms a contact angle of less than 90 degrees on a surface. As used herein, the term "superhydrophilic" means water forms a contact angle of less than 1 degree on a surface.

Unless otherwise defined, all technical and scientific terms used herein have the same meaning as commonly understood by one of ordinary skill in the art to which this invention belongs. Although methods and materials similar or equivalent to those disclosed herein can be used in the practice of the present invention, suitable methods and materials are disclosed below. In case of conflict, the patent specification, including definitions, will control. In addition, the materials, methods, and examples are illustrative only and not intended to be limiting.

Before explaining at least one embodiment of the invention in detail, it is to be understood that the invention is not limited in its application to the details of construction and the arrangement of the components set forth in the following description. The invention is capable of other embodiments or of being practiced or carried out in various ways. Also, it is to be understood that the phraseology and terminology employed herein is for the purpose of description and should not be regarded as limiting.

FIG. 1 shows the regions of the human gastrointestinal (GI) tract that are sampled by the device and methods described herein. Food enters stomach 1 where muscles mix the food and liquid with digestive juices. The stomach slowly empties its contents, called chyme, into the duodenum 2, also referred to as the proximal portion of the small intestine. The muscles of the small intestine mix food with digestive juices from the pancreas, liver, and intestine, and push the mixture forward into the jejunum 3, also referred to the mid portion of the small intestine, for further digestion. The walls of the small intestine absorb water and the digested nutrients into the bloodstream until the ileum 4, also referred to as the distal portion of the small intestine, is reached. As peristalsis continues, the waste products of the digestive process move into the ascending colon 5, also referred to as the right colon or proximal colon portion of the large intestine where complex carbohydrates are fermented by microbes. Waste products from the digestive process include undigested parts of food, fluid, and older cells from the lining of the GI tract get transferred into the transverse colon 6, also referred to as the mid colon. The descending colon 7, also referred as the left colon or distal colon portion of the large intestine absorbs water and changes the waste from liquid form into solid stool. Peristalsis helps move the stool into rectum 8 and from there into the toilet during a bowel movement. The pH levels and other biochemical and physical differences between these regions of the GI tract are described more fully in tables 1 and 4.

Most of the microbial activity occurs in the small intestine and right colon, which are the prime regions of sample collection. The inventor has determined experimentally that fermentation activity of the microbes is reduced after stool arrives in the transvers colon. Based on the typical transit times listed in Table 1 below, the desired sampling window time is up to 8 hours, which is long enough for the sampling device to reach the right colon. After the right colon, the collected samples are not significantly different than a stool sample collected outside the body.

Many of the microbes and other gastrointestinal samples of interest reside in the mucus layer on the GI tract's lumen. At any given point in time, a region of the GI tract can be empty and collapsed, contain gas, fluid, semisolid content, solid content, or a mixture of each. When a region of the GI tract is full of gas, the collecting member can be sitting on an exposed lumen wall without any surrounding free-flowing fluid. It is preferable that the collecting member not only be able to collect surrounding fluid, but also be able to collect, wick or absorb through direct contact or capillary action the gastrointestinal samples in the form of a thin layer of mucus on the lumen surface that doesn't flow easily. Prior art capsule collection devices rely on vacuum chambers, indentations or invaginated collection chambers that are designed to fill up with free-flowing gastric fluids. But intestinal gas, rather than free-flowing fluids, may exist in the surrounding of the capsule at that particular region of the GI tract at the moment of sampling by the device. Therefore, prior art devices that rely on a vacuum, indentations or invaginated collection chambers would only suck in the gas content or not collect any liquid sample at all. Therefore, these prior art collection devices would not be effective in sampling the areas of the GI tract that do not contain large amounts of fluid at the time the capsule is sampling the area. For example, if flow into the sampling opening of the collecting member is driven by a vacuum reservoir, then as soon as the sampling opening is exposed to gas, the gas will flow into collecting member extremely quickly relative to a more viscous fluid sample, thereby filling the collecting member with gas almost instantaneously. The sampling rate of the present disclosure can be relatively unaffected by the viscosity of the material being sampled due to the independently-controlled rate of actuator displacement, reservoir re-inflation, unwinding or unfolding of the collecting member, or the wicking action of the collecting member. In some embodiments utilizing a positive displacement collecting mechanism, for every unit of volume that the actuator is displaced, an equal unit of volume of sample is collected, independent of whether the sample collected is gas or fluid in nature. In some embodiments of a wound and collapsed elastic lumen forming the collecting member, the rate of unwinding and expansion of the collapsed lumen is controllable by the size of the sampling opening and/or the rate of degradation of the degradable material that restricts unwinding and expansion of the elastically collapsed lumen. It is important to control the rate of sample collection into collecting member to be between 1 to 60 minutes to ensure that a liquid sample is obtained. Even if the device is in the colon, which is full of gas and liquid, the peristaltic forces moving the device around randomly will cause the opening to contact a patch of liquid at some point during the 1 to 60 minute time window. In some embodiments where the sample collection occurs in less than 1 minute, the device might collect only a sample of gas. In some embodiments where the sample collection occurs over more than 60 minutes, then the location specificity of where the sample is collected is lost since the device can travel to a different region of the GI tract in one hour.

In embodiments wherein the collecting member creates capillary or wicking forces, the surface tension of gastrointestinal fluids interacting with the collecting member allows for only liquid gastrointestinal samples to be collected. Gas in the collecting member will be easily displaced by liquids since the surface tension of a gas is far less than that of a fluid.

In some embodiments, the device or collecting member does not expand in volume or rely on a pressure differential in order to collect a gastrointestinal sample. Rather, wicking or capillary forces alone drive the collection of gastrointestinal samples into a collecting member.

In some embodiments, the device or collecting member grows smaller in overall volume during the collection process of a gastrointestinal sample. The reduction in overall volume displaces trapped gas present in the device and/or enables a sealing action to isolate the collected gastrointestinal sample from further contact with the GI tract. This embodiment is in contrast to prior art devices that expand in overall volume to create a negative pressure differential that drives samples into the device.

In some embodiments, the capsule is the size and shape of a size 3, 2, 1, 0, 00 or 000 capsule.

In some embodiments, the collecting member comprises the wet, dried or lyophilized reagents required for cell lysis. Example reagents required for cell lysis when rehydrated by the gastrointestinal sample comprise sodium dodecyl carbonate, tris (2-carboxyethyl) phosphine, 2-chloroacetamide, and/or tris buffer pH 8.5. In this manner, the cell contents are released into the collecting member and enzymatic activity will cease and the cell contents are thus prepared for further analysis techniques in-vivo or ex-vivo.

In some embodiments, the collecting member comprises the wet, dried or lyophilized reagents required for protein digestion. Example reagents required for protein digestion comprise trypsin and Lys-C protease. In this manner, enzymatic activity will cease and the proteins are thus prepared for a further analysis techniques in-vivo or ex-vivo. An example analysis step comprises mass spectrometry.

In some embodiments, the collecting member comprises the wet, dried or lyophilized reagents required for a reverse transcription reaction of the RNA contained in the gastrointestinal samples in real time while the device is still in the GI tract. The RNA in the gastrointestinal samples are labile and may degrade in the time between when the gastrointestinal samples are collected and when they are analyzed, which might be a matter of days. The product of reverse transcription is first strand complementary DNA (cDNA) which is much more stable. The reagents required for reverse transcription comprise reverse transcriptase, random or specific primers, ligation enzymes, deoxynucleotides (dNTP), RNase inhibitor, salts and buffers.

In some embodiments, the collecting member comprises wet, dried or lyophilized RNase inhibitor to minimize the degradation of mRNA until the gastrointestinal sample can be analyzed.

In some embodiments, a capsule body has a through hole as a collecting member. The through hole can create at least two openings in the capsule body. A cover made from a moisture degradable material, an enteric degradable material or a physically moveable cover creates a seal over one or more of the openings of the solid capsule body. At the correct sampling location, the through hole is exposed to the surrounding GI tract environment. Gastrointestinal samples flow or are wicked into the through hole. At the end of sampling, the openings in the solid capsule body are either left open or sealed to contain the gastrointestinal sample therein. If the holes are small enough, they would not need to be sealed after sampling since solid stool will impact itself on the capsule surface and seal the holes further down the digestive track.

In some embodiments, the solid capsule has multiple such holes and multiple such covers.

In some embodiments, an external concentric cylindrical sleeve forms the external cover and provides a fluid-tight seal of the two openings in the solid capsule body, thus preventing the through hole from being in fluid communication with GI tract. The external sleeve also comprises two diametrically opposed holes and when the external sleeve is rotated, these holes in the sleeve line up with the two openings in the solid capsule body. In this position, a gastrointestinal sample flows, is wicked or is absorbed into the through hole in the solid capsule body, while allowing gas contained therein to escape in either direction. After sufficient sampling time, the external sleeve rotates again and covers the two openings in the solid capsule body with a fluid-tight seal, thus preventing leakage or contamination of the collected gastrointestinal sample.

The through-hole feature in the embodiment above allows the gas inside the hole to escape easily as the gastrointestinal sample is being drawn into the hole due to capillary action. A blind hole will have a bubble of gas trapped at the bottom that may prevent sample from being drawn into the hole. An indentation in the capsule will not have the narrow straw-like shape that will enable capillary action to draw in the gastrointestinal sample.

In some embodiments, the collecting member contains a porous or water soluble substance or channels to enable wicking or diffusion of the gastrointestinal sample into the collecting member. In this embodiment, the collecting member can be a blind hole, since the gastrointestinal samples flow in via capillary action or diffusion versus bulk flow, and trapped gas can escape easily through the porous or water soluble collecting member. Example water soluble materials comprise solid or liquid forms of sugars, salts, polyvinyl alcohol, polyethylene glycol, lactose anhydride and the like. For example, a collecting member filled with solid particles of polyethylene glycol will pull into it the liquid of the gastrointestinal sample, thereby filling the collecting member with the liquid gastrointestinal sample as the water soluble material dissolves. A collecting member filled with a hyperosmotic salt solution or a material more hygroscopic than the GI samples themselves will draw into the collecting member a liquid gastrointestinal sample via osmotic or hydration forces. Water soluble materials such as polyethylene glycol or salts do not generally interfere with further analysis of the gastrointestinal sample, or can be removed later as part of the sample purification and preparation step. The rate of dissolution and/or the rate of diffusion of the water soluble material out of the device can be used to also control the rate of sampling of the gastrointestinal fluids into the device. Each sample should be collected in a time window of 1 to 60 minutes.

In some embodiments, the sampling opening in the body is sealed and only opens at a predetermined time or under predetermined conditions, such as a certain pH range or pressure level. The opening then reseals after a predetermined time to prevent further exposure of the collecting member to additional gastrointestinal samples. In some embodiments, a series of such openings is positioned around the outer surface of the capsule to enable multiple collection times, or sampling under multiple conditions.

In some embodiments, the actuator is a spring or elastic member that is pre-loaded prior to the patient swallowing the capsule Immediately before swallowing or during the act of swallowing, or at a time period after swallowing, the spring or elastic member starts to perform work as an actuator. In some embodiments, the actuator moves a collecting member relative to the opening in the body at a predefined rate. In some embodiments, the actuator moves the external cover across or around the capsule surface thereby sealing, or alternatively exposing the opening of a hole that forms a collecting member. Examples of springs or elastic member comprise linear and rotary springs made of metal or a polymer, such as a twisted or stretched polymeric band or elongated element.

In some embodiments, the spring is connected to a gear, ratchet, an escapement mechanism, a pendulum, rotary or linear damper, an element pushing or pulling a gas or fluid through an orifice, and/or a balance wheel to control the speed of rotation or displacement of the actuator over a predefined time period.

In some embodiments, the device comprises a battery that provides current to microchip circuit that makes quartz crystal vibrate. The microchip circuit detects the crystal's oscillations and turns them into regular electric pulses that open and/or close an active valve at the sampling opening, or drive a miniature electric stepping motor. The stepping motor converts electrical energy into mechanical power that serves as an actuator for the device.

In some embodiments, a pre-loaded spring or elastic actuator is prevented from doing work or stopped intermittently from doing work, by a removable mechanical restraint. In this manner, the removable mechanical restraint allows the spring or elastic actuator to fully or partially unwind or relax before the next mechanical restraint is reached. Example mechanical restraints include a safety latch, a trigger, a solenoid pin under electronic control, a piezoelectric element, or a moisture degradable element before exposure to moisture. In this manner, the energy to control the release of mechanical work of a spring or elastic actuator is much less than the energy stored in the spring or elastic actuator itself.

In some embodiments, the actuator can be powered by an onboard energy source such as a battery or capacitor.

In some embodiments, the actuator is driven by osmotic pressure. After swallowing, water enters a section of the capsule containing hygroscopic material such as a salt via a semipermeable membrane, which creates osmotic pressure that moves the actuator.

In some embodiments, the linear actuator is the osmotic material itself expanding inside one end of the device, wherein fluid enters the device through a small hole. As the osmotic material expands due to fluid intake, it acts as an actuator.

In some embodiments, the actuator displaces a valve stem that temporarily opens a sampling opening to be in fluid communication with a colleting member. Example means of establishing fluid communication comprise a through hole in a solid valve stem that is temporarily aligned with the sampling opening. Further displacement of the solid valve stem and subsequent lack of alignment of the hole with the sampling opening seals the sample in the collecting member.

In some embodiments, multiple sampling openings are connected to separate collecting members. The multiple sampling openings are arranged in a manifold and the displaced valve stem opens and closes each sampling opening in a serial manner one after the other, thereby sampling different regions of the GI track as the sample device is moved through the GI tract due to peristalsis over a time period of 1 minute to 8 hours.

In some embodiments, multiple sampling openings are connected to separate collecting members. The multiple sampling openings are arranged in a manifold and a moisture degradable material prevents fluid communication between each sampling opening and the associate collecting member. The moisture degradable material dissolves or degrades along one face or one direction only, similar to the burning of a fuse, so that the sampling openings are exposed in a serial manner one after the other, thereby sampling different regions of the GI track as the sample device is moved through the GI tract due to peristalsis over a time period of 1 minute to 8 hours. By way of example, the moisture degradable material is in the form of a long thin cylinder placed inside an open ended sleeve that exposes only one round face of the cylinder to the fluids of the GI tract. The sampling openings are arranged in a line along the long edge of the sleeve in a manifold pattern. As the face of the moisture degradable material dissolves or is degraded in the axial direction towards the closed end of the sleeve, the sampling openings are exposed to fluid communication with the GI tract in a sequential manner, thereby sampling the GI tract in a predefine sequence and with a controllable delay between sampling events that is set by the dissolution or degradation time of the exposed face of the moisture degradable material.

In some embodiments, the actuator is a hydrogel that swells when exposed to water. Example hydrogels comprise sodium polyacrylate.

The osmotic or hydrogel agent can be selected or designed to expand as a function of various pH levels in order to optimize sampling at specific regions of the GI tract. For example, an osmotic or hydrogel material that expands more rapidly at low pH will utilize more the collecting members to sample the stomach contents relative to the rest of the GI tract. Alternatively, an osmotic or hydrogel material that expands more rapidly at high pH will utilize more the collecting members to sample the distal small intestine contents relative to the rest of the GI tract.

In some embodiments, the device comprises a linear actuator that pushes or pulls stacked collecting members in an axial direction through the inside volume of the device underneath an opening in the middle region of the device. As successive collecting members are pushed or pulled underneath the opening, they are in turn exposed to the GI tract and absorb, wick or otherwise collect within them gastrointestinal samples. Between each collecting member is a fluid impervious element that prevents axial flow between the stacked collecting members. The fluid impervious element also prevents flow of the gastrointestinal fluid between the outer perimeter of the collecting member and the inner surface of the device. In this embodiment, the stacked collecting members start in one half of the device and move in an axial fashion to the second half of the device. The opening that exposes the collecting member to the GI tract is in the middle region of the device so that each collecting member passes underneath it once.

In some embodiments, the stacked collecting members are the spaces between thin disks of fluid impervious material mounted on a central stem. Each disk forms a fluid-tight seal against the inner surface of the body, yet is axially displaceable when pushed or pulled by the actuator. In this fashion, a succession of collecting members can be exposed to the GI tract under the opening.

Figure 2:
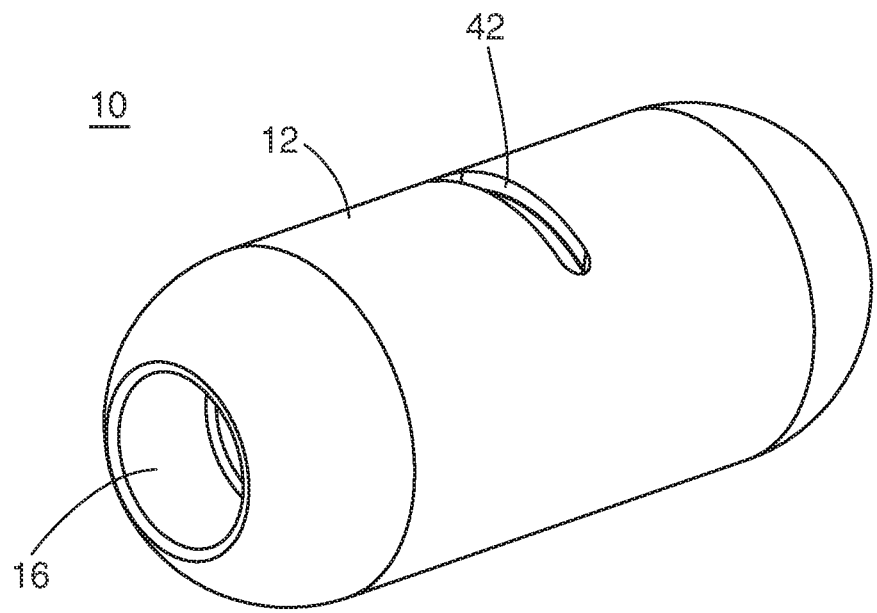
FIG. 2 illustrates in perspective view of an embodiment of the device.

With reference to the embodiment shown in FIG. 2, device 10 is shown in perspective view. Device 10 comprises body 12 with opening 42. Cavity 16 is used to allow compacted solid or semi-solid stool to enter into an invagination in body 12 to be included in the sample collected, since solid or semi-solid stool is unlikely to enter into the narrow opening 42.

Figure 3:
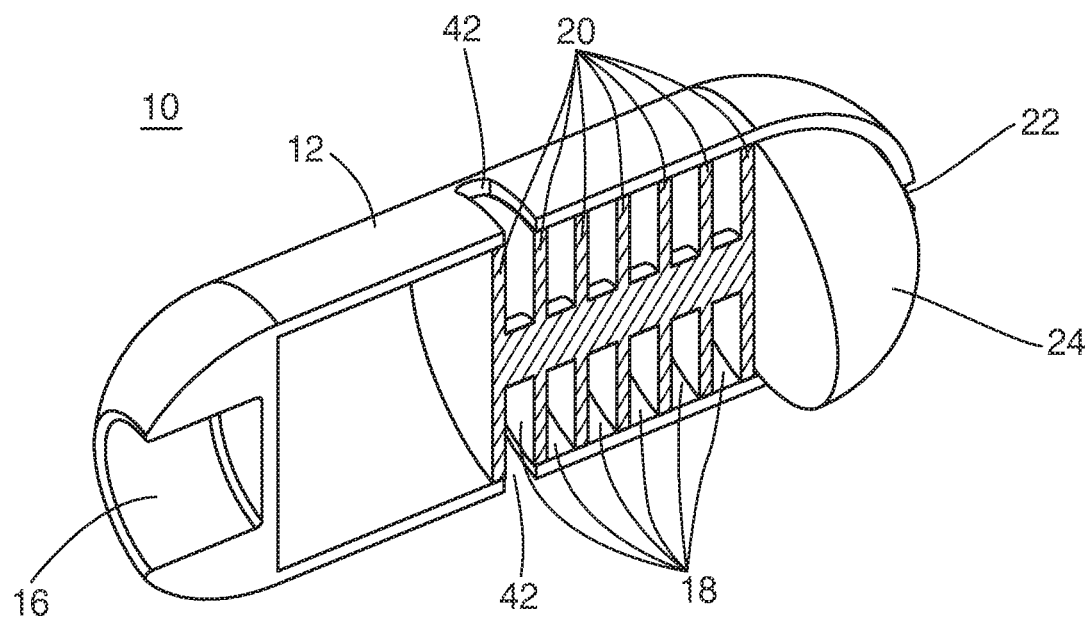
FIG. 3 illustrates a cut-away perspective view of an embodiment of the device.
Figure 4:
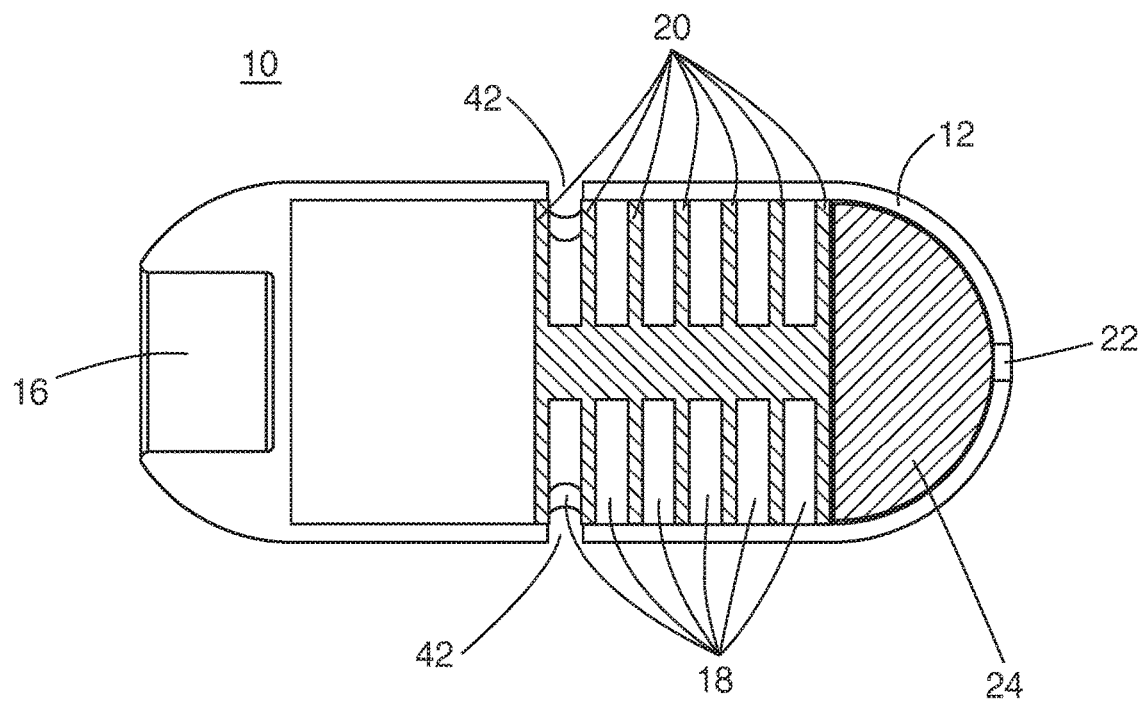
FIG. 4 illustrates a sectional view of an embodiment of the device at the commencement of collecting gastrointestinal samples.
Figure 5:
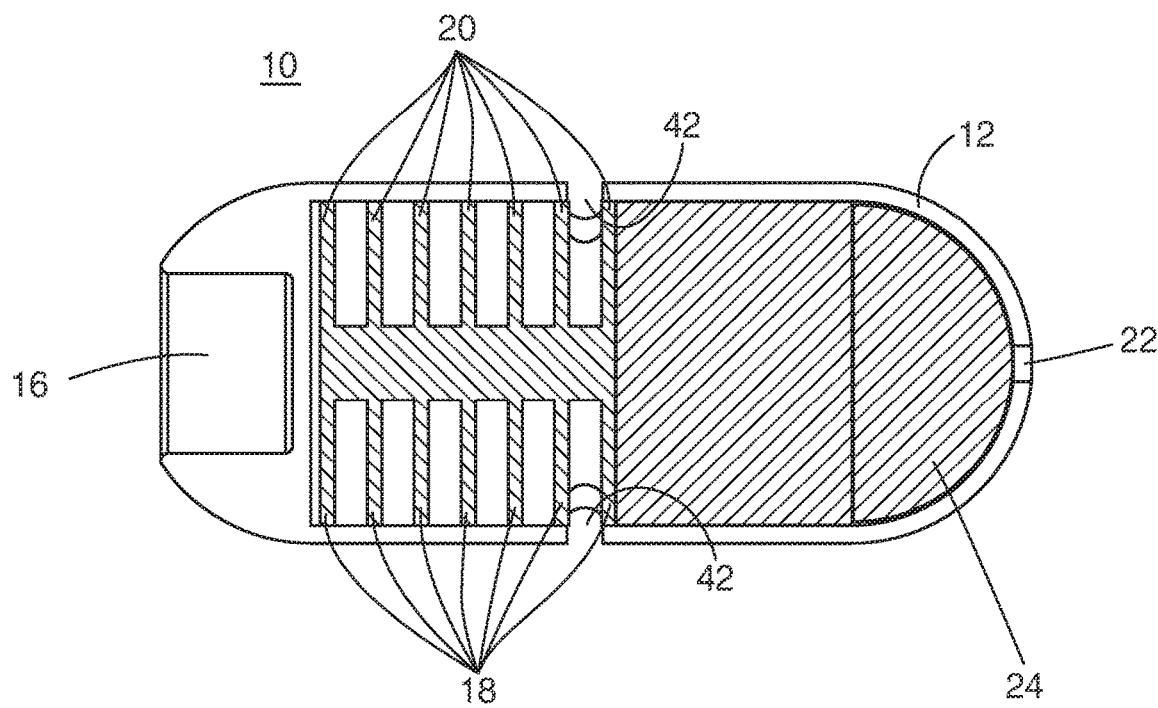
FIG. 5 illustrates a sectional view of an embodiment of the device after collecting gastrointestinal samples.

In FIG. 3, device 10 is shown in perspective view with body 12, collecting members 18 and thin disks 20 in section view. In FIG. 4, device 10 is shown in a cross section side view. Collecting members 18 are shown as a series of spaces between thin disks 20 made of fluid impervious material mounted on a central stem in the form of a spindle. Each thin disk 20 forms a fluid-tight seal against the inner surface of body 12. Each disk 20 is axially displaceable when pushed by the actuator 24. In this example, actuator 24 is a hydrogel or osmotic material that is in its initial unexpanded state. The material of actuator 24 expands when body fluids enter body 12 via hole 22. In this fashion, a succession of collecting member 18 is exposed to the GI tract under opening 42 when actuator 24 expands. In FIG. 5, actuator 24 is in its maximally expanded position. The gastrointestinal samples in each collecting member 18 are isolated from one another via thin disks 20.

In some embodiments, actuator 24 is a tensile elastic member that pulls collecting member 18 towards the end of body 12. The rate of motion of collecting member 18 is determined by the elasticity of actuator 24, the friction between the inner surface of body 12 and collecting members 18 and/or thin disks 20, and the resistance of flow of a gas or fluid present in body 12 to the outside environment through hole 22, which is this instance is a venting hole.

In some embodiments, the stacked collecting members are disks made from a porous material separated with disks of a fluid impervious material. Each fluid impervious disk forms a fluid-tight seal against the inner surface of the device, yet the stack of collecting members is axially displaceable when pushed or pulled by the actuator.

Figure 6:
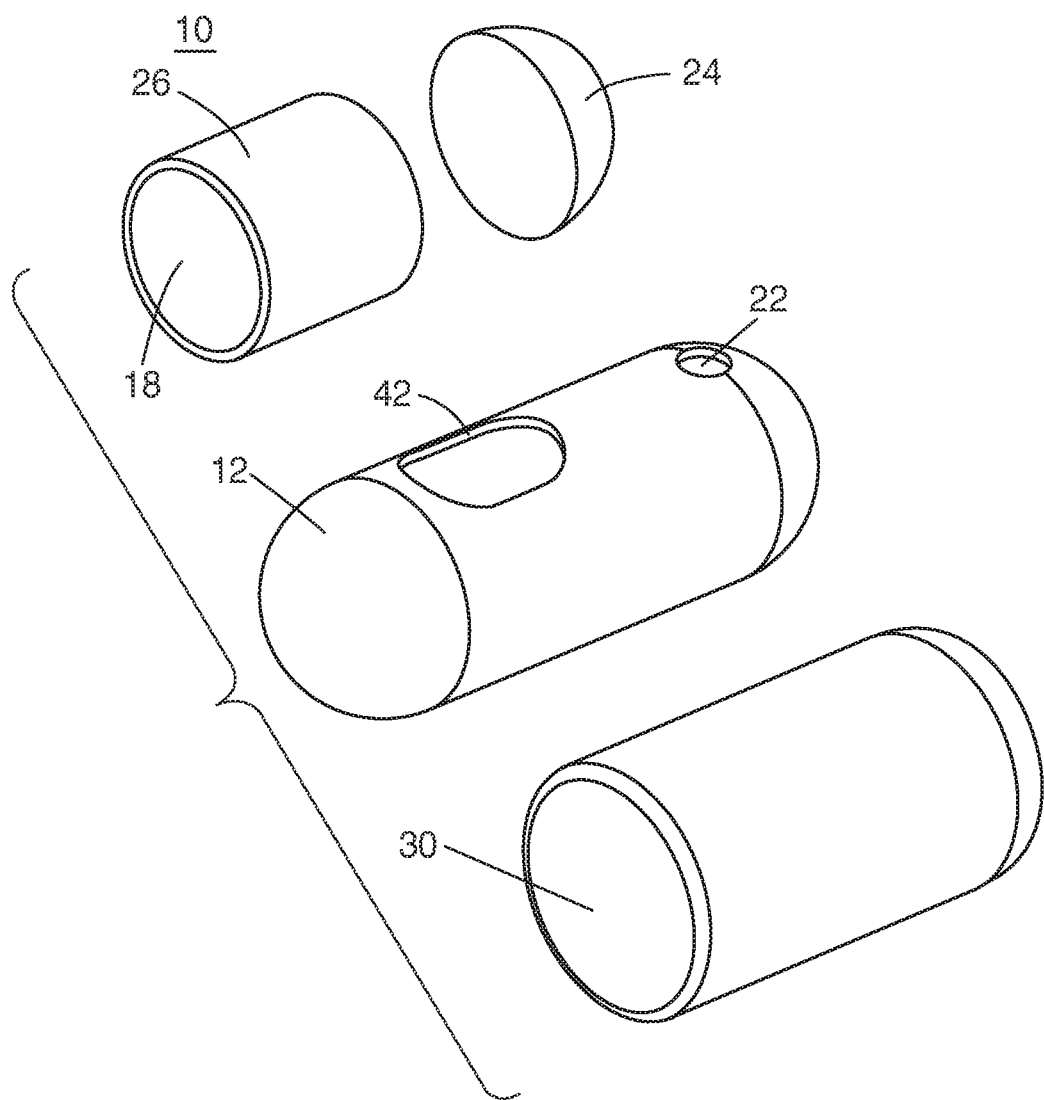
FIG. 6 illustrates in perspective view of an embodiment of the device comprising the disassembled elements thereof.
Figure 7:
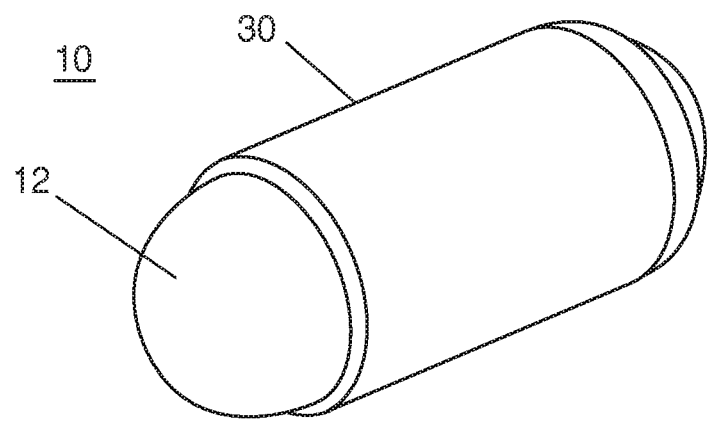
FIG. 7 illustrates in perspective view of an embodiment of the assembled device.

With reference to another embodiment shown in FIG. 6, the disassembled components of device 10 are shown in perspective view. Device 10 comprises body 12 with opening 42, hole 22, and piston 26 that is impervious to fluids, shaped like a cup with an internal volume that forms collecting member 18, actuator 24, and covering element 30 made from a moisture degradable material in the form of a hollow sleeve. FIG. 7 shows device 10 in perspective view fully assembled before swallowing with piston 26 and actuator 24 (not visible) inside body 12, and covering element 30 sealing opening 42 and hole 22 (not visible) from contact and/or fluid communication with the GI tract.

Figure 8:
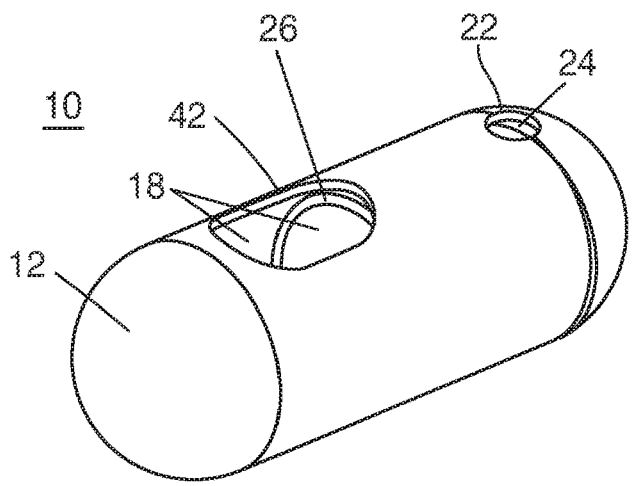
FIG. 8 illustrates a perspective view of an embodiment of the device prior to collecting any gastrointestinal samples.
Figure 9:
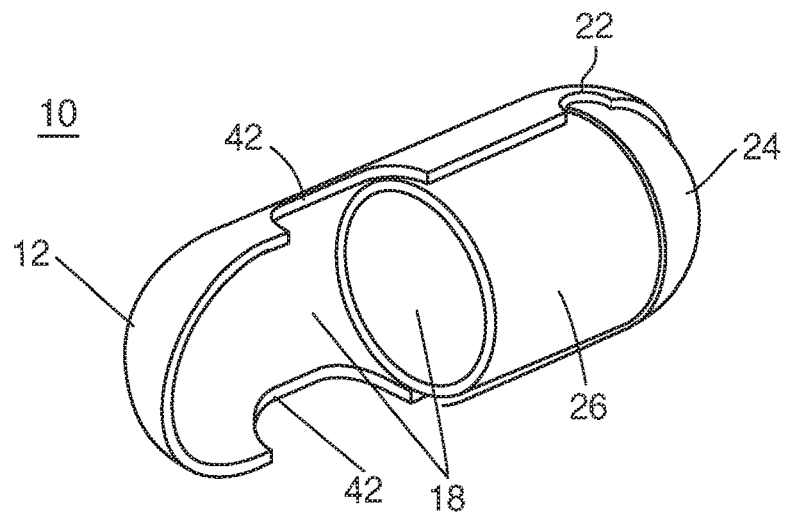
FIG. 9 illustrates a cut-away perspective view of an embodiment of the device prior to collecting any gastrointestinal samples.

After swallowing device 10, covering element 30 degrades at a predetermined time or pH in the GI tract, thereby exposing opening 42 and hole 22 to contact and/or fluid communication with the GI tract. FIG. 8 shows device 10 in perspective view fully assembled after degradation and elimination of covering element 30, but before collection of a gastrointestinal sample. Piston 26 and collecting member 18 are visible through opening 42 and actuator 24 are visible through hole 22. FIG. 9 shows device 10 in perspective view at this same time point with body 12 in section view to expose the components therein. The left half of body 12 and the inner cup-shaped volume of hollow piston 26 collectively form collecting member 18. There are two diametrically opposed openings 42 in order to allow trapped gas inside collecting member 18 to escape while gastrointestinal samples flow in through opening 42. Actuator 24 rests against the closed side of cup-shaped piston 26. At this stage, collecting member 18, which is the hollow volume inside body 12 and hollow piston 26 starts to collect gastrointestinal samples. Also at this stage, actuator 24, which is material that expands when wet, starts to push piston 26 axially due to the fluids in the GI tract flowing through hole 22 and wetting actuator 24.

Figure 10:
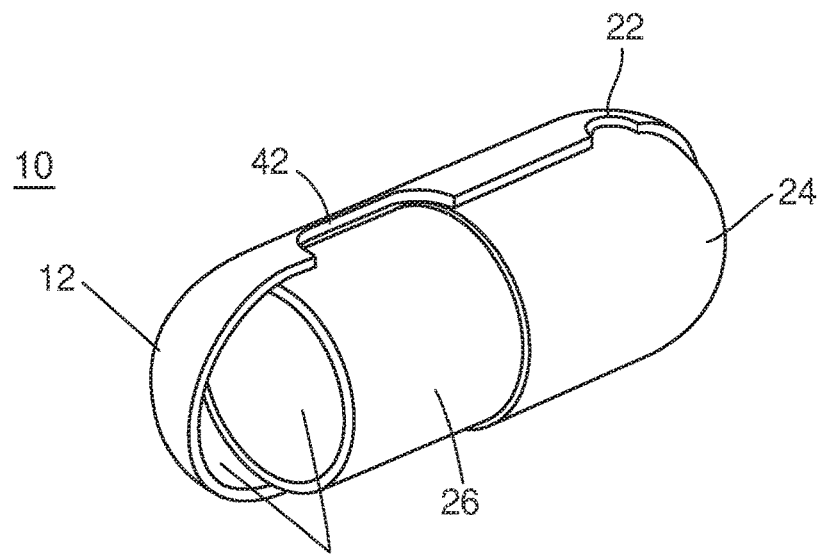
FIG. 10 illustrates a cut-away perspective view of an embodiment of the device after collecting gastrointestinal samples.

FIG. 10 shows device 10 in isometric view after the collection of a gastrointestinal sample with body 12 in section view to expose the components therein. Piston 26 has been displaced axially to the left side of body 12 by actuator 24, which is at its fully expanded state. The left half of body 12 and the inner cup-shaped volume of hollow piston 26 collectively form collecting member 18 that contains the collected gastrointestinal sample. Collecting member 18 is now sealed off from opening 42 by a seal formed between piston 26 and body 12. Device 10 is recovered from the GI tract in this state and the gastrointestinal sample within collecting member 18 is extracted from device 10 for further analysis.

In some embodiments, fluid that actuates actuator 24 enters through opening 42 once covering element 30 is removed so that actuator 24 only starts moving once a gastrointestinal sample has been collected by collecting member 18. For example, fluid entering opening 42 flows between piston 26 and the inner surface of body 12 to reach actuator 24. Actuator 24 is a material that expands when wet.

In some embodiments, collecting member 18 is a porous or water soluble material that fits at least partially within the hollow volume of piston 26 and causes the gastrointestinal samples to flow, wick or diffuse into collecting member 18.

In some embodiments, piston 26 is replaced with a porous collecting member 18 that has structural rigidity in the form of open-cell foam or dehydrated hydrogel. Gastrointestinal samples flow through opening 42 and wick into collecting member 18 due to capillary forces or diffusion in the direction of actuator 24. On the surface of collecting member 18 that is opposite actuator 24 is seal 38 that is forms a water-tight seal when pressed up against opening 42 from the inside of body 12. When gastrointestinal samples reach the distal edge of collecting member 18 and wet actuator 24, actuator 24 expands and pushes collecting member 18 and seal 38 forward against opening 42 in body 12, thereby sealing off collecting member 18 from further fluid communication with the gastrointestinal tract.

Figure 11:
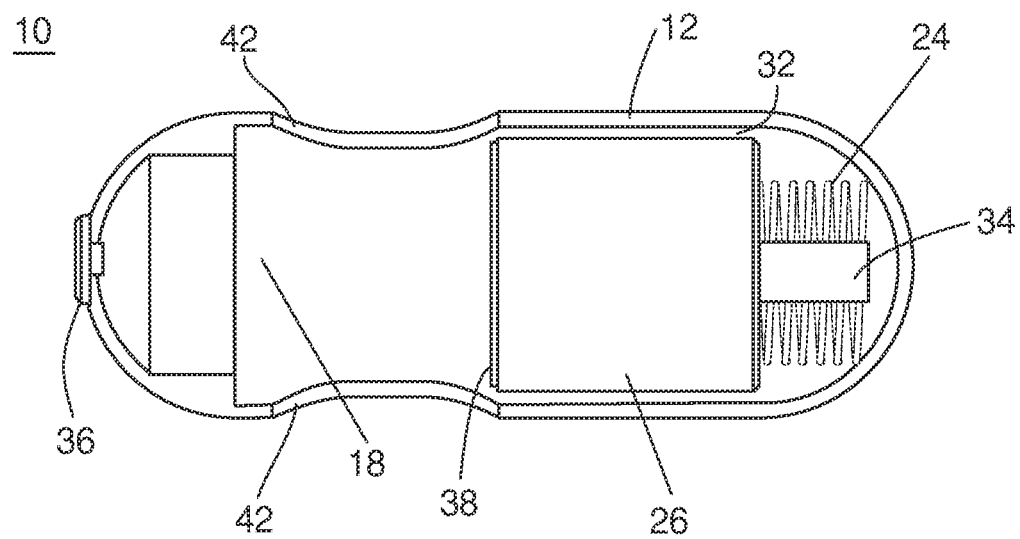
FIG. 11 illustrates a sectional view of an embodiment of the device prior to collecting any gastrointestinal samples.
Figure 12:
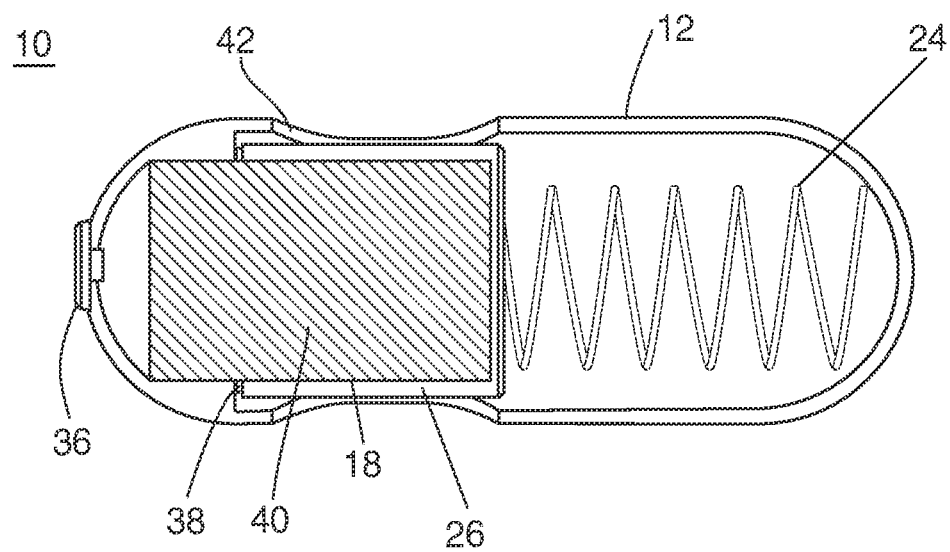
FIG. 12 illustrates a sectional view of an embodiment of the device after collecting gastrointestinal samples.

In some embodiments, shown in cross section view in FIG. 11, actuator 24 is a spring that is held in the compressed state by restraint 34 made from a moisture degradable material. In this manner, once covering element 30 is eliminated in the body, opening 42 is exposed to the fluids of the GI tract. Some of those fluids flow into collecting member 18, and some flow in space 32 around piston 26 to reach restraint 34. As shown in section view in FIG. 12, fluid from the GI tract degrades restraint 34, which in turn allows spring actuator 24 to expand, thereby pushing piston 26 axially to seat seal 38 against the surface of body 12, thereby sealing gastrointestinal sample 40 inside collecting member 18. In this manner, actuator 24 is activated only after collecting member 18 has collected gastrointestinal sample 40. In this embodiment, device 10 comprises cap 36 that is removed or punctured in order to access the collected gastrointestinal sample 40 after device 10 is eliminated from the body.

Figure 13:
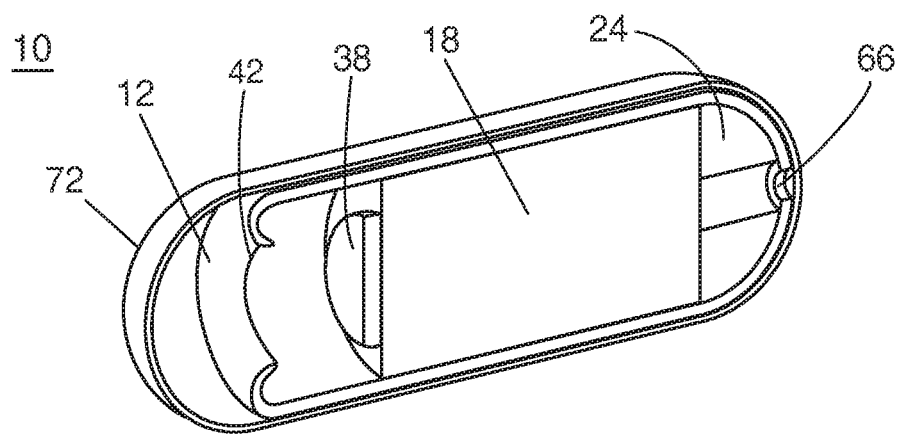
FIG. 13 illustrates a perspective view of an embodiment of the device prior to collection of gastrointestinal samples.
Figure 14:
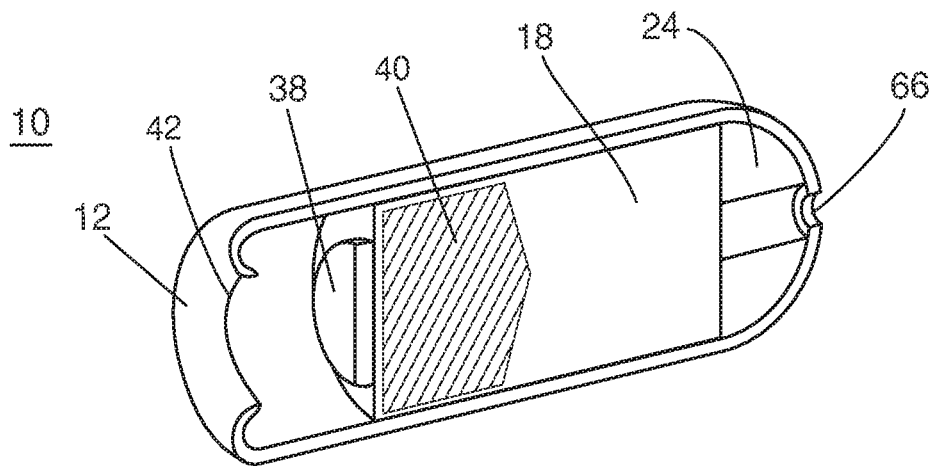
FIG. 14 illustrates a perspective view of an embodiment of the device during collecting gastrointestinal samples.
Figure 15:
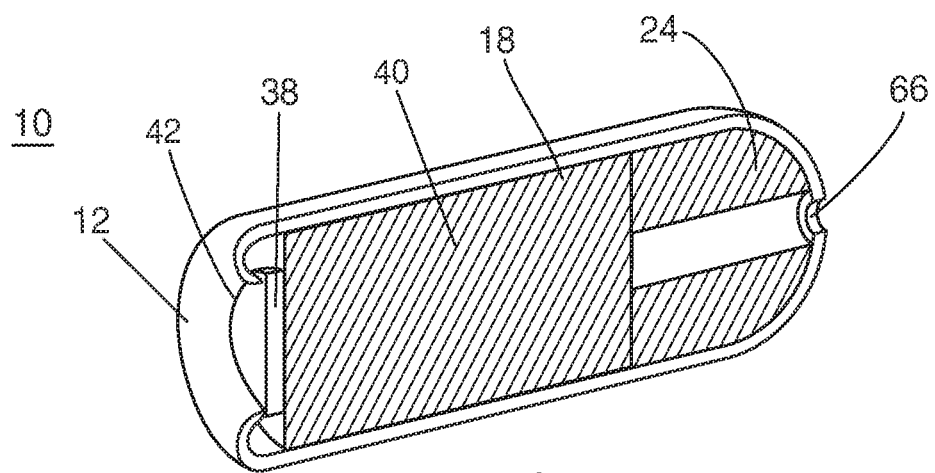
FIG. 15 illustrates a perspective sectional view of an embodiment of the device after collecting gastrointestinal samples.

In some embodiments and with reference to FIGS. 13, 14 and 15, all in perspective cross-section view, gastrointestinal fluids pass through porous collecting member 18 and wet actuator 24. Actuator 24 expands when wet to apply linear pressure on sealing element 38. In FIG. 13, device 10 is still contained within capsule 72 which is a sealed capsule whose shell is made from a moisture degradable material such as HPMC and optionally comprises an enteric degradable material acting as covering element 30, for collection of samples in the intestines or colon.

In some embodiments, covering element 30 directly covers opening 42 and prevents gastrointestinal samples from flowing into collecting member 18. In this embodiment, there is no need for capsule 72 if body 12 is smooth enough to be swallowed directly.

In both embodiments above, gastrointestinal fluids are not yet in fluid communication with collecting member 18. In FIG. 14, covering element 30 has degraded and gastrointestinal samples 40 have started to enter collecting member 18 through opening 42 in body 12 and around seal 38 into collecting member 18. Gas contained in device 10 is vented through vent 66 as gastrointestinal samples 40 enter collecting member 18. In FIG. 15, gastrointestinal samples 40 have advanced through collecting member 18 into actuator 24, which is in fluid communication with collecting member 18. Actuator 24 expands when wet, and therefore pushes collecting member 18 towards opening 42, and eventually seal 38 is pressed against the rim of opening 42 thereby sealing collecting member 18 and preventing further sample collection or cross contamination. Actuator 24, when wet, exerts a residual and continuous linear force against seal 38, thereby maintaining the seal throughout the passage of device 10 through the GI tract. In this embodiment the force on seal 38 is in the same direction as the direction of expansion of actuator 24. Examples of materials for collecting member 18 comprise acetate foam and other rigid non-expansive open-cell foams that can transmit linear compressive force from actuator 24 to seal 38. Examples of materials for actuator 24 comprise dehydrated natural or synthetic sponges or dehydrated superabsorbent materials such as hydrogels, sodium polyacrylate, polyacrylamide or starches at various levels of crosslinking.

In some embodiments, a wick is placed in opening 42 that helps bring the gastrointestinal samples closer to collecting member 18, at which point fluid communication is established between collecting member 18 and the fluids in the gastrointestinal tract. The wick is then pushed out of opening 42 when actuator 24 advances collecting member 18.

In some embodiments, the degradation of a first moisture degradable restraint allows actuator 24 to move collecting member 18 to a position relative to opening 42 that enables fluid communication between collecting member 18 and the GI tract. Once gastrointestinal samples 40 have been collect in collecting member 18, the fluid from the collected gastrointestinal samples 40 degrades the second moisture degradable restraint and allows actuator 24 to move collecting member 18 to a position relative to opening 42 that prevents further fluid communication between collecting member 18 and the GI tract. In this manner, a single actuator 24 can move collecting member 18 into the two discrete positions of sample collection and sample isolation using a double trigger moisture degradable restraint mechanism.

Figure 16:
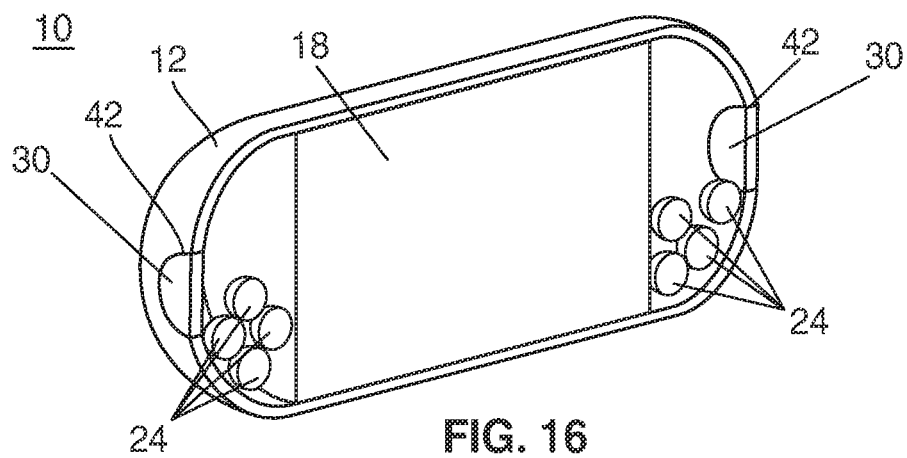
FIG. 16 illustrates a perspective view of an embodiment of the device prior to collection of gastrointestinal samples.
Figure 17:
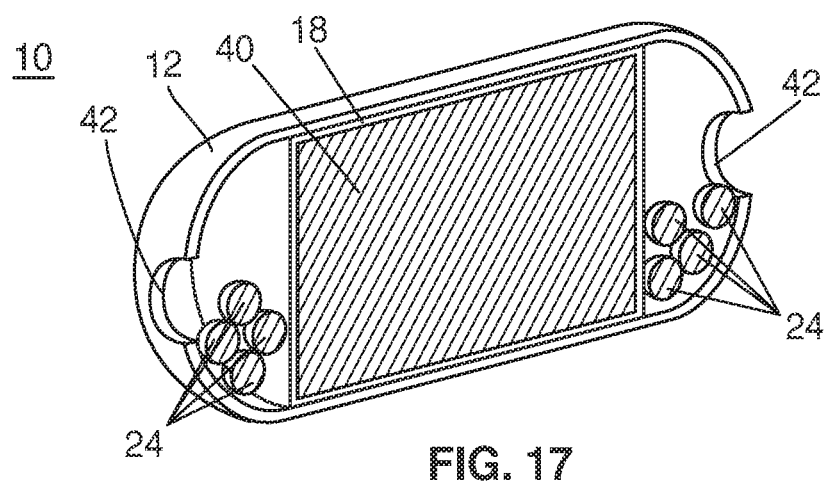
FIG. 17 illustrates a perspective view of an embodiment of the device during collecting gastrointestinal samples.
Figure 18:
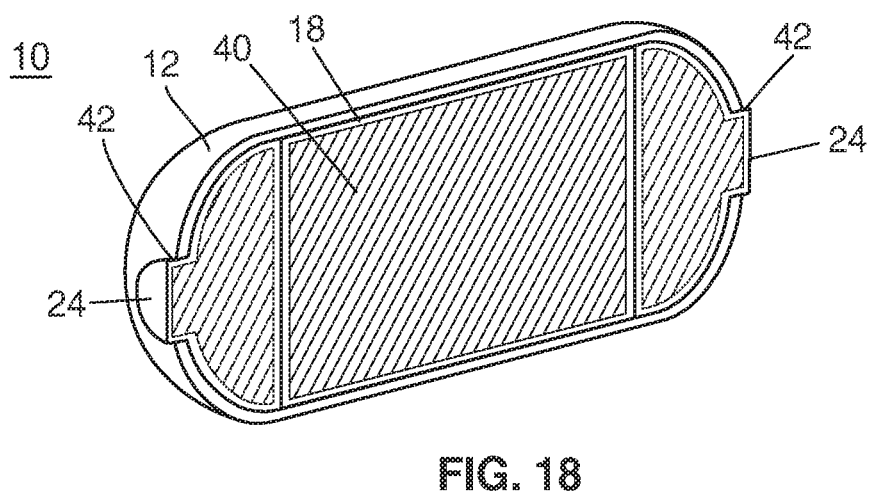
FIG. 18 illustrates a perspective sectional view of an embodiment of the device after collecting gastrointestinal samples.

In some embodiments and with reference to FIGS. 16, 17 and 18, all in perspective cross-section view, gastrointestinal fluids flow through opening 42 and into porous collecting member 18 and wet one or more elements of actuator 24. Elements of actuator 24 expand when wet to create a plug blocking opening 42. In FIG. 16, opening 42 of body 12 on device 10 are still covered by covering element 30, and therefore gastrointestinal fluids are not yet in fluid communication with collecting member 18. In FIG. 17, covering elements 30 have degraded and gastrointestinal fluids 40 have entered through opening 42 into collecting member 18 and also wet elements of actuator 24. Gas contained in device 10 is vented through one or both opening 42 as gastrointestinal samples 40 enter collecting member 18 and displace the gas contained therein. In FIG. 18, gastrointestinal samples 40 have caused significant swelling of volumetric expansion of the elements of actuator 24, thereby forming a dense gel plug that seals opening 42 and prevents further sample collection or cross contamination. In this embodiment, collecting member 18 does not move during the sample collection and capsule sealing process. Examples of materials for collecting member 18 comprise a gas, acetate foam, and cotton. Examples of materials for actuator 24 comprise dehydrated superabsorbent materials such as hydrogels, sodium polyacrylate, polyacrylamide and starches at various levels of crosslinking. The time for expansion or swelling of the particles of actuator 24 is between 1 and 60 minutes to allow for sufficient time for gastrointestinal samples 40 to flow into collecting member 18 before swelling actuator 24 to seal opening 42. In this embodiment, the fluids of gastrointestinal samples provide the moisture that swells a superabsorbent material into a sealing gel, but only after the gastrointestinal samples have filled collecting member 18. In this embodiment, the hydrated plug formed by actuator 24 is sufficiently dense to limit bacterial migration or diffusion of biomolecules through the gel to a rate of less than about 0.1 mm per hour.

In some embodiments, and with reference to FIGS. 16 through 18, device 10 comprises a vent which is hydrophobic or comprises a one-way valve and does not let gastrointestinal samples inside body 12, but rather lets trapped gas vent out as collecting member 18 fills with gastrointestinal fluids. In this embodiment, it is necessary to only have one opening 42 for the entrance of the gastrointestinal samples.

In some embodiments, and with reference to FIGS. 16 through 18, device 10 has only a single opening 42 and a covering element 30 into which gastrointestinal samples 40 flow and out of which trapped gases escape. This embodiment relies on the unexpected observation by the inventor that gastrointestinal fluids, especially in the small intestine, have been emulsified by bile acids, which act like a detergent. Therefore, the gastrointestinal samples in the small intestine have extremely very low surface energy and can wick into very small openings, while allowing for trapped gas to be released from that same opening. The bubbles of the released trapped gas have no problem breaking the surface tension of the low surface energy liquid in the small intestines.

In some embodiments, and with reference to FIGS. 16 through 18, device 10 has opening 42 adjacent to a gas vent and actuator 24 swells to cover both opening 42 and the gas vent.

In some embodiments, and with reference to FIGS. 16 through 18, the material of actuator 24 that expands when wet also functions as collecting member 18.

In some embodiments, device 10 comprises a plurality of collecting members 18 separately enclosed with separate opening 42, seal 38 and/or actuator 24. Each opening 42 of collecting member 18 is covered by a distinct covering element 30. Each covering element 30 degrades at a preset pH or dissolution time. In this manner, one device 30 can collect multiple discrete samples of gastrointestinal fluids from different regions of the GI tract without cross talk or cross contamination between the samples.

In some embodiments, covering element 30 is made from a moisture degradable material that is pH sensitive. Covering element 30 uncovers a first set of openings (e.g., similar to opening 42 and/or 22) at a pH of 5 or less, leading to a stomach sampling location. Covering element 30 uncovers a second set of openings (e.g., similar to opening 42 and/or 22) at a pH of 5.5 to 6.5, leading to a proximal small intestine sampling location. Covering element 30 uncovers a third set of opening (e.g., similar to opening 42 and 22) at a pH of 6.5 to 7.5, leading to a distal small intestine sampling location. Covering element 30 uncovers a fourth set of opening (e.g., similar to opening 42 and 22) at a pH of 6 to 7 after a set time delay, leading to a colon sampling location. Multiple layers of moisture degradable materials can be designed into covering element 30 so that the final layer degrades at a set time after a series of pH levels is encountered in the layers, leading to anatomically distinct and predictable sampling locations.

The pH of the human intestinal tract has been extensively studied. Typical results are shown in Table 1 below.

TABLE 1 pH of the human GI tract. Ref: Gut, 1988, 29, 1035-1041.

| Site | Mean pH (or range) | Standard deviation | Time spent in each region |
|---|---|---|---|
| Stomach | (1.5-3.5) | n/a | Up to 3 hours |
| Duodenum | (5.0-6.0) | n/a | Up to 1 hour |
| Jejunum | 6.6 | 0.5 | Up to 1 hour |
| Ileum | 7.5 | 0.5 | Up to 1 hour |
| Right colon | 6.4 | 0.6 | Up to 6 hours |
| Mid colon | 6.6 | 0.8 | Up to 8 hours |
| Left colon | 7.0 | 0.7 | Up to 12 hours |

An enteric degradable material by its nature degrades above a specific pH level. By way of example, an enteric coating element design to dissolve at pH 7 will likely enable sampling GI fluids at a point between the jejunum and ileum where the pH level transitions from 6.6 to 7.5.

The vast majority of the gut bacteria reside in the colon, and more specifically the bacteria are most active in the right colon, otherwise referred to as the cecum or ascending colon. Therefore, a prime target for sample collection is the right colon which is at pH 6.4+/−0.6. A major challenge, therefore, is to create a covering element, or set of covering elements, that enable sampling in the right colon. An enteric coating that degrades at pH 6.4 or higher targeting the right colon will degrade in the ileum and sample the fluids in the ileum instead, before reaching the right colon after already having ingested the ileum sample. This is especially true since pH dependent dissolution rates of enteric coatings are significantly higher above their target pH level. An enteric coating that is designed to dissolve at a pH higher than 7.5 may still survive the ileum, in which case it will not dissolve in the right colon where the pH is significantly lower than the ileum. Such a capsule will therefore exit the GI tract with covering 30 intact and without having collected any GI sample.

In one embodiment, an external covering element of a device is designed to degrade at a pH level of 6.7 (+/−0.3) or higher, such that the covering element will dissolve in the distal small intestines and thereby expose an internal covering element. The internal covering element is designed to degrade at a pH of 6.7 (+/−0.3) or lower. This internal covering element will stay intact in the distal small intestines until device 10 reaches the right colon where the pH drops to below 6.7. Once in the right colon, the internal covering element will dissolve and enable the sample collection process. This embodiment is referred to as "inverse pH" covering elements where the outer covering element dissolves at or above a target pH and the inner covering elements dissolves at or below a target pH. The target pH can be the same or different for the external and internal covering elements, thus targeting any region of the GI tract that has a drop in pH relative to the more proximal adjacent region, which itself is higher than the pH of the stomach.

In some embodiments, a capsule or device containing an active agent targeting release of that active agent in the right colon comprises an external covering element that degrades at a pH level of 6.7 (+/−0.3) or higher, such that the covering element will dissolve in the distal small intestines and thereby expose an internal covering element. The internal covering element is designed to degrade at a pH of 6.7 (+/−0.3) or lower, so that this internal layer will stay intact in the distal small intestines until the capsule reaches the right colon where the pH drops to below 6.7. Once in the right colon, the internal covering element will dissolve or become permeable, thereby enabling the release of the active agent into the right colon.

By way of example, materials that dissolve above a minimal pH level and are therefore appropriate for the external covering element comprise anionic acrylic polymers with methacrylic acid as a functional group such as Eudragit L, Eudragit S or mixtures thereof (Evonik Darmstadt Germany). By way of example, materials that dissolve below a maximum pH level and are therefore appropriate for the internal covering element comprise cationic polymer with dimethylaminoethyl methacrylate as a functional group such as Eudragit E (Evonik Darmstadt Germany) or modifications thereof. By way of example, in this embodiment wherein sampling device 10 or a capsule containing an active agent intended for colonic delivery or colonic release, the capsule is coated first with an internal covering element of a cationic polymer with dimethylaminoethyl methacrylate as a functional group and then coated with an external covering element of anionic acrylic polymers with methacrylic acid as a functional group.

In some embodiments, the devices are provided as part of a kit that includes a number of different capsules, each of which is designed to sample a different region of the GI tract. The capsules are swallowed at the same time and collected separately. By way of example, a kit is provided with a stomach targeting, a small intestine targeting and a colon targeting devices. The patient swallows all three capsules and collects them separately in one or adjacent bowel movements. An advantage with the separate device approach is that for a given volume of collected sample, each of the three device can be one third the volume relative a single three-chambered device, thereby minimizing the risk of capsule retention and difficulty of swallowing the device.

In some embodiments, a set of devices is coated with a moisture or enteric degradable covering element of different thicknesses intended to degrade at different time points to target different regions of the GI tract. Transit time through the GI tract is highly variable among individuals. For example, it could take up to 8 hours after gastric emptying for a capsule to arrive at the right, proximal or ascending colon. The pH of the GI tract is also highly variable among individuals. The proximal or ascending colon has a pH of 6.4 with a standard deviation of 0.6 pH units. To target the gastrointestinal sampling in the proximal or ascending colon based on a specific transit time or specific pH range alone would be difficult without using the dual coating inverse pH technique described above. By way of example, a subject can be provided with three device capsules each coated with a pH sensitive polymer covering element of different thicknesses that all degrade at pH 5.5 or higher, thereby starting to degrade in the small intestine after gastric emptying. The thickness of the covering element can determine whether to covering element degrades over 1, 3 or 6 hours for the three devices, thereby assuring that at least one device 10 units obtains a sample in the proximal or ascending colon. Example materials for the covering element comprise copolymers derived from esters of acrylic and methacrylic acid dissolvable at a pH of 5.5 or higher at coating density of 5 to 200 milligrams per centimeter squared of body surface area, or preferably 10 to 100 milligrams per centimeter squared of body surface area. A coating density of 5-10 milligrams per centimeter squared of body surface area will dissolve in around 1 hour whereas a coating density of 100-200 milligrams per centimeter squared of body surface area will dissolve in around 8 hours or so, thereby allowing universal targeting of the proximal or ascending colon with 2 or at most 3 devices.

In another embodiment, individual devices are connected to one another with a string or similar flexible connection element, to ensure that all devices are expelled in the same bowel movement to make collection of multiple devices easier. By way of example, beads of dehydrated sodium polyacrylate are strung along a thread. Each bead is coated with a different time-sensitive or pH-sensitive coating element. The beads get exposed to gastrointestinal samples at different regions of the GI tract depending on when and where the coating element surrounding each bead becomes degraded. Exposed beads imbibe the fluid gastrointestinal samples and swell. Diffusion through the sodium acrylate is sufficiently slow that downstream exposure to microbes or small molecules will not contaminate the sample collected in the inner sections of the sodium acrylate bead. The swollen beads exit the GI tract together as a chain of beads and the samples within each are recovered from the hydrated sodium acrylate gel for further analysis.

In some embodiments, individual body 12 units are thin-walled hollow structures whose internal volume comprises individual collecting member 18 units. Each body 12 is collapsed and compacted to fit empty inside capsule 72. After degradation of covering element 30, the firstly exposed collecting member 18 fills with GI samples. Filling of the first collecting member 18 with GI samples triggers the opening of opening 42 of a second connected body 12. Filling of the second collecting member 18 with GI samples triggers the opening of opening 42 of a third connected body 12, etc. In this manner, a set of collapsed yet connected body 12 units can fit compactly inside capsule 72 sample multiple regions of the GI tract, while still being recovered as a linked unit from the stool.

Figure 19:
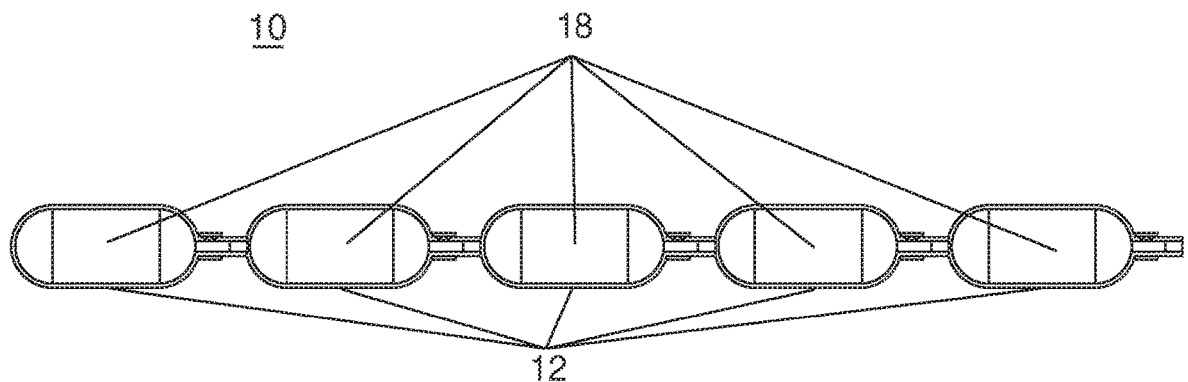
FIG. 19 illustrates a sectional view of an embodiment of the device configured as a segmented series of discrete collecting members.

In some embodiments, illustrated in a cut away side view in FIG. 19, individual body 12 units are linked together in a daisy chain or sausage link format. In this embodiment, each collecting member 18 contained within each body 12 an collect a discrete sample from the GI tract. This embodiment allows for linking many such body 12 units together, thereby enabling large volumes of samples to be collected despite the maximal diameter of a collecting member of about 2 mm, 3 mm, 4 mm, 5 mm, 6 mm or 7 mm in order minimize the likelihood of device retention in the GI tract. Furthermore, the thin links between body 12 units allow for full articulation of collecting members in the axial direction relative to one another in order to more easily navigate the small intestine lumen which has sharp curves. The radius of curvature of the small intestine can be as small as 3 cm in a hair pin turn. Therefore, in order to navigate the curvature of the small intestine and minimize risk of retention in the GI tract, each segment of body 12 should be no longer than about 3 cm, and a set of linked body 12 units should be able to conform to a hair pin turn with a 3 cm radius with a radial force of about 10 grams or less, preferably without kinking.

Figure 34:
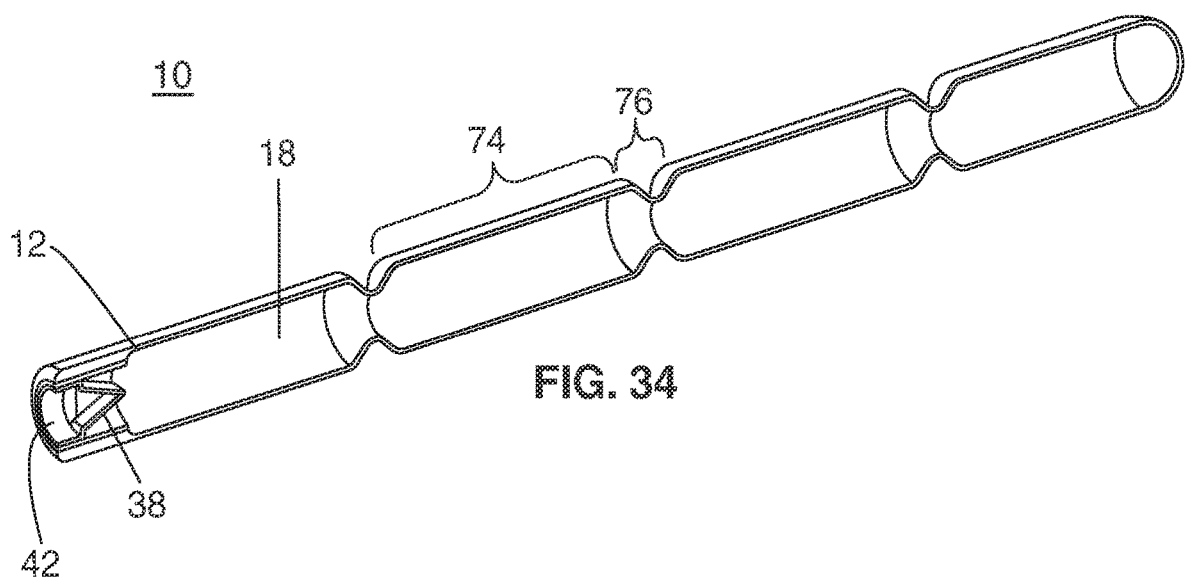
FIG. 34 illustrates a sectional perspective view of an embodiment of the device configured as a single segmented collecting member.

In some embodiments, illustrated in FIG. 34, and in order to enable axial articulation into a radius of curvature of the linked collecting members 18 of about 3 cm or less, the length range of segment 74 of collecting member 18 at its maximum diameter is about 1-30 mm. The maximum diameter of a narrow section 76 linking segments of the collecting member 18 is about 75% or less of the maximum diameter of the collecting member. The length range of a segment of narrow section 76 collecting member 18 at its smallest diameter is about 1-5 mm. Furthermore, the radius of curvature of body 12 in the region of the transition from maximum diameter segment 74 to narrow section 76 is about 1 mm or greater in order to avoid any sharp edges that can damage the delicate intestinal mucosa layer.

In some embodiments, there is no element that acts to expands body 12 axially during the unwinding, unfolding or sampling process.

In some embodiments, the total length of tube-shaped body 12 does not increase in the axial direction during the sample collection process. Rather, the flow of gastrointestinal samples flow into collecting member 18 is due to a radial expansion of the collapsed lumen of tube-shaped and fixed-length body 12.

In some embodiments, individual body 12 units are linked by elongated tube or string elements connected to a common point in a manifold, spoke or star configuration.

In further embodiments, the length of the elongated tube or string elements that act as spokes or tubes off of a manifold are of different lengths such that the cluster of body 12 units can arranged themselves linearly in single file during the passage through the small intestine.

In further embodiments, the common connection point of the spoke elements comprises discrete sample openings, seals and/or valves connected to individual collecting members 18 units.

Figure 20:
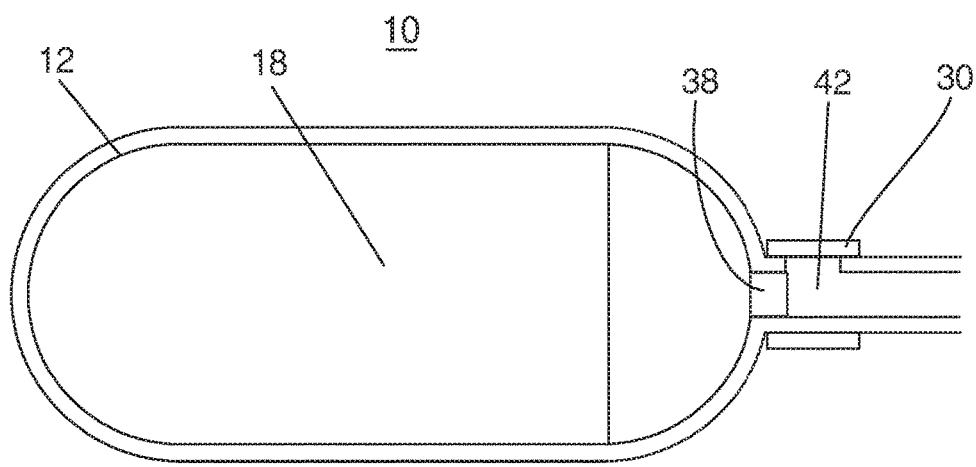
FIG. 20 illustrates an enlarged sectional view of one of the collecting members of the embodiment shown in FIG. 19.

As illustrated in FIG. 20 in a magnified cut away side view of one collecting member 18, opening 42 is covered by covering element 30. Seal 38 acts as a one-way valve to prevent collected samples in collecting member 18 from exposure to cross contamination or leakage during the rest of the transit through the GI tract. In this manner, a negative pressure differential inside collecting member 18 relative to the GI tract, for example by radial expansion of an elastically collapsed or evacuated collecting member 12, or alternatively capillary pressure alone, drives fluids into collecting member 18. The collected GI samples cannot flow back out via the one-way valve. Examples of one-way valves comprise flap valve, lay flat tubing, duck bill valve, umbrella valve, ball valve, dome valve, Belleville valve, and cross-slit valve.

In some embodiments, the rate of sampling is controlled by the balance of two forces. The first force is the force of radial expansion of the compressed tube shaped body 12, which creates a pressure differential that drives fluid through sampling opening 42 into collecting member 18. The second opposing force is the resistance to flow through the one way valve in the forward flow direction. One way valves are generally biased closed to prevent flow in the backward direction when there is no pressure differential across the valve. The forward pressure required to open the valve is called the cracking pressure. The cracking pressure is the first component of the resistance to flow. The second component of the resistance to flow is the size of the opening(s) of the one way valve. The third component of the resistance to flow is the force of the sealing element acting to close the one way valve. All three components act together to create the resistance to forward flow in a one way valve.

In some embodiments of device 10, the cracking pressure required to open the one way valve and generate flow in the forward direction into collecting member 18 is in the range of 0.03 to 15 pounds per square inch, or preferably 0.06 to 5 pounds per square inch. This cracking pressure prevents collected samples from flowing back out of collecting member 18 when there is no pressure differential between the fluids in collecting member 18 and the outside environment. A cracking pressure that is higher than the stated range will not allow for flow of samples into collecting member 18. A cracking pressure that is lower than the stated range will cause leakage of the collected samples due to peristaltic pressure waves in the GI tract, or by handling of the device outside the body, and then subsequent cross-contamination by any newly ingested samples.

In some embodiments, the maximal outward radial pressure exerted by a collapsed tube-shaped body 12 is in the range of 10 to 150 grams-force per cm length of body 12, or preferably 20 to 100 grams-force per cm length of body 12. By way of example, for collecting member 18 with a volume of 0.5 ml, the flow rate of fluid through the one way valve when exposed to a pressure differential created by the outward radial expansion of body 12 and balanced by the counter force of the resistance to flow through the one way valve, as described above, is in the range of 1 microliters of fluid per minute to 500 microliters per minute. This flow rate enables device 10 to sample for a time range of 1 minute to 8 hours. Maximal expansive forces above the ranges stated, or valves that enable flow rates above the ranges stated, will cause collecting member 18 to fill in less than 1 minute, and thereby increase the likelihood of sampling gas bubbles present around device 10. Expansive forces below the ranges stated will not crack open the one-way valve, leading to no sample collection. Therefore a delicate balance of all the factors above is required to properly sample the GI tract over the desired time period. In some embodiments, the passageway between opening 42 and collecting member 18 is normally open. After sufficient sample has been collected, after sufficient sampling time has passed, or after a pH change is detected which indicates movement of device towards a new region of the GI tract, a spring loaded mechanism closes the passageway and seals gastrointestinal samples inside collecting member 18.

In some embodiments, covering element 30 is a collar that keeps opening 42 sealed until the desired region of the GI tract is reached based on hydration time or pH levels of the surrounding fluids that act to degrade covering element 30.

Figure 40:
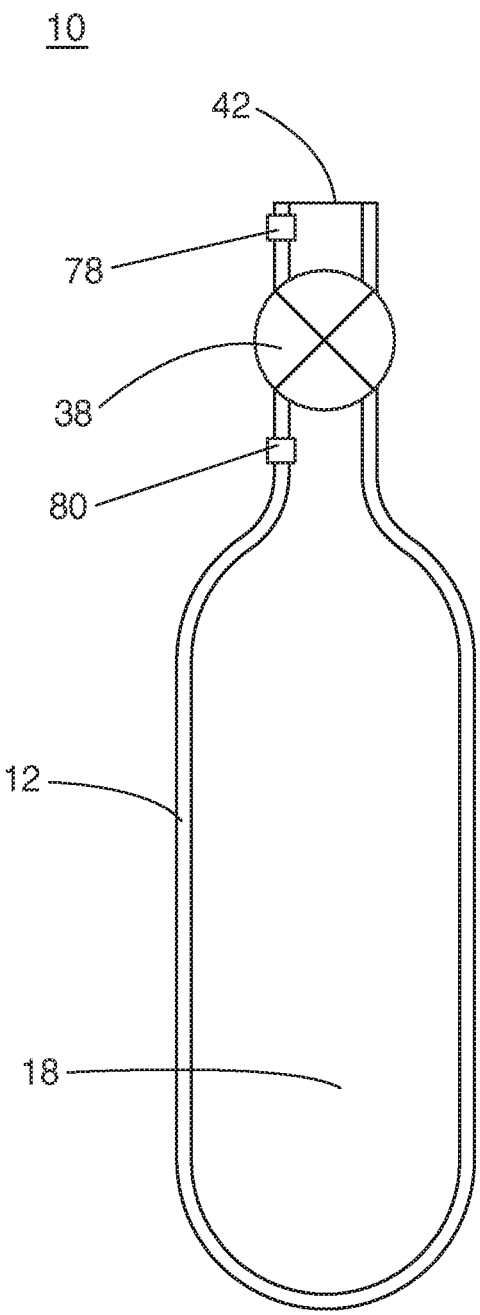
FIG. 40 illustrates an embodiment of the device with an active valve, pH sensor and flow sensor.

In an embodiment illustrated in a sectional view in FIG. 40, the passage of gastrointestinal samples through opening 42 into collecting member 18 is gated by seal 38. Seal 38 in this embodiment is an actively controlled valve. Valve seal 38 is normally closed and actively opened at a predetermined rate to enable collection of gastrointestinal samples. By way of example, valve seal 38 opens for several seconds every hour so that at least eight distinct regions of the GI tract are sampled during an 8 hour sampling window after swallowing device 10.

In another embodiment and with reference to FIG. 40, valve seal 38 is controlled by pH sensor 78. During transit of device 10 through the GI tract, when specific pH levels, or the rates of change of pH levels, are sensed by pH sensor 78 in a predicted and pre-programed sequence corresponding to ascending pH though the small intestine and then descending pH in the right colon, pH sensor 78 triggers the momentary opening of normally-closed valve seal 38 to enable collection of gastrointestinal samples. In this manner, device 10 collects gastrointestinal samples at multiple pH levels corresponding to multiple regions along the GI tract. Example pH levels that can be programmed in device 10 to ensure that all relevant GI regions are targeted for sample collection are described in Tables 1 and 4.

The maximal volume of body 12, and hence collecting member 18, is highly constrained by body 12 needing to fit inside capsule 72 of size 000 or smaller, and that body 12 does not block or become retained in the GI tract when body 12 is in an expanded state outside capsule 72. Therefore, given that the maximum volume of collecting member 18 is limited, it is important to maximize the amount of informative liquid gastrointestinal samples collected inside collecting member 18. Collection of gas samples takes up precious volume inside collecting member 18 and is not as informative as liquid samples that contain a much higher density of active organisms and biomolecules compared to gas samples that contain only volatile compounds. In some embodiments and with reference to FIG. 40, valve seal 38 is also controlled by flow sensor 80. In a situation where valve seal 38 is open and liquid gastrointestinal samples are flowing through opening 42 into collecting member 18, in-line flow sensor 80 senses such a flow and keeps valve seal 38 open until sufficient volume of samples has been collected for that region of the GI tract. However, in a situation where valve seal 38 is open and gas is flowing through opening 42 into collecting member 18, in-line flow sensor 80 will not sense liquid flow and will therefore send a signal to close valve seal 38 to prevent gas samples from taking up the collection volume inside collecting member 18. After a sufficient time delay, or when a separate liquid sensor on or near opening 42 senses the presence of liquid samples, valve seal 38 will open again to continue the sampling process. Flow sensor 80 will again confirm the influx of liquid samples into collecting member 18 and will send a signal to keep valve seal 38 open until sufficient volume of liquid gastrointestinal sample has been collected for that region of the GI tract.

In some embodiments, pH sensor 78 and flow sensor 80 work together to ensure that a pre-specific volume of liquid gastrointestinal samples from a pre-specified pH range has been collected inside collecting member 18.

In some embodiments, valve seal 38 controls the flow of trapped gas inside collecting member 18 out of body 12, thereby allowing gastrointestinal samples to flow into collecting member 18 through a separate, normally open sampling opening.

In some embodiments, body 12 is elastically collapsed and allowed to re-expand, drawing in gastrointestinal samples in collecting member 18 when valve seal 38 is open.

In some embodiments, body 12 is a hollow tube 5 mm to 50 cm in length and 1 mm to 8 mm in diameter in which gastrointestinal samples are stored as a linear array inside collecting member 18 which is formed by the lumen of body 12.

In some embodiments, after gastrointestinal samples are allowed past opening 42 by valve seal 38, a manifold and/or additional valves direct gastrointestinal samples into separate collecting members 18. In this manner, one valve seal 38 can control the sampling of different regions of the GI tract while keep the collected gastrointestinal samples in discrete collecting members to avoid cross contamination.

In some embodiments, body 12 units are thin-walled hollow structures that are collapsed and stacked empty inside capsule 72 for swallowing in a compact manner Each collecting member 18 is connected to opening 42 that is sealed with a different moisture-degradable, enteric degradable, time degradable or colonic targeting material covering element 30. After degradation of the discrete covering elements 30, each collecting member 18 fills with GI samples corresponding to desired sampling locations in the GI tract as determined by the degradation characteristics of the moisture-degradable, enteric degradable, time degradable or colonic targeting covering element 30. In this manner, a set of collapsed yet connected body 12 units can fit compactly inside a single capsule 72 and discretely sample multiple regions of the GI tract, while still being recovered as a linked unit from the toilet.

In some embodiments, device 10 comprises a retrieval tail 2 cm in length or longer that unfurls in the GI tract and facilitates identification and retrieval of device 10 in the toilet.

Figure 21:
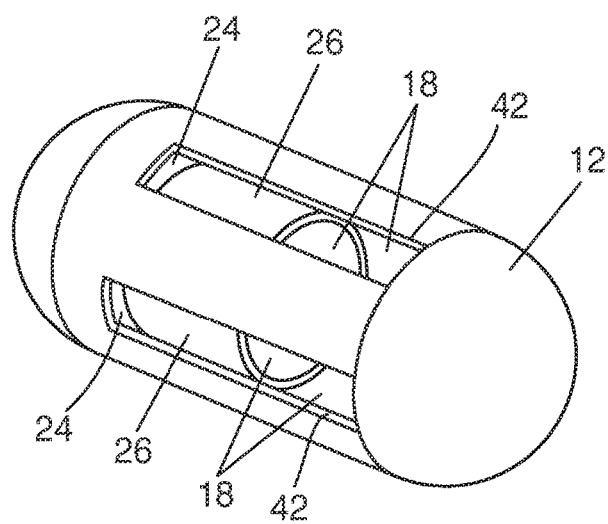
FIG. 21 illustrates a perspective view of a multiple collection element embodiment of the device prior to collecting any gastrointestinal samples.

In an embodiment shown in FIG. 21, device 10 comprises more than one collecting member 18 distributed in a radial arrangement inside body 12. Each opening 42 is covered with a covering element 30 (not shown) that opens at a different time or a different pH range in the GI tract. In this fashion, device 10 collects a discrete gastrointestinal sample from the GI tract into each collecting member 18.

Figure 22:
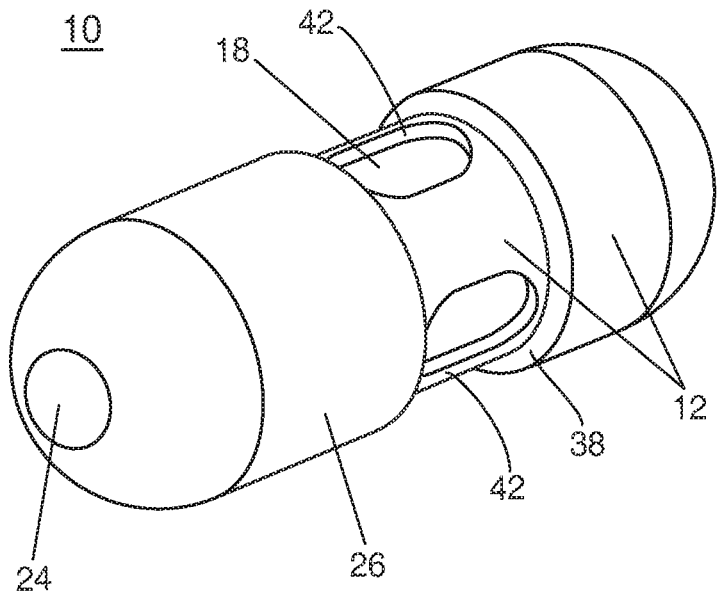
FIG. 22 illustrates a perspective view of an embodiment of the device prior to collection of gastrointestinal samples.

With reference to an embodiment shown in FIG. 22 in a perspective view, device 10 has been released from a covering element that covered opening 42 and now device 10 is in the desired position for sampling the GI tract. Collecting member 18 is a cylindrical shaped porous or water soluble element which is in fluid communication with the lumen of the GI tract through opening 42. After collecting gastrointestinal samples, actuator 24 moves external piston 26 over body 12 to close off opening 42. At the end of this translation, external piston 26 rests against seal 38 to seal gastrointestinal samples inside collecting member 18.

Figure 23:
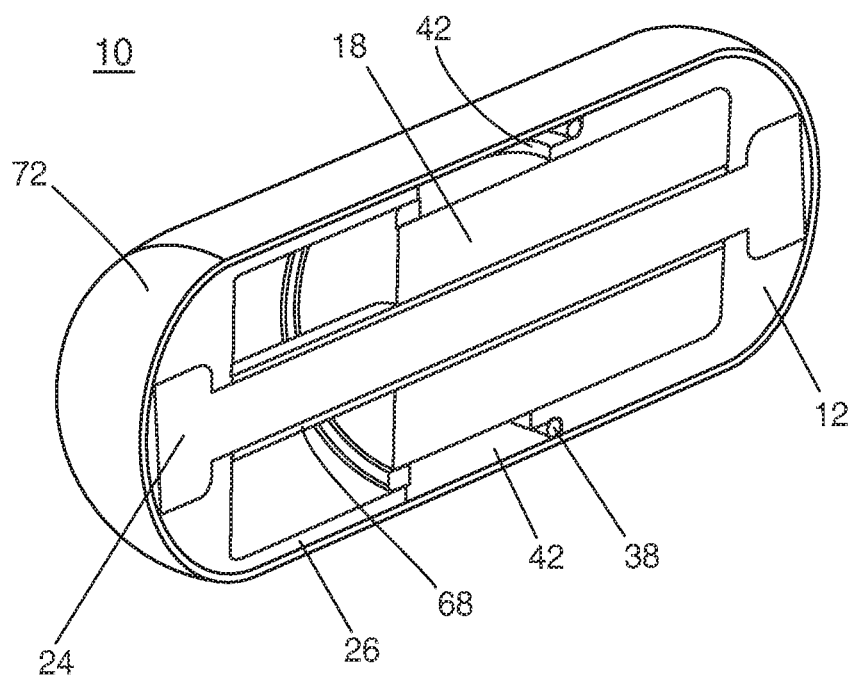
FIG. 23 illustrates a perspective sectional view of an embodiment of the device prior to collection of gastrointestinal samples.

As illustrated in FIG. 23 in a sectional perspective view, device 10 is shown before reaching the desired sampling location. Device 10 is within capsule 72, which is a sealed capsule whose shell is made from a moisture degradable material such as HPMC and optionally comprises an enteric degradable material acting as covering element 30, for collection of samples in the intestines or colon. Covering element 30 prevents gastrointestinal samples from flowing into collecting member 18.

Figure 24:
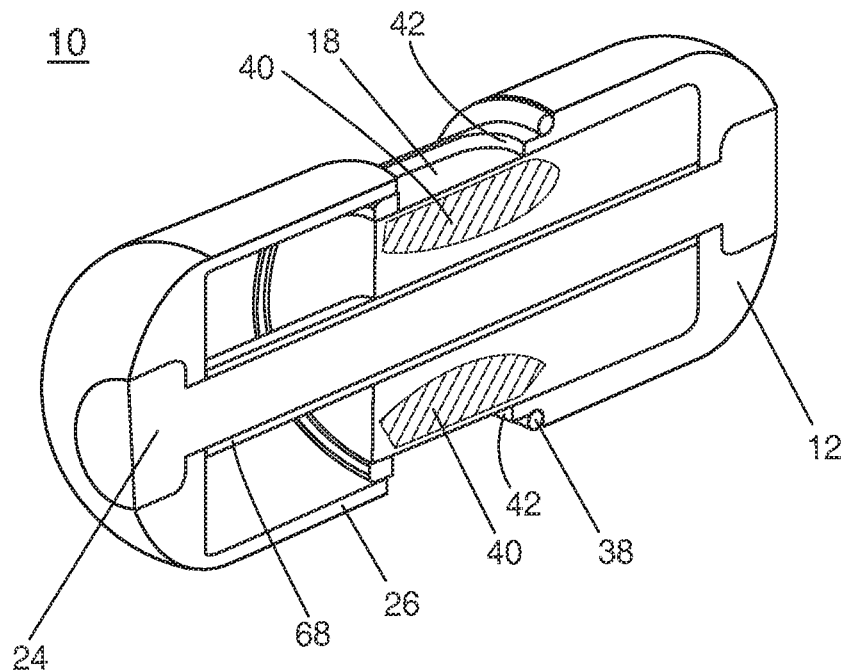
FIG. 24 illustrates a perspective sectional view of an embodiment of the device during collection of gastrointestinal samples.

As illustrated in FIG. 24, in a sectional perspective view, when device 10 has arrived at the desired sampling location in the GI tract, capsule 72 and covering element 30 have degraded and are no longer present around device 10. Gastrointestinal samples 40 start flowing into collecting member 18 through opening 42 due to the hydrophilic wicking nature of the porous collecting member 18, or due to the diffusion of liquid into a water soluble collecting member 18. Actuator 24 is a bar-bell shaped elastically-stretchable axial member made from a material such as a silicone that is in the maximally-stretched and maximal-potential energy configuration in the state illustrated in FIG. 24. When allowed to partially relax, actuator 24 moves external piston 26 over body 12 to seal opening 42. Support 68 is a compression member made from moisture degradable material. Such materials comprise HPMC, PVA solid and PVA foam. Support 68 extends from body 12 to external piston 26. When dry, support 68 prevents stretched actuator 24 from moving to the partially relaxed state and thereby separates body 12 from external piston 26. As gastrointestinal samples 40 flow into collecting member 18, the moisture contained therein eventually reaches the center portion of collecting member 18 and starts to degrade the mechanical strength of support 68.

Figure 25:
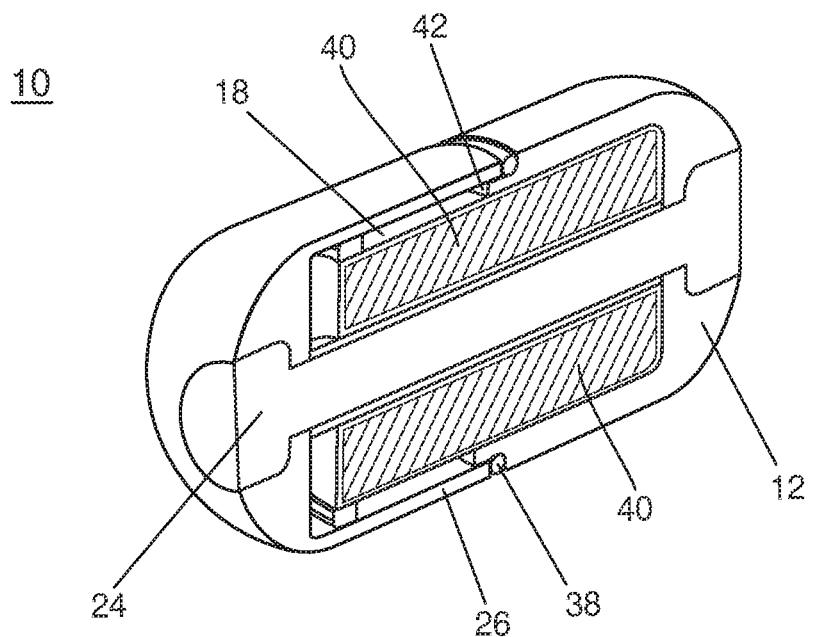
FIG. 25 illustrates a perspective sectional view of an embodiment of the device after collection of gastrointestinal samples.

As illustrated in FIG. 25, in a sectional perspective view, gastrointestinal samples 40 have finished flowing into collecting member 18 and have degraded support 68. Support 68 has lost structural integrity and is no longer present as a functional component of device 10. Actuator 24 transitions towards the partially relaxed state and moves external piston 26 over body 12 towards seal 38. Eventually, external piston 26 covers opening 42 and is sealed against seal 38 with residual potential energy, or tension, present in actuator 24, thereby isolating gastrointestinal samples 40 inside collecting member 18 and preventing further fluid flow into or out of collecting member 18. Device 10 is excreted from the body in this state. Once outside of the body, external piston 26 is separated from body 12 to access collecting member 18, which is full of gastrointestinal samples 40.

In some embodiments, a latch mechanism activates and locks once seal 38 is engaged, preventing further separation of seal 38 and exposure of collecting member 18 to the outside environment until gastrointestinal samples are extracted from device 10.

In some embodiments, as support 68 is degraded by moisture, piston 26 pushes collecting member 18 into the hollow space of body 12. Piston 26 and body 12 are eventually pulled together by actuator 24 and sealed via seal 38, thereby isolating gastrointestinal samples 40 inside collecting member 18. Residual potential energy, or tension, in actuator 24 keeps piston 26 sealed up against body 12, thereby preventing further fluid flow into or out of collecting member 18.

Figure 26:
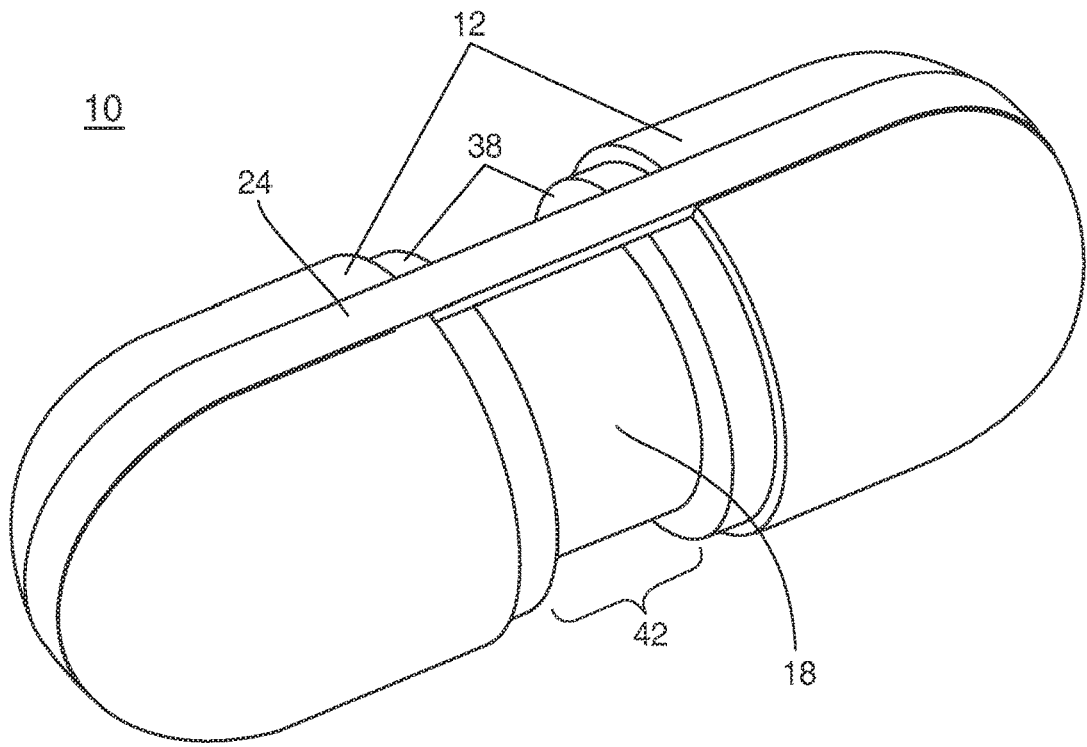
FIG. 26 illustrates a perspective view of an embodiment of the device prior to collection of gastrointestinal samples.

With reference to an embodiment shown in FIG. 26 in a perspective view, device 10 has been released from a covering element that covered opening 42. Device 10 is configured to sample the fluids in the GI tract. Collecting member 18 is a cylindrical shaped porous or water soluble element which is in fluid communication with the lumen of the GI tract through opening 42. Device 10 comprises two device bodies 12, each formed as a hollow piston with seal 38 around the opening end. After collecting a gastrointestinal sample, actuator 24 which is in the form of an external stretched elastic band with stored potential energy, moves the two halves of body 12 inwards towards each other until seals 38 contact, thereby closing off opening 42 and sealing gastrointestinal samples inside collecting member 18.

Figure 27:
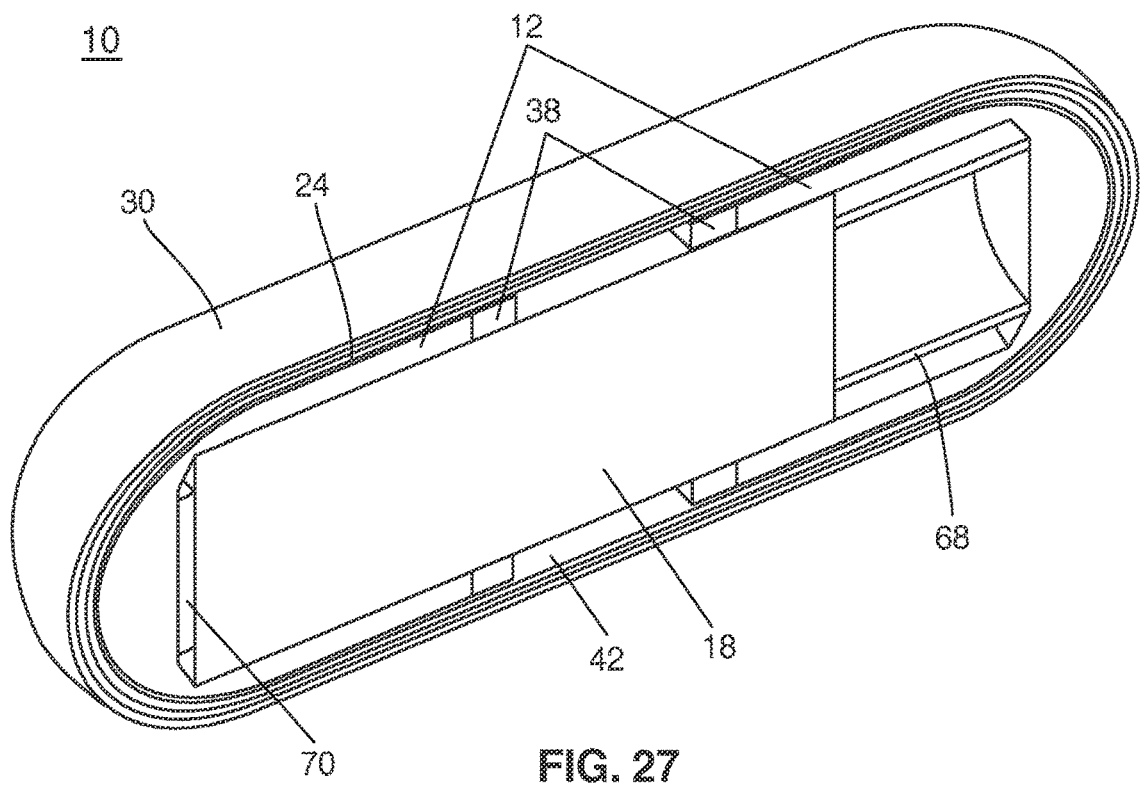
FIG. 27 illustrates a perspective sectional view of an embodiment of the device prior to collection of gastrointestinal samples.

As illustrated in FIG. 27 in a sectional perspective view, device 10 is shown before reaching the desired sampling location. Device 10 is within is a sealed capsule whose shell is made from a moisture degradable material such as HPMC and optionally comprises an enteric degradable material acting as covering element 30, for collection of samples in the intestines or colon. Covering element 30 prevents gastrointestinal samples from entering into fluid communication with collecting member 18. Magnetic or ferromagnetic attraction element 70 serves to aid recovery of device 10 in the toilet bowl using a hand-held wand comprising a magnetic or ferromagnetic tip. Attraction element 70 also serves as a radiopaque marker to enable visualization of device 10 in the GI tract using non-invasive imaging means.

Figure 28:
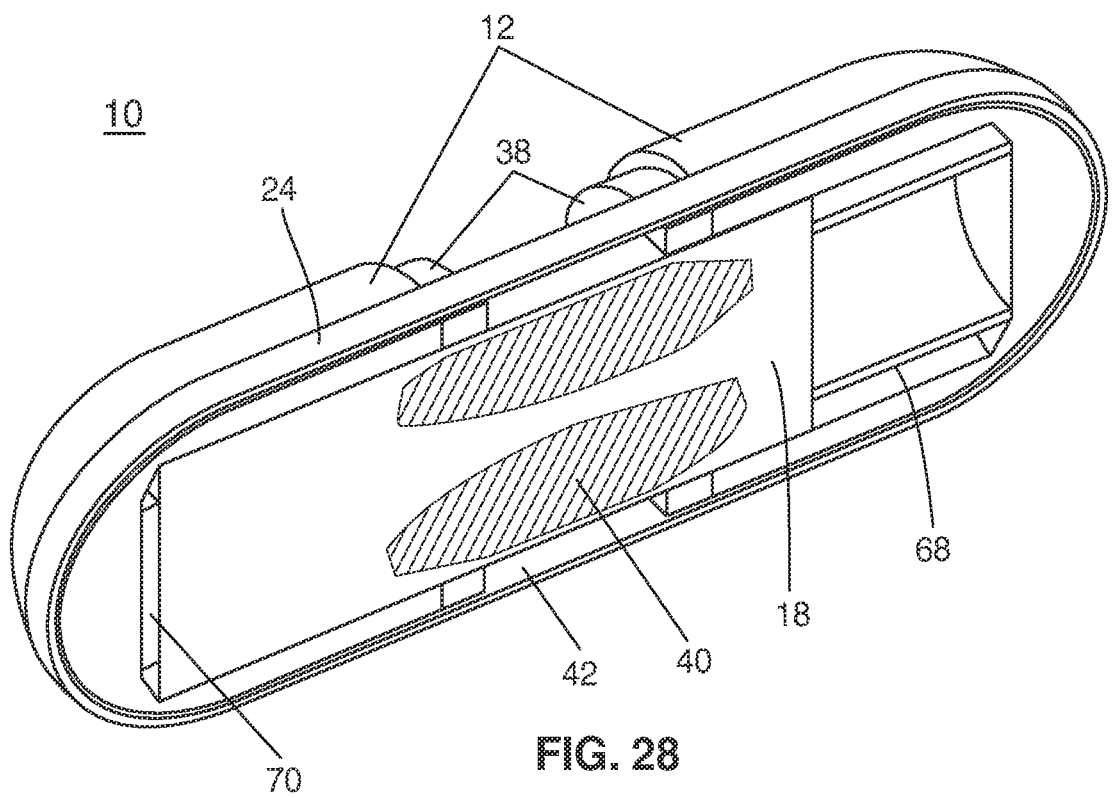
FIG. 28 illustrates a perspective sectional view of an embodiment of the device during collection of gastrointestinal samples.

As illustrated in FIG. 28, in a sectional perspective view, when device 10 has arrived at the desired sampling location in the GI tract, the capsule and associated covering element 30 has degraded and is no longer present around device 10. Gastrointestinal samples 40 start flowing into collecting member 18 through opening 42 due to the hydrophilic wicking nature of the porous collecting member 18. Actuator 24 is an external elastic band that is in the maximally-stretched and maximal-potential energy configuration. When allowed to partially relax, actuator 24 moves body 12 inwards over collecting member 18, which acts as a guide so that eventually seals 38 meet and seal opening 42. Support 68 is a compression member made from moisture degradable material that extends from body 12 to one end of collecting member 18. When dry, support 68 prevents the two halves of body 12 from moving inwards towards one another, thereby forming opening 42. After gastrointestinal samples 40 have reached the edge of colleting member 18, the moisture contained therein eventually degrades support 68.

Figure 29:
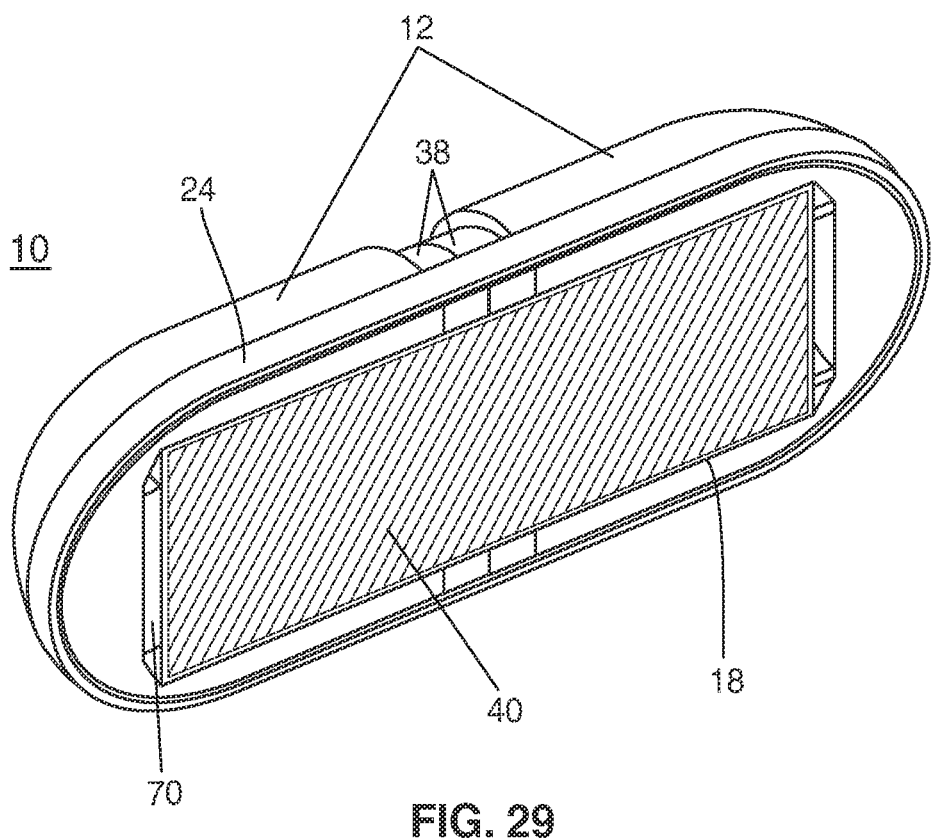
FIG. 29 illustrates a perspective sectional view of an embodiment of the device after collection of gastrointestinal samples.

As illustrated in FIG. 29, in a sectional perspective view, gastrointestinal samples 40 have filled collecting member 18 and have degraded support 68. Support 68 has lost structural integrity and is no longer present as a functional component of device 10. Actuator 24 transitions towards the partially relaxed low-potential energy state and has moved the two halves of body 12 inwards until seals 38 contact, thereby closing off opening 42 and sealing gastrointestinal samples 40 inside collecting member 18. Residual potential energy, or tension, in actuator 24 keeps the two halves of body 12 and seals 38 pressed together, thereby isolating gastrointestinal samples 40 inside collecting member 18 and preventing further fluid flow in or out of collecting member 18. Device 10 is excreted from the body in this state. Once outside of the body, the two halves of body 12 are separated to access collecting member 18, which is full of gastrointestinal samples 40.

In some embodiments, collecting member 18 is made of a porous material that can resist compression when dry. Such materials comprise sponges made of PVA or natural sponges. For example, as shown in FIGS. 26-29, collecting member 18, when dry, also serves as support 68 in resisting the compression force exerted by stretched actuator 24 and prevents the two halves of body 12 and/or piston 26 from moving inwards towards one another, thereby forming opening 42. The moisture of the gastrointestinal samples 40 soften collecting member 18. Collecting member 18 loses structural rigidity and the ability to resist compression. Stretched actuator 24 compresses the two halves of body 12 and/or piston 26 to seal against seal 38, thereby preventing all further fluid communication between collecting member 18 and the gastrointestinal tract.

Figure 30:
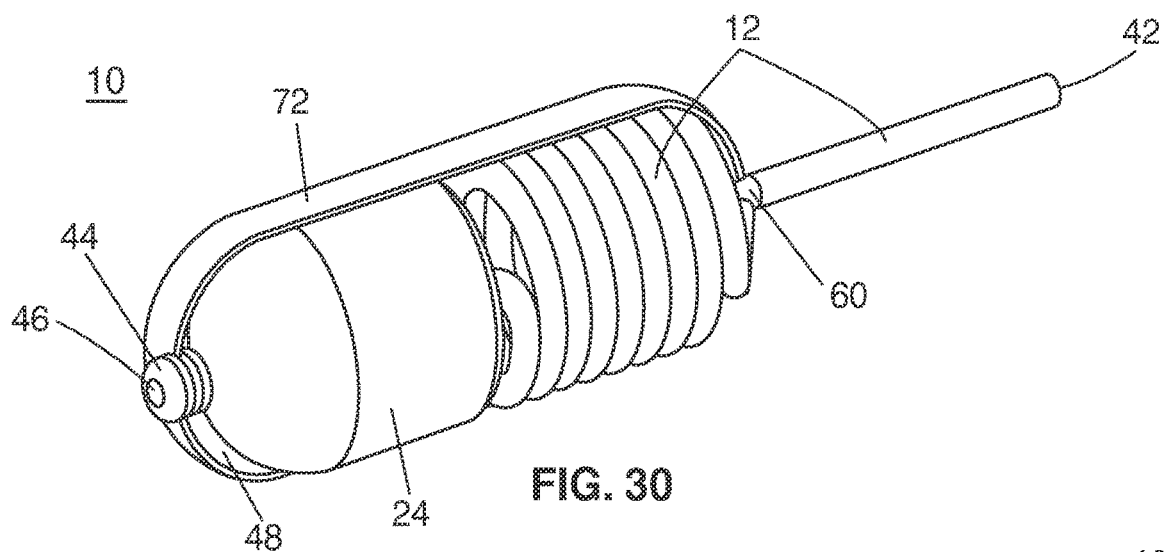
FIG. 30 illustrates a cut-away perspective view of an embodiment of the device prior to potential energy being stored in the actuator.

With reference to an embodiment shown in FIG. 30, the components of device 10 are shown in perspective view with capsule 72 partially cut away to show the internal components of device 10. Device 10 comprises body 12 in the form of a coiled hollow tube whose internal lumen forms collecting member 18. Body 12 opens to the outside of capsule 72 through hole 60. The opening 42 of hollow tube-shaped body 12 connects one end of collecting member 18 to the GI tract. A portion of body 12 is coiled inside capsule 72. The other end of collecting member 18 is connected via fluid communication to actuator 24 that is in the form of a hollow bladder made from an elastic material or comprising an elastic member that is normally in its fully expanded state. Between actuator 24 and body 12 is space 48. Seal 44 goes through a hole in body 12. Seal 44 comprises orifice 46 that is normally open, connecting space 48 to the environment outside capsule 72. Device 10 as shown in FIG. 30 is in the empty state with expanded hollow actuator 24, empty collecting member 18 and space 48 full of gas at atmospheric pressure.

Figure 31:
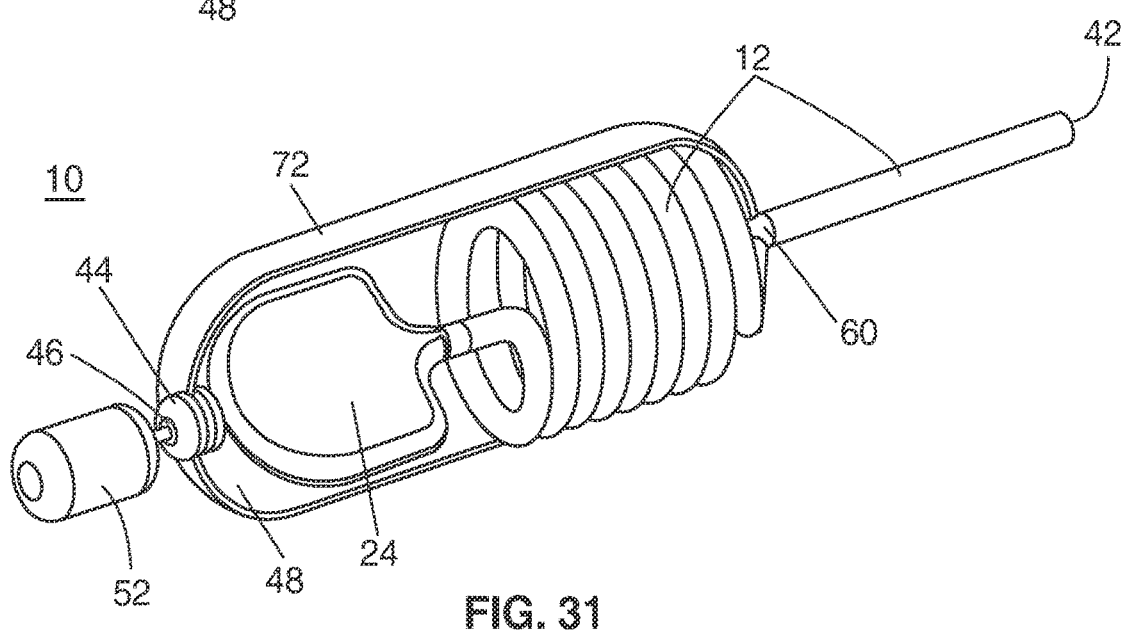
FIG. 31 illustrates a cut-away perspective view of an embodiment of the device with potential energy stored in the actuator and prior to collecting any gastrointestinal samples.

As shown in FIG. 31, a gas or fluid is pumped into capsule 72 via orifice 46 and occupies space 48. Because of the pressure of the fluid in space 48, hollow bladder-shaped actuator 24 collapses to a minimal volume, thereby storing potential energy in the elastic material or elastic member, while expelling the gas within it through opening 42 of body 12 in the process. Plug 52 is inserted into orifice 46 to create a seal that prevents the fluid inside space 48 from escaping outside body 12. This is the state that device 10 is delivered to a patient before use.

Figure 32:
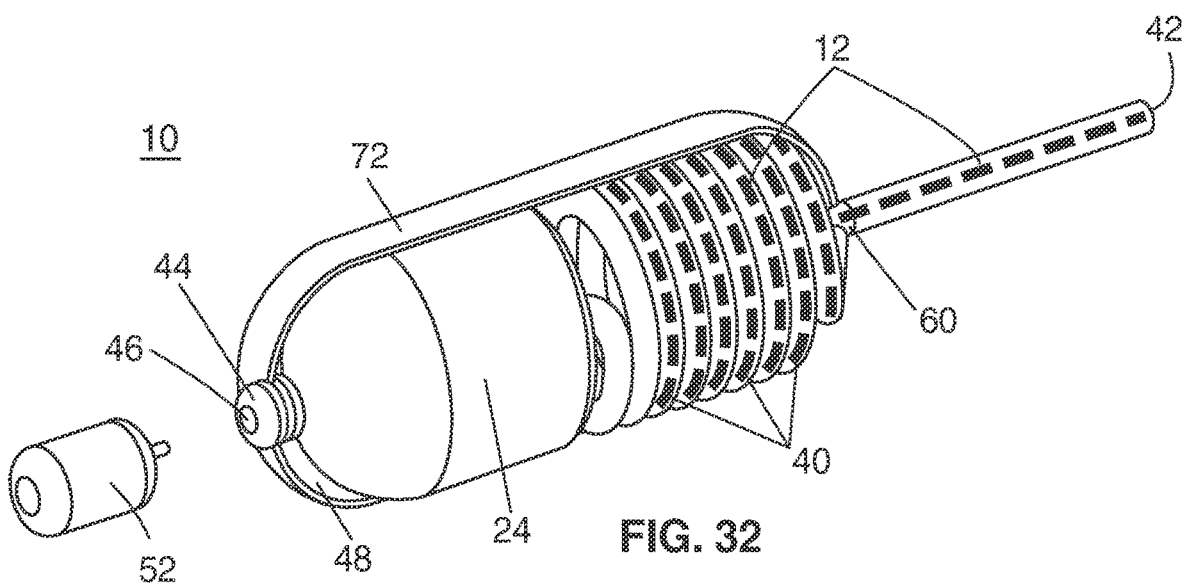
FIG. 32 illustrates a cut-away perspective view of an embodiment of the device after collecting gastrointestinal samples.

As shown in FIG. 32, when plug 52 is removed from orifice 46, the hollow bladder actuator 24 starts to expand to its relaxed state and shape, thereby forcing the fluid or gas from space 48 out of orifice 46. As hollow bladder actuator 24 expands, a negative pressure is formed in collecting member 18 that draws in gastrointestinal samples 40 through opening 42. The differential volume of hollow bladder 24 between the expanded and compressed states is less than the internal volume of collecting member 18. In this manner, gastrointestinal samples 40 only reside within the spatially-segregated linear-array format of a long hollow collecting member 18, and not in the volume of hollow bladder-shaped actuator 24. The size of orifice 46, the viscosity of the gas or fluid in space 48, and the elasticity of actuator 24 determine the rate of gastrointestinal sampling. The rate of expansion between the fully collapsed state and a fully expanded state of actuator 24 can take 1 minute to 1 hour to sample a specific region of the GI tract, or 1 hour to 8 hours to fully sample the entire GI tract.

In some embodiments, the fluid introduced into space 48 comprises a gas, water, saline, or oil.

In some embodiments when oil is introduced into space 48, a moisture degradable covering element blocks orifice 46. Therefore, the sample collection starts only when the covering element blocking orifice 46 is degraded after sufficient exposure to moisture in the GI tract.

In some embodiments, the fluid introduced into space 48 is a solid at room temperature and a liquid at body temperature.

In some embodiments, a solid fluid dissolvable element is introduced into space 48 and is exposed to fluids in the GI tract and is eliminated through orifice 46.

In some embodiments, a narrowing portion of the lumen of hollow tube-shaped body 12 or a constriction therein, acts to limit the rate of sampling of the gastrointestinal samples.

In some embodiments, body 12 is a hollow tube 0.2 to 2.5 mm in internal diameter, and 0.4 to 3.0 mm in external diameter and 20 to 200 cm in length. The internal hollow lumen of body 12 form collecting member 18. Gastrointestinal samples 40 are introduced into collecting member 18 via opening 42. Gastrointestinal samples 40 form a spatially separated linear array within collecting member 18 in the order in which they are collected. Movement of gastrointestinal samples 40 into collecting member 18 is due to bulk flow driven by the pressure differential between a radially-collapsed and radially-expanded body 12. Movement of gastrointestinal samples 40 inside collecting member 18 does not act to chromatographically separate out the components of gastrointestinal samples 40 due to their relative sizes, as would be the case in capillaries used for chromatography which are usually 0.1 mm internal diameter or smaller.

Diffusion linearly between regions of the linear array of gastrointestinal samples 40 inside tube-shaped body 12 is minimal. In 24 hours at 37 degrees Celsius, the distance of diffusion of small molecules such as glucose, salts, large molecules such as hemoglobin, and even motile bacteria is less than 2 cm. For example, if gastrointestinal samples 40 are collected from the mouth to the rectum at a constant rate within a 60 cm long hollow collecting member 18, then the spatial resolution of sampling is +/−2 cm in collecting member 18, which translates to +/−1 foot of a 30 foot long GI tract. This represents sufficient resolution to identify areas of interest in the GI tract. If increased resolution is required, collecting member 18 can be longer than 60 cm.

In some embodiments, portions of the gastrointestinal samples collected in a linear array format inside a long hollow collecting member 18 are separated with bubbles of oil or gas to minimize the diffusion of biomolecules between the portions of gastrointestinal samples.

In another embodiment, gastrointestinal samples 40 are recovered in a first-in first-out basis by pressurizing collecting member 18 from opening 42 to push gastrointestinal samples 40 out of the end of collecting member 18 farthest from opening 42. This approach avoids cross contaminating the firstly collected samples in the linear array with the lastly collected samples.

The GI tract is full of gas in certain regions. At the time of the opening of the vacuum container of prior art devices, if the sampling port is exposed to a gas, then the vacuum force will immediately suck in the gas instead of a fluid sample. Vacuum containers described in the prior art that open at a specific point in time will invariably collect far more gas than fluids, which will lead to non-informative sample collection. In contrast, device 10 disclosed herein collects samples at a much more controllable rate which is relatively independent of the viscosity of the material being sampled. By sampling one region of the GI tract over 1 minute to 1 hour, or sampling the entire GI tract up between the stomach and the ascending colon over a period of 1 hour to 8 hours, it is highly likely that opening 42 will be in fluid communication with fluid gastrointestinal samples for at least some portion of this sampling time window. In some embodiments, for example, as illustrated in FIGS. 30 to 32, the sampling rate is governed mainly by the rate at which fluid or gas leaves orifice 46 and the elasticity of bladder actuator 24. Therefore, the sampling mode is based on positive displacement. The sampling rate of gastrointestinal samples 40 through opening 42 is the same whether a liquid or gas is being sampled. In the embodiment where body 12 comprises a collapsed lumen forming collecting member 18, the rate at which body 12 is unfolded, unwound or untwisted determines the rate of sampling of gastrointestinal samples 40. The rate of unfolding, unwinding and untwisting of body 12 is determined by, among other parameters, the degradation qualities of covering element 30 and the elasticity of body 12. The body comprising a collapsed, wound, twisted, or folded tube provides a dual advantage of limiting the sampling rate (thus reducing collection of gas as compared to prior art devices) and providing a much larger volume collecting member 18 within the confined space provided by a swallowable capsule.

In some embodiments, a porous element or screen with a preselected pore size in the range of 0.1 microns to 200 microns is placed in or in front of opening 42 of body 12 to prevent blockage or to prevent ingestion of any sample elements larger than the pore cut off size. By way of example, a membrane with a pore size of 0.2 microns would not allow any microbial cells to enter collecting member 18, but rather would collect only the fluid surrounding the microbes that may contain other dissolved or suspended biomolecules of interest.

In some embodiments, body 12 comprises a tube that is coiled, spooled, twisted, folded or compressed tightly enough inside capsule 72 to elastically or reversibly collapse the hollow lumen within body 12 that forms collecting member 18. In order to provide the correct internal collection volume as well as a controllable vacuum force to pull in gastrointestinal samples over a time range of 1 minute to 1 hour to sample one region of the GI tract, or 1 hour to 8 hours to sample most of the GI tract up until the right colon, hollow tube body 12 is preferably 0.2 to 2.5 mm in internal diameter, and 0.4 to 3.0 mm in external diameter and 20 to 200 cm in length. Other dimensions are also possible. For example, the tube shaped body can have an external diameter of about 5.0-7.0 mm. In some embodiments, the tube shaped body comprises an aspect ratio of about 5 or greater. The collapsed collecting member is placed inside capsule 72 in such a manner that capsule 72 prevents the collapsed lumen of body 12 from expanding radially. Capsule 72 or body 12 can be coated or comprise enteric degradable covering element 30. When capsule 72 dissolves or degrades, the collapsed lumen of body 12 starts to transition to its normal relaxed circular cross sectional shape with an expanded hollow space that forms collecting member 18. The hollow space forming collecting member 18 is opened either due to elastic nature of body 12 material or due to capillary forces of liquid collected therein. As body 12 unwinds, untwists, unfolds or expands, liquid and gas gastrointestinal samples are sucked through sampling opening 42 inside collecting member 18 and collected therein.

In some embodiments, the energy that draws in gastrointestinal samples into collecting member 18 is stored as potential energy in the radial collapse of the lumen of an elastic hollow tube-shaped body 12 with a circular cross section.

In some embodiments, body 12 with the lumen open or collapsed is wound around a central axis in a spiral fashion, for example, as illustrated in FIGS. 30-32 to maximize the volume of collecting member 18 per the volume of device 10 before swallowing.

In some embodiments, body 12 with the lumen open or collapsed is wound around a central axis in a spiral fashion, for example, as illustrated in FIGS. 30-32 in multiple overlapping layers to maximize the volume of collecting member 18 per the volume of device 10 before swallowing.

Figure 35:
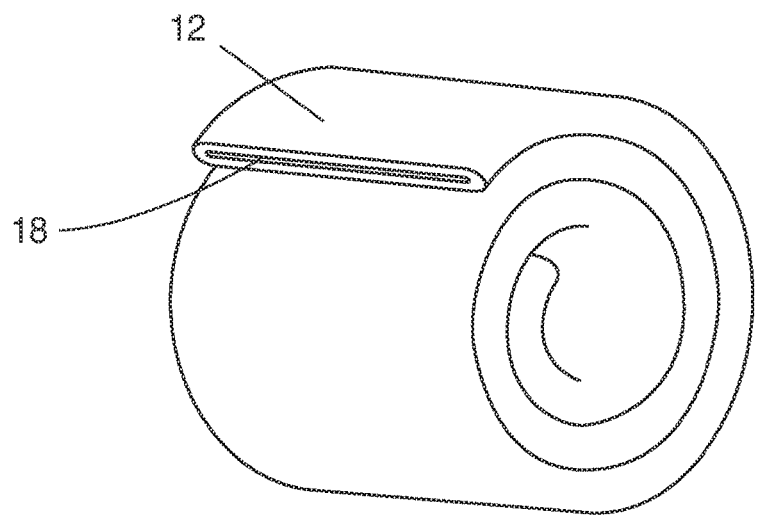
FIG. 35 illustrates an embodiment of a collecting member with a collapsed lumen wound as a spiral around a central axis.

In some embodiments, body 12 with a radially collapsed lumen is wound around a central axis in a spiral pattern as illustrated, for example, in FIG. 35. This configuration is similar to the winding of a collapsed fire hose.

Figure 36:
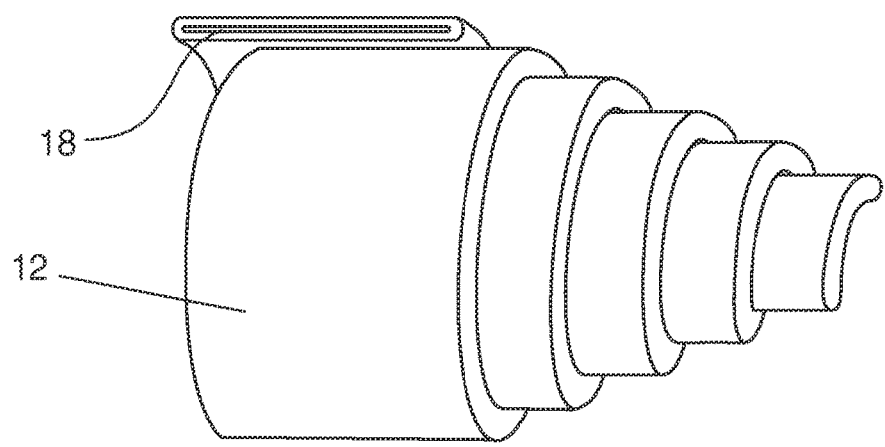
FIG. 36 illustrates an embodiment of a collecting member with a collapsed lumen wound as a spiral with axial offset around a central axis.

In some embodiments, body 12 with a radially collapsed lumen is wound around a central axis in a spiral fashion with an axial offset as illustrated, for example, in FIG. 36. Body 12 can either not overlap at all, or partially overlaps on itself in this embodiment.

Figure 37:
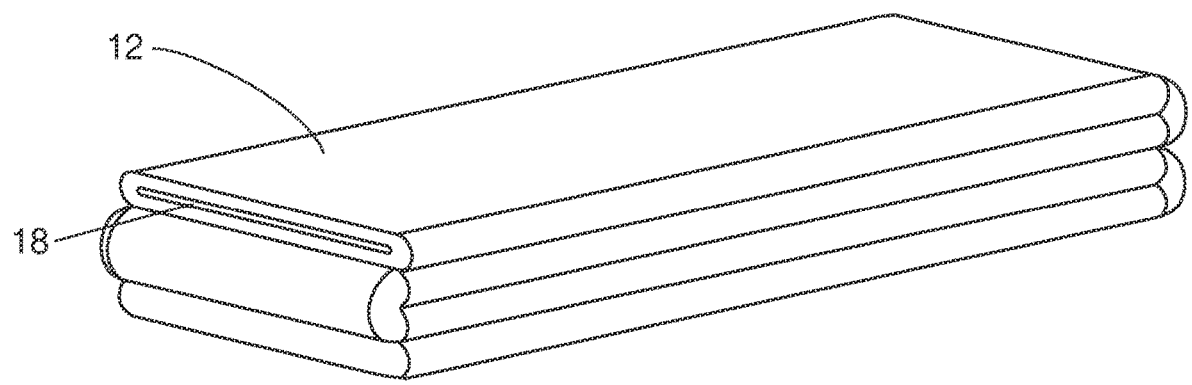
FIG. 37 illustrates an embodiment of a collecting member with a collapsed lumen folded in an accordion fold configuration.

In some embodiments, body 12 with a radially collapsed lumen is folded one or more times in an accordion or "Z-fold" fashion as illustrated, for example, in FIG. 37.

Figure 38:
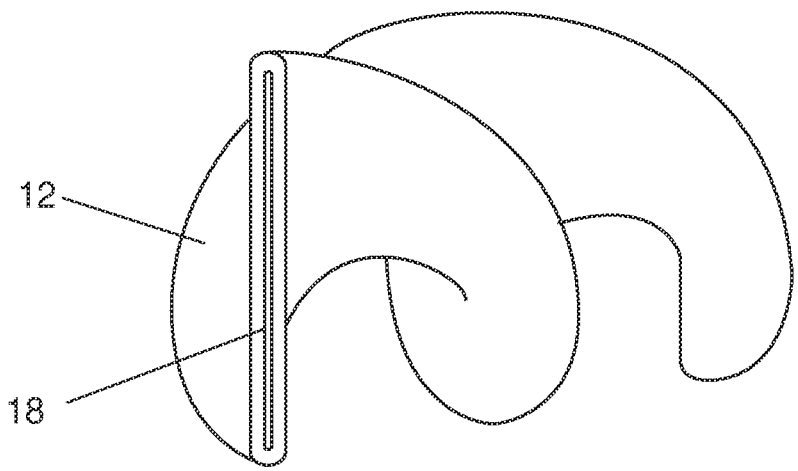
FIG. 38 illustrates an embodiment of a collecting member with a collapsed lumen twisted into a helix or coil configuration.

In some embodiments, body 12 with the lumen open or collapsed is twisted into a helix or coil as illustrated, for example, in FIG. 38.

In some embodiments, body 12 with the lumen open or collapsed is twisted into a helix or coil and then folded one or more times in an accordion or "Z-fold" fashion.

In some embodiments, body 12 with the lumen open or collapsed is folded one or more times in an accordion or "Z-fold" fashion and then twisted into a helix or coil.

In some embodiments, body 12 with the lumen open or collapsed is twisted into a super-helix or super-coil. A super-helix or super-coil is a form that has undergone additional twisting in the same direction as or in the opposite direction from the turns in the original helix or coil.

Figure 39:
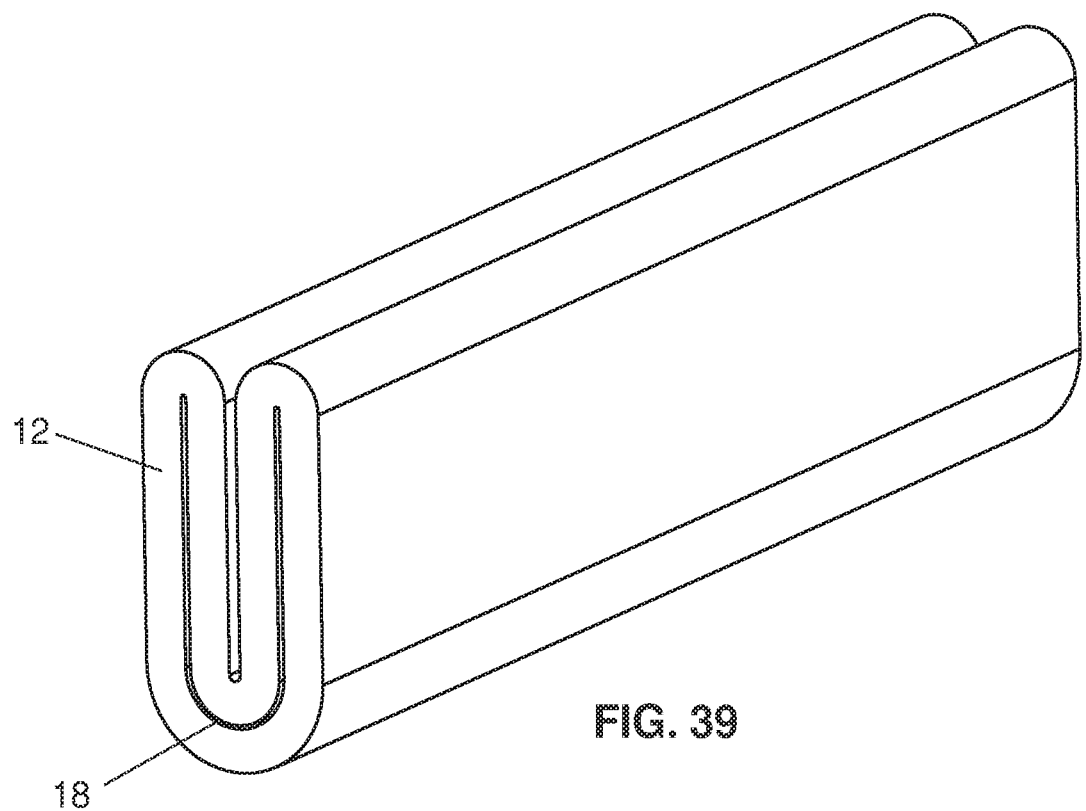
FIG. 39 illustrates an embodiment of a collecting member with a collapsed lumen folded into a creased configuration.

In some embodiments, tube-shaped body 12 with a radially collapsed lumen forming collecting member 18 is folded one or more time along a central axis in a creased manner as illustrated, for example, in FIG. 39.

In some embodiments, tube-shaped body 12 with a radially collapsed lumen forming collecting member 18 is packed tightly and randomly inside an external body to maximize the volume of collected sample per the volume of device 10 before swallowing.

It can be preferred that the folding pattern of tube-shaped body 12 not involve invaginating the surface of body 12 in on itself. Invagination of a long tube creates significant friction that does not allow for self-expansion. Folding via invagination works best with a spherical or bulb-shaped body 12. However, for any given collection volume, a spherical or bulb-shaped body 12 will increase in diameter, and hence present a greater retention risk in the GI tract, relative to a long tube-shaped body 12.

The packaging configurations described above can be important for at least three reasons. Firstly, the packaging configurations described above minimize the dead volume and residual gas inside capsule 72. Any residual gas inside capsule 72 may be sampled by device 10 itself, thereby taking up precious volume in collecting member 18 that should be dedicated to the collection of fluid gastrointestinal samples. Furthermore, residual gas can contain atmospheric oxygen which is detrimental to the viability of the anaerobic microbes being collected in the GI tract. In prior art devices containing expandable bellows for example, the dead volume of device 10 is significant, even before sample collection has occurred. Furthermore, collecting member 18 does not need to vent any trapped gas when body 12 is evacuated of gas via radial collapse prior to packaging in capsule 72.

Secondly, the packaging configurations described above maximize the potential volume of collecting member 18 per volume of ingested capsule 72. Since the volume of collecting member 18 can be effectively zero when properly packaged according to the configurations described above, more than about 50%, preferably more than about 70% percent of the internal volume of capsule 72 can be occupied with the thin wall tube shaped body 12 and optionally a one way valve mechanism. No volume within capsule 72 is required for a separate actuator or power source as typically found in prior art devices. In these embodiments, elastically radially-collapsed body 12 is both the actuator and the vessel defining the overall volume of collecting member 18. When packaged inside capsule 72, collecting member 18 has an internal dead volume of less than about 10-30% (e.g., about 15%), of its maximal volume. In other words, less than about 10-30% of the full volume of collecting member 18 is dead volume that is unavailable for sample collection when body 12 is packaged inside capsule 72. Collecting member 18 expands to its full volume once outside of capsule 72 with at least about 70-90% of the full volume being occupied by gastrointestinal samples.

Thirdly, the packaging configurations described above provide many ways to control the rate of expansion of body 12, and hence the rate of sample collection in the GI tract. It is possible to control the rate of unfolding, uncoiling, untwisting and radial expansion of an elastic tube-shaped body 12 in many ways that are dependent on time or pH. The rate of sampling can therefore be controlled to be in the range of about 1 minute to 8 hours depending on the number of regions of the GI tract to be sampled.

In some embodiments, the elasticity of the wound, folded or randomly packed body 12 applies a force that helps break the shell of capsule 72 or covering element 30 in an axial and/or radial direction to initiate sampling when inside the GI tract.

In some embodiments, multiple covering elements 30 are applied in concentric shells around discrete layers of the coiled or spooled tube-shaped body 12. Covering element 30 acts to keep a layer of body 12 in the collapsed state. When a layer of covering element 30 degrades due to moisture, time or pH levels, the coiled or spooled body 12 unwinds, thereby expanding the lumen and drawing in gastrointestinal samples into collecting member 18 in a controlled manner. The parameters of degradation of covering elements 30 layers is controlled so that the outer layers of the coiled of spooled body 12 are freed to unwind before the internal layers. In this manner, device 10 samples continuously along the GI tract for a time period of about 1 minute to 1 hour, or about 1 hour to 8 hours. Furthermore, an orderly and gradual unwinding of body 12 prevents the tube from unwinding all at once and kinking or bending on itself.

Figure 33:
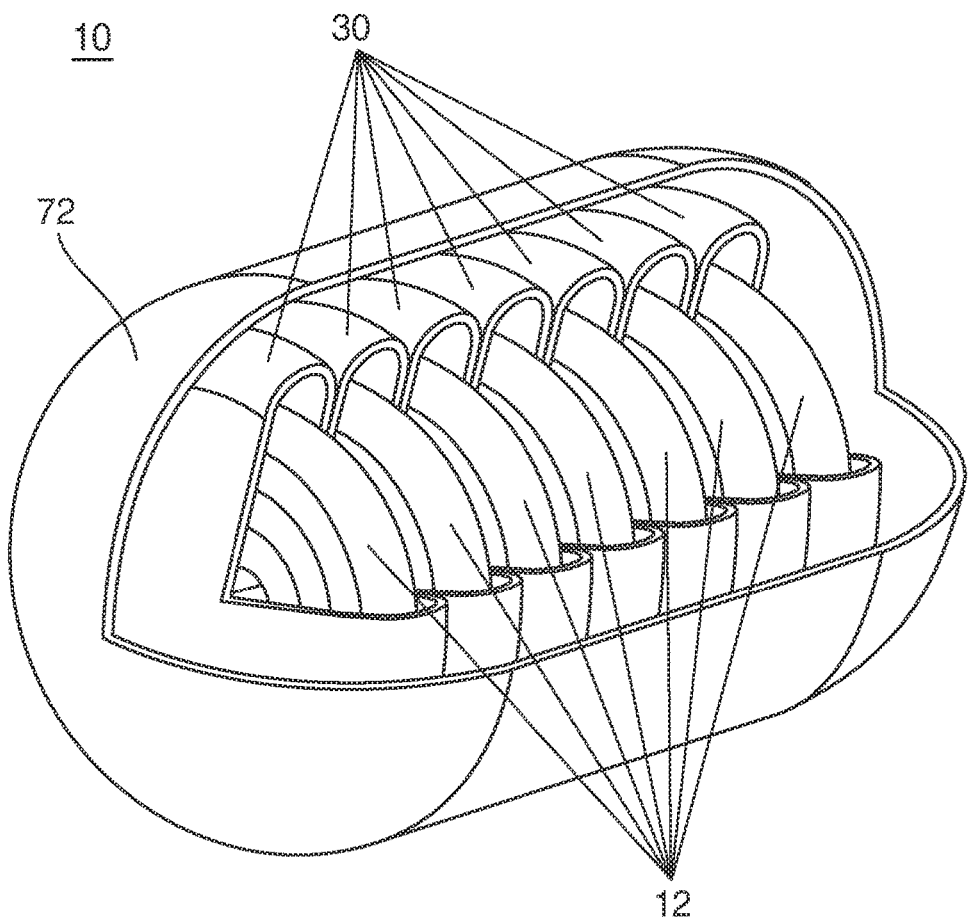
FIG. 33 illustrates a partial sectional perspective view of an embodiment of the device configured as spools of wound collecting members with individual covering elements.

In an embodiment illustrated in FIG. 33 in partial sectional perspective view, body 12 comprises a continuous or segmented tube that is compressed to have a radially-collapsed lumen forming collecting member 18. Body 12 is coiled in a manner shown in FIG. 35 to form a series of stacked flat disks which are eventually placed as a cylindrical object inside capsule 72. Each body 12 is coated with a unique moisture-degradable, enteric degradable, time degradable, or colonic targeting covering element 30 that allows each body 12 to unravel and collect GI samples in specific regions of the GI tract.

In some embodiments, the pH at which covering elements 30 degrade are ordered from a lower pH at the region of opening 42 of body 12 to a higher pH at the region of the closed end of tube-shaped collecting member 18. In this manner, the thin-walled tube-shaped collecting member uncoils from opening 42 as device 10 travels from the duodenum, where the pH is 5-6, towards the ileum where the pH is 7-8. In this manner, device 10 samples continuously along the GI tract over a time range of about 1 hour to 8 hours.

In some embodiments, capsule 72 is coated with covering elements 30 comprising different moisture-degradable, enteric degradable, time degradable, colonic targeting materials, or different thicknesses of coating, in axially-distinct segments so that specific segments of capsule 72 degrade in a specific order. When a capsule segment degrades, that segment of capsule 72 no longer provides a radial constraining force on the coiled body 12 contained in that segment. Therefore, the coiled body 12 in that segment is allowed to uncoil, the lumen of body 12 expands, and the collecting member 18 collects samples in that region of the GI tract.

In some embodiments, body 12 can comprise an elastic thin walled tube with one closed end and one open end that is compressed to have a collapsed lumen and is coiled to form a stack of three flat disks similar to three layers of a coiled firehose as illustrated in FIG. 35. The closed end of body 12 is in the radial center of the first disk and the open end of body 12 is at the outer circumference of the third disk. The open end of body 12 is opening 42. The three disks are stacked one on top of the other to form a cylindrical object which is introduced into water-degradable capsule 72. The first round cap portion of capsule 72 located adjacent to the opening 42 is uncoated and will dissolve in the stomach. The middle portion of capsule 72 is coated with a first enteric covering element 30 that targets the proximal small intestines, and the second cap portion of capsule 72 adjacent to the closed end of body 12 is coated with a second enteric covering element that targets the distal small intestines. After being swallowed, the first cap portion of capsule 72 dissolves in the stomach which allows the first disk to uncoil, which in turn expands the lumen of the first disk of body 12 to draw in GI samples from the stomach. In the proximal small intestines, the middle portion of capsule 72 dissolves which allows the second disk of body 12 to uncoil and sample the proximal small intestine contents. In the distal small intestines, the second cap portion of capsule 72 dissolves which allows the third disk of body 12 to uncoil and sample the distal small intestine contents. A linear array of samples from the stomach, proximal small intestines and distal small intestines now rests inside collecting member 18 which formed by the inner lumen of body 12.

Importantly, in the linear array embodiments, the first samples entering collecting member 18 do not experience any contamination by the walls of the lumen of body 12. Subsequent samples from more distal portions of the GI tract that enter collecting member 18 may be exposed to trace amounts of the previous samples adhering to the walls of the lumen of body 12. However, this cross contamination also recapitulates the natural cross contamination in the GI tract in which most biomolecules in the proximal GI tract eventually pass through and are present in the more distal GI tract on the way out of the body. More disks and more enteric coating segments can be used to sample the GI tract at a finer resolution. The tube shaped body 12 can also be a segmented tube with each segment representing a discrete collecting member 18 to further prevent cross contamination between the collected samples.

In some embodiments, one end of a hollow tube-shaped body 12 is closed so that liquid and gas gastrointestinal samples can enter into only a single opening 42 of collecting member 18 as it unwinds, untwists, unfolds or expands.

In some embodiments, sampling opening 42 of the hollow tube-shaped body 12 with a collapsed lumen is on the outside of the winding or folding configurations shown in FIGS. 35 to 39. In these embodiments, device 10 starts to sample as soon as body 12 starts to unwind, untwist, unfold or expands, which allows for sampling in the more proximal regions of the GI tract.

In some embodiments, sampling opening 42 of the hollow tube-shaped body 12 with a collapsed lumen is on the inside of the winding or folding configurations shown in FIGS. 35 to 39. In these embodiments, device 10 starts to sample only after the entirety of body 12 has unwound, untwisted, unfolded or expanded. This configuration allows for peristalsis to have an object of sufficient size to act on in order to carry device 10 to the distal regions of the GI tract before sampling starts. In this embodiment, device 10 is configured for sampling of the more distal regions of the GI tract.

In some embodiments that target the right ascending colon, the coiled, twisted, folded or compressed hollow body 12 is covered with a split capsule 72. When in the small intestines, radially directed squeeze pressure of the small intestine wall on device 10 prevents dislodging of split capsule 72 and the subsequent expansion of body 12. When device 10 enters into the right colon, where the internal diameter of the lumen is around 3 inches, as compared to the 1 inch diameter of the small intestine lumen, the split capsule 72 is no longer squeezed together and falls apart into separate elements or opens like a clamshell. Without the restraining force of the split capsule 72, hollow body 12 expands, and thereby device 10 starts to sample the gastrointestinal contents of the right colon.

In some embodiments that target the right ascending colon, opening 42 is sealed by a sealing element that can be dislodged in the outward radial direction, as long as no inward radial pressure is applied to the sealing element. Capsule 72 comprising covering element 30, as well as inwardly directed radial squeeze pressure of the small intestines on device 10 prevents dislodging of this sealing element until device 10 enters into the right ascending colon, where the internal diameter of the lumen is around 3 inches as compared to the 1 inch diameter of the small intestine lumen. Without the sealing element in place, GI samples from the right colon flow through opening 42 into collecting element 18.

In some embodiments that target the right colon, the coiled, folded, kinked or compressed hollow body 12 cannot unwind, unfold or expand when exposed to the inward directed radial squeeze pressure of the small intestines. When device 10 enters into the right ascending colon, where the internal diameter of the lumen is around 3 inches as compared to the 1 inch diameter of the small intestine lumen, body 12 unwinds, unfolds, unkinks or expands, which opens sampling opening 42 and thereby device 10 starts to sample the contents of the right ascending colon.

In some embodiments that target the right colon, sampling is triggered by detecting the presence of large pockets of gas around device 10. By way of example, an ultrasound transducer can detect whether device 10 is surrounded by gas, liquid, or intestinal tissue, and thereby trigger sample collection only when gas is detected for a preset period of time. Large volumes of gas, mainly hydrogen, carbon dioxide and methane, are present in the colon. This is in contrast to the small intestines which are generally full of fluid with the exception of small bubbles.

In some embodiments that target the right colon, sampling is triggered by detecting the reduction of heat flow from device 10 out to the GI tract due to large pockets of gas surrounding device 10. By way of example, a resistive heater with current feedback can detect if the heater is surrounded by gas or liquid, since heat flow is higher through liquid than through a gas.

In some embodiments, opening 42 is sealed or opened based on the expansion or contraction of a pH-sensitive hydrogel. The target pH transition point of the hydrogel is used to target a specific region of the GI tract for sampling based on the expected pH level of that region of the GI tract.

In some embodiments, the collected GI samples inside collecting member 18 comprise a volume of a gas sample adjacent to a volume of a liquid samples. The gas sample is collected separately from the liquid samples for further analysis.

In some embodiments, actuator 24 is an actuator that creates negative pressure at the opening 42 of collecting member 18. Example actuators comprise a reciprocating vacuum pump, centrifugal pump, electrical actuated actuators, solenoids, electromagnetic coils that attract or repel, electroactive polymers, piezoelectric element, and the like. Modes of pumping comprise peristaltic, pulsatile and displacement with our without one way valves.

In some embodiments, actuator 24 creates a slight positive pressure at opening 42 of collecting member 18 to flush or purge out any materials or particles that may be blocking opening 42. Actuator 24 then creates a longer or higher negative pressure at opening 42 of collecting member 18 to collect more gastrointestinal samples than were expelled during the flush or purge step.

In some embodiments, a hydrophilic or superhydrophilic inner surface and small internal diameter of the of hollow tube-shaped body 12 will make gastrointestinal samples 40 flow into collecting member 18 by capillary forces alone, eliminating the need for actuator 24. Example hydrophilic or superhydrophilic inner surfaces comprise introducing an open cell gel or foam into the lumen of body 12, acid etching, or coating the lumen of body 12 with hydrophilic or superhydrophilic molecules such as a hydrogel, and the like.

In some embodiments, the inner surface of a hollow body 12 is hydrophobic and will still enable collection of GI samples, given that the surface tension of GI samples is very low, mainly due to the bile acids contained therein acting as a detergent. Therefore, GI samples will readily flow into a body 12 made from a hydrophobic material. The advantage of a hydrophobic surface is lower adherence of gastrointestinal samples to the wall of body 12 and therefore lower cross contamination in a linear array format of collecting member 18.

In some embodiments, the inner volume of hollow tube-shaped body 12 comprises an open cell structure that increases the capillary wicking ability of collecting member 18.

In some embodiments, the wall of hollow tube-shaped body 12 comprises a material that allows the gas trapped in collecting member 18 to escape through the wall into the gaseous or liquid environment surrounding device 10. The gastrointestinal samples that are transported via capillary forces into the lumen of hollow tube-shaped body 12 displace the trapped gas out of collecting member 18 via the lumen wall at a known rate. By way of example, hollow body 12 is made from a material comprising cellulose, or cellulose ester, polysulfone, polytetrafluoroethylene (PTFE), polyvinylidene fluoride (PVDF), polyethersulfone (PES), etched polycarbonate, and collagen. These materials are gas permeable but not fluid permeable.

In some embodiments where capillary forces drive gastrointestinal samples 40 into collecting member 18, a gas permeable but water repelling venting opening on body 12 allows the gas inside collecting member 18 that is being displaced by the flow of gastrointestinal samples 40 into opening 42 to escape outside of device 10 via bulk flow or diffusion. Examples of such venting openings comprise hydrophobic materials such as polyvinylidene fluoride, polytetrafluoroethylene, and polyethylene in tube, fit, spun or porous forms. In this embodiment, gas in the GI tract will not be sampled as capillary forces will act to only drive fluid gastrointestinal samples 40 into collecting member 18. The rate of sampling in this embodiment is controlled via a combination of the diameter and hydrophilicity of the internal surface of tube-shaped collecting member 18, and the gas permeability and surface area of the venting opening. When the venting opening is exposed to the gases of the GI tract and not in contact with gastrointestinal fluids, and at the same time opening 42 which extends beyond body 12 is resting on a mucosal surface of the lumen, then mucosal gastrointestinal samples will be efficiently collected in collecting member 18 due to capillary forces since the trapped gas in collecting member 18 will easily exit the venting opening. In this manner, mucosal gastrointestinal samples are preferentially collected over bulk gastrointestinal fluid, thereby increasing the concentration of microbes sampled since microbes reside mainly on the mucosal layers of the GI tract and exist only in dilute form in bulk gastrointestinal fluids.

In some embodiments, collecting member 18 and/or the inside volume of body 12 is full of a gas that diffuses into water more readily than air. Example gases comprise helium, hydrogen, and carbon dioxide.

In some embodiments, hollow body 12 is made from lay flat tubing with essentially no gas contained within its lumen when collapsed, flat and empty. When gastrointestinal samples enter opening 42, capillary forces drive the liquid gastrointestinal samples into the lumen of body 12 which forms collecting member 18. The lumen of collecting member 18 expands from a collapsed state to an open state in the areas filled with gastrointestinal fluids. The non-sampling opening of collecting member 18 does not need to vent any trapped gas in this embodiment.

In some embodiments, the opening 42 of body 12 is flush with device capsule 72.

In some embodiments, opening 42 of hollow tube-shaped body 12 extends at least 5 mm beyond capsule 72, causing opening 42 to contact the GI tract mucosal layer at almost all times, thereby maximizing the chance of a gastrointestinal sample being collected. In this embodiment, the section of body 12 that extends beyond capsule 72 does not remain horizontal under its own weight. Therefore, gravity will force the section of body 12 that extends beyond capsule 72 to fall down against the surface of the GI lumen.

In some embodiments, opening 42 that extends beyond capsule 72 is weighted to ensure that opening 42 rests on the GI tract lumen surface.

In some embodiments, device 10 is formed using 3D printing techniques that create a coiled or tortuous hollow capillary path within the internal volume of device 10 directly. Example 3D printing techniques comprise photopolymerization, sintering or additive manufacturing.

In some embodiments, device 10 is formed using stacked sections where a collecting member 18 is formed as a depression into each layer. The layers are stacked and bonded to each other, with the backside of each layer sealing the collecting member 18 of the adjacent layer. The collecting members 18 of each layer are in fluid communication with each other via a through hole between the layers.

In some embodiments, collecting member 18 or portions thereof are formed by baffles or other thin features that are spaced sufficiently close to create surface tension to draw in the liquid gastrointestinal samples. Spacing of the baffles or thin features are in the range of 0.2 mm to 4 mm, which forces a radius of curvature of the meniscus of the gastrointestinal fluids to be in the range of 0.1 mm to 2 mm, thereby causing significant capillary action due to surface tension to draw in the gastrointestinal sample into collecting member 18.

In some embodiments, multiple opening 42 emerge from body 12. The multiple opening 42 are merged into a single collecting member 18. In this manner, the likelihood of one opening 42 being in contact with the lumen of the GI tract is maximized.

In some embodiments, more than one device 10 unit is provided as a kit for the patient to swallow at the same time. Each device 10 is designed to expose opening 42 at a different time point or location in the GI tract. Device 10 units are collected in the same bowel movements, or in subsequent bowel movements, for further analysis. It is safer to swallow a plurality of smaller device 10 units than one large device 10 that samples numerous regions of the GI tract.

A certain volume of gastrointestinal samples 40 is collected by device 10 for further analysis, which is defined as the collected volume. Device 10, packaged in capsule 72, itself has a certain external volume before it is swallowed. The ratio of the collected volume to the volume of capsule 72 is defined as the "collection volume percentage". The higher the volume of collected sample, the more analyses can be performed on the gastrointestinal samples, and/or at a higher sensitivity. Furthermore, the higher the volume of the collected sample, the easier device 10 is to identify and retrieve from the stool. At the same time, the volume of capsule 72 should be as low as possible to minimize the difficulty of swallowing the device. Device 10 itself should have as small of a diameter as possible to minimize the risk of retention of device 10 in the GI tract. For example, the retention rate of capsule endoscopy devices (Medtronic Capsule Endoscopy System, Medtronic Inc. Minneapolis, Minn., USA) which are approximately 11.6 mm in diameter and contain 3 milliliters of volume, is 1.4%. In most of these cases, the retained capsule endoscope needs to be removed from the GI tract surgically. A retention rate of 1.4% is unacceptably high for routine collection of gastrointestinal samples performed at a population-scale. To minimize or eliminate retention in the GI tract, the outside diameter of device 10 should be about 9 mm or less, preferably about 7 mm or less, and more preferably about 5 mm or less. In order to minimize discomfort while swallowing, capsule 72 volume should be about 1.37 ml or less, corresponding to a size 000 capsule which is the largest degradable capsule shell commercially available. Device 10 should still allow a collected sample volume of about 0.3 ml or more to enable sufficient sensitivity and breadth of analyses desired, leading to a minimal preferable collection volume percentage of around 0.3 ml/1.37 ml, or 22%. Table 2 below shows the volumes and diameters of common and standardized capsule sizes referred to in this patent application. Note that commercially available capsules are not made larger than size 000, which is the upper limit considered acceptable for swallowing. Any extraneous mechanisms, power sources or structure in device 10 acts to decrease the collection volume. Therefore, the configuration of device 10 disclosed herein maximizes the volume of collecting member 18 and minimizes the size and volume of all the other components of device 10 required to make it functional. The required functions of device 10 can comprise:

1. Provide a smooth outer surface while swallowing,
2. Have a maximum diameter of 9 mm, 7 mm or 5 mm or less to minimize risk of device retention,
3. Collect fluid samples at the desired region of the GI tract over a time range of 1 minute to 1 hour, or of the entire GI tract over a time range of 1 hour to 8 hours.
4. Protect the collected fluid sample from leakage, contamination or oxygen exposure.

In some embodiments, the size of capsule 72 containing device 10 is 000 or smaller and the collection volume percentage is about 25% or greater. In another embodiment, the size of capsule 72 containing device 10 is 000 or smaller and the collection volume percentage is about 50% or greater. In another embodiment, the size of capsule 72 containing device 10 is 000 or smaller and the collection volume percentage is about 100% or greater.

TABLE 2

Volumes and diameters of standard capsule sizes.

| Capsule size | 000 | 00 | 0 | 1 | 2 |
|---|---|---|---|---|---|
| Volume (ml) | 1.37 | 0.90 | 0.68 | 0.48 | 0.36 |
| Diameter (mm) | 9.91 | 8.56 | 7.64 | 6.96 | 6.39 |

In some embodiments, device 10 comprises a tube shaped body 12 that is about 9 mm in diameter or smaller, about 7 mm in diameter or smaller, about 5 mm in diameter or smaller, or about 3 mm in diameter or smaller. In order to obtain sufficient volume of sample, tube shaped body 12 when full of gastrointestinal sample is about 5 mm long or longer, about 1 cm long or longer, about 20 cm long or longer, or about 50 cm long or longer. By way of example, a 50 cm long tube with an outer diameter of 2 mm and in inner diameter of 1.5 mm has an internal volume of 0.89 ml. When the lumen of such a tube is collapsed and coiled tightly, the tube can fit inside a size 0 capsule with an internal volume of 0.68 ml. In other words, collecting member 18 can contain more volume of collected sample than the internal volume of capsule 72 containing body 12. In this example, body 12 even in the fully expanded state has a much smaller diameter than capsule 72. Body 12 also does not become longer than its original length before being compacted to fit inside capsule 72. Rather, body 12 is radially-collapsed and packaged in a volume-efficient manner before being inserted into capsule 72. Since the size 0 capsule 72 is dissolvable, capsule 72 does not present a risk of retention. However, to prevent retention of a non-dissolvable body 12 in a narrowed or constricted GI tract, which is the case in many patients suffering from Crohn's disease or ulcerative colitis, a body 12 that is about 2 mm outer diameter, or even about 7 mm outer diameter is much safer alternative than a body 12 that is 9 mm or larger in diameter.

In some embodiments and by way of example, device 10 in the form of a thin-walled segmented tube-shaped body 12 50 mm in length and 5 mm in diameter as illustrated in FIG. 34. Seal 38 acts as a one-way valve to prevent collected samples in collecting member 18 from exposure to cross contamination or leakage during the rest of the transit through the GI tract. Collecting member 18 can contain a sample volume of 1.0 ml, yet the packaged device 10, when compressed by folding, twisting, winding or random packing, fits inside a size 2 capsule which has a volume of 0.36 ml. Therefore, the collection volume percentage of this embodiment is 277%.

In some embodiments, the lumen of collecting member 18 is collapsed to form a potential space to eliminate as much dead volume and residual gas as possible. Dead volume in the packaged body 12, or within the lumen of collecting member 18, takes up space that could otherwise be used for sample collection. In addition, if the dead volume is air, then the oxygen in the air will act to kill off many of the anaerobic bacterial species collected.

In some embodiments, the dead volume, defined as the volume of residual gas inside collecting member 18 prior to being swallowed, relative to the maximal volume of collecting member 18 when full of samples is less than about 50%, preferably less than about 30% and more preferably less than about 10%.

In some embodiments that are designed to preserved the viability of the anaerobic microbes collected by device 10, the inside volume of body 12 and/or collecting member 18 is at a pressure lower than atmospheric pressure to minimize the amount of oxygen inside collecting member 18.

In some embodiments that are designed to preserved the viability of the anaerobic microbes collected by device 10, the inside volume of body 12 and/or collecting member 18 is flushed with a gas that does not contain oxygen prior to packaging device 10 inside capsule 72. Example gases comprise carbon dioxide, nitrogen and argon. Seal 38 or one way valve 24 limit the exposure of the collected sample inside collecting members 18 to oxygen even when device 10 has exited the body.

The aspect ratio of device 10 is defined as the fully expanded length divided by the fully expanded diameter of device 10. To achieve an acceptably low retention risk, the maximum diameter of device 10 is about 9 mm or smaller, preferably about 7 mm or smaller and more preferably about 5 mm or smaller. The minimum collected volume to enable the desired number of analyses on the collected gastrointestinal samples is about 0.1 ml or more, preferably about 0.3 ml or more and more preferably about 0.6 ml of more. Therefore, the aspect ratio of device 10 that satisfies both of these constraints is preferably 8 or greater. The aspect ratio of standard dissolvable capsules is around 2.75. Therefore device 10 needs to transform into an aspect ratio much higher than the aspect ratio of the outer capsule 72 containing device 10. However, long slender object have difficulty navigating through the tortuous anatomy of the small intestines. Therefore, device 10 with an aspect ratio above 5 should be segmented or thin enough to enable device 10 to bend axially to match the curvature of the small intestine lumen, which has hairpin turns of approximately 3 cm radius of curvature.

Furthermore, to maximize the volume of sample collected, it is preferable that the volume of all structures of device 10 be about 40% or less, preferably about 30% or less and more preferably about 20% or less of the volume of the collected gastrointestinal samples. Assuming that 1 ml is collected by device 10, this constraint leaves only about 0.3 ml, or preferably about 0.2 ml, or more preferably only about 0.1 ml of volume for body 12 and all associated structure, power sources, seals, valves and actuators. In the example of device 10 illustrated in FIG. 34, the collected volume is 1.0 ml and the volume of all structural elements is 0.2 ml, which is a 20% ratio for the volume of device 10 relative to the volume of the gastrointestinal sample collected. Prior art devices with motors, batteries, computational devices and other bulky elements constitute significant "overhead" and leave little space relative to the overall volume of the device for sample collection. Prior art devices, therefore, have a ratio of structural volume to collected volume far in excess of 20%.

In some embodiments, to minimize the chance of retention in the GI tract, the collecting member has a maximal cross sectional area of about 3 square mm or less, about 10 square mm or less, or about 20 square mm or less, while at the same time collecting at least 0.3 ml of gastrointestinal fluid sample.

In some embodiments, device 10 comprises multiple collecting members 18, each protected from exposure to GI fluids by a covering element that degrades at a set time, pH or bacterial level in the GI tract. By way of example, each opening 42 in device 10 that comprises seven collecting members 18 is covered in the manner depicted in Table 3 below.

TABLE 3

Design of covering elements 30 that enable sampling of various regions of the GI tract.

| Collecting member | Covering element | Region sampled |
|---|---|---|
| 1 | None | Mouth and esophagus during swallowing |
| 2 | Degrades in 5 minutes after exposure to moisture | Stomach |
| 3 | Degradable immediately at pH greater than 5 | Proximal small intestines |
| 4 | Degradable 1 hour after exposure to pH greater than 5 | Distal small intestines |
| 5 | Degradable once exposed to enteric bacteria | Ascending colon |
| 6 | Degradable 3 hours after exposure to colonic bacteria | Transverse colon |
| 7 | Degradable 7 hours after exposure to colonic bacteria | Descending colon and stool |

In alternative embodiments, six covered opening 42 are shielded from the GI tract by six covering elements 30 that are individually designed to degrade after about 0.1, 1, 2, 3, 5, and 8 hours of exposure to GI tract fluids in a pH independent manner. This configuration would enable gastrointestinal samples to be collected in the regions of the GI tract corresponding to 0.1, 1, 2, 3, 5, and 8 hours after swallowing, which is sufficient to cover the stomach, small intestines and colon regions for most individuals.

In some embodiments, the position of the GI tract sampled by device 10 is imputed or confirmed a posteriori at the time of sample analysis using one or more position identification parameters. Example position identification parameters are listed in Table 4. Position identification parameters of a collected gastrointestinal sample comprise parameters such as pH, color, bacterial count, bacterial identity, hormones, dissolved gases, enzymatic activity, biochemical markers, capsule movement patterns, and intraluminal pressure. By way of example, if the collected gastrointestinal sample is clear or pink, has a pH of less than 3, a total bacterial count of less than 1,000 bacteria per gram of fluid collected and high levels of gastrin, then it can be deduced that the sample was collected from the stomach. By way of example, if the capsule includes a motion detector and recorded back and forth movement, than that sample was collected from the duodenum where chyme is moved back and forth to mix with digestive juices. By way of example, if the collected gastrointestinal sample is green or brown in color, then it was likely collected in the proximal and ascending colon. In this manner, samples can be collected at various time points and in an a posteriori manner mapped to the most probable location of the GI tract where that sample was taken.

In some embodiments, one position identification parameter of the collected gastrointestinal sample is used to impute the sampling location in the GI tract.

In some embodiments, a combination of two or more position identification parameters of the collected gastrointestinal sample is used to impute the sampling location in the GI tract.

In some embodiments, a combination of three or more position identification parameters of the collected gastrointestinal sample is used to impute the sampling location in the GI tract.

In some embodiments, a combination of four or more position identification parameters of the collected gastrointestinal sample is used to impute the sampling location in the GI tract.

In some embodiments, the imputed sampling location in the GI tract is expressed as a probability with a confidence interval.

In some embodiments, device 10 has a detector to detect one or more of the position identification parameters listed in Table 4 in real time when in the GI tract.

In some embodiments, device 10 takes action based on the detection of one or more of the position identification parameters listed in Table 4 in real time when in the GI tract.

TABLE 4

Examples of position identification parameters that can be used a posteriori to impute the probabilistic location of a collected gastrointestinal sample. Ref on gas content: Nature Electronics, Vol 1, January 2018, 79-87.

| Imputed sampling location in the GI tract | pH | Color | Total bacteria per gram of fluid sample | Aerobes and facultative anaerobes per gram of fluid sample | Anaerobes per gram of fluid sample | Dissolved or free gas content | Other markers |
|---|---|---|---|---|---|---|---|
| Stomach | 1.5-3.5 | Clear or pink | $0$-$10^3$ | $0$-$10^3$ | 0 | Oxygen | gastrin |
| Jejunum | 6.1-7.1 | Yellow | $0$-$10^4$ | $0$-$10^4$ | 0 | | cholecystokinin, sectretin, gastric inhibitory polypeptide, motilin |
| Ileum | 7.0-8.0 | Yellow to light green | $10^4$-$10^8$ | $10^4$-$10^5$ | $10^3$-$10^8$ | | cholecystokinin, sectretin |

TABLE 4-continued

Examples of position identification parameters that can be used a posteriori to impute the probabilistic location of a collected gastrointestinal sample. Ref on gas content: Nature Electronics, Vol 1, January 2018, 79-87.

| Imputed sampling location in the GI tract | pH | Color | Total bacteria per gram of fluid sample | Aerobes and facultative anaerobes per gram of fluid sample | Anaerobes per gram of fluid sample | Dissolved or free gas content | Other markers |
|---|---|---|---|---|---|---|---|
| Proximal colon | 5.8-7.0 | Dark green to light brown | $10^{10}$-$10^{12}$ | $10^{2}$-$10^{9}$ | $10^{10}$-$10^{12}$ | High levels of carbon dioxide and hydrogen. Presence of pockets of free gas (not just bubbles) | carbohydrate enzymatic activity |
| Distal colon | 6.3-7.7 | Light brown to dark brown | $10^{10}$-$10^{12}$ | $10^{2}$-$10^{9}$ | $10^{10}$-$10^{12}$ | Medium levels of carbon dioxide and hydrogen | carbohydrate enzymatic activity |

In some embodiments, device 10 contains within it a camera and power source, together with on-board image storage capabilities or wireless transmission capabilities to an external image storage device.

In some embodiments, device 10 is connected via a short tether to a separate imaging capsule (for example the Medtronic Capsule Endoscopy System, Medtronic Inc. Minneapolis, Minn., USA) and the imaging capsule and device 10 are swallowed together and move together through the GI tract.

The visual images taken by the camera are time stamped. The start time and rate of sampling of device 10 is also known. Therefore, in both embodiments with the camera above, sampling locations in the GI tract are correlated to visual images taken by the camera by aligning the data from both onto a common timeline. Alternatively, the imaging capsule images the act of sampling by device 10, allowing direct visualization and confirmation of the GI region being sampled. Areas of visual interest can be further studied by analyzing the collected samples from that location. Likewise, interesting gastrointestinal samples can be further studied by analyzing the visual images taken from that location.

In some embodiments, the imaging system on board the sample collection device 10, or the imaging system in the dedicated imaging capsule tethered to device 10, communicates with device 10 and triggers a sample collection event when certain features are noted in the image. Examples of such features comprise bleeding mucosa, signs of inflammation, anatomical landmarks, and the like. In this manner, gastrointestinal samples are collected in specific regions of interest in the GI tract.

In some embodiments, the color of the gastrointestinal sample as collected by device 10 is used to identify the region of the GI tract that the sample was collected from. Using a color analysis obtained via capsule endoscopy (Medtronic Capsule Endoscopy System, Medtronic Inc. Minneapolis, Minn., USA), the present inventor discovered that clear samples are associated with the stomach, yellow tinted samples are associated with the bile acids present in the proximal portion of the small intestine, light green tinted samples are associated with the distal small intestines, dark green or light brown tinted samples are associated with the proximal or ascending colon, and dark brown tinted samples are associated with the fecal matter present in the distal colon. In the traditional use of capsule endoscopy, the patient is advised not to eat or drink, and in some cases prepare the colon for endoscopy before the endoscopy procedure, such that the lumen of the GU tract is empty of all ingested matter. In contrast, the present inventor created capsule endoscopy images take before, during and after ingestion of food, thereby discovering the nature and color of the ingested food along with the associated microbiota, as well as the dynamics of the GI tract at all phases of digestion and at all regions of the GI tract. By way of example, it has not been previously known that the content of the ascending colon, together with its associated microbiota, is in the range of light green to light brown in color until discovered in the manner above.

The colors visible at the outer surface of device 10 are generally red, pink or yellow when device 10 is traversing the GI tract that is devoid of digested food. In contrast, there is almost always digesting food and high levels of microbiota present in the distal small intestines and the proximal or ascending colon just distal to the ileocecal valve, where digestion processes occur over the course of many hours after the ingestion of a meal. The inventor has discovered that the colors visible at the outer surface of device 10 in the distal small intestines and proximal or ascending color are generally green and brown in color. In another embodiment, device 10 comprises a light source such as a light emitting diode that emits white light and one or more photodetectors that have in front of them filters selective for red and green wavelengths.

In some embodiments, device 10 comprises both a green and red light source and one or more photodetectors that separately measure the intensity of the reflected red or green light source.

In some embodiments, a portion of body 12 is optically clear and indented or invaginated so that the liquid contents of the GI tract collect therein. The color of this collected fluid is measured by any of the reflectance techniques described above. Without the indented or invaginated window, the tissue of the GI tract, which is pink in color, presses up against body 12, and the color of the luminal contents of the GI tract is not apparent or measurable. The indented or invaginated window is sufficiently shallow to allow for continuous exchange of the surrounding fluids as the capsule moves through the GI tract without enabling the tissue of the GI tract to touch the deepest portion of the indented or invaginated window.

In some embodiments, the indented or invaginated window as described above is illuminated from one side of the window and the transmitted light is measured from the other side. In this manner, the light crosses a defined length of fluid from the GI tract before being measured by a sensor.

The location of device 10 in the GI tract can be deduced by the absolute intensity and/or the ratio of the red and green reflected light as measured at the surface of the device. Sampling events can then be initiated based on the color of the medium surrounding the device. By way of example, when the absolute levels of green and red reflected light are both low, then device 10 is most likely in the stomach where there is not always intimate contact between the stomach wall and the device. When the intensity of the red reflected light is slightly higher than the green reflected light, device 10 is most likely in the small intestines. When sufficient green tint is detected relative to the red tint of reflected light, device 10 is most likely in the green or brown-colored luminal contents of the proximal or ascending colon. A gastrointestinal sample collection process can be initiated by device 10 at any one or combination of these locations based on preset thresholds, or based on a pattern of ratios or absolute intensities of green and red color reflections as measured by the device.

In some embodiments, device 10 comprises a pressure sensor that records the pressure exerted by the GI tract on device 10 in a time stamped manner A record of pressure is used to identify anatomical landmark areas of high radial or squeeze pressure on device 10, comprising passage of device 10 through the upper esophagus sphincter, the lower esophageal sphincter, the pyloric sphincter, the ileocecal valve, and the anus. A pattern of these pressure events is used to associate the collected gastrointestinal samples to specific regions of the GI tract. For example, in the subsequent hour or so after swallowing the device, a high radial pressure event indicates passage of device 10 through the pyloric sphincter between the stomach and the duodenum. A subsequent high radial pressure followed immediately by a low pressure event indicates passage of device 10 through the ileocecal sphincter between the narrow small intestines and the more cavernous proximal or ascending colon. A gastrointestinal sample collection process can be initiated by device 10 at any one or combination of these locations based on preset thresholds of radial pressure readings, or based on a pattern of pressure readings as measured by one or more pressure sensors on device 10.

Lumen-clearing peristaltic contractions are used by the GI tract to push along large un-digestible objects. During these contractions, there is relatively high squeeze pressure around device 10, with close contact between device 10 and the lumen of the GI tract. In another embodiment, elevated squeeze pressures are used to trigger sample collection events by device 10. In this manner, samples are obtained from the mucosal surfaces directly, versus from the bulk fluid surrounding device 10 at times when the GI tract is not squeezing device 10. The bulk fluid in the GI tract normally comprises mainly digestive fluids and food particles, which are different from the cells and molecules on or in the GI mucosal layer itself. Capturing samples from the mucosal layer directly during a peristaltic squeeze event, therefore, has the advantage of enriching the sample for microbes and host cells, along with the related intercellular molecules in, and adjacent to, the mucosal surfaces.

In some embodiments, the electrical impedance or resistance between two or more electrodes physically segregated on the surface of device 10 can be used to determine the location of device 10 within the GI tract. By way of example, the small intestines tend to squeeze device 10 nearly continuously which will lower the impedance or resistance of electricity between the electrodes. Alternatively, the stomach and the colon are larger organs and as such do not routinely come into intimate contact with all surfaces of device 10, thereby leading to increased impedance or resistance of electricity between the electrodes. A gastrointestinal sample collection process can be initiated by device 10 at any one or combination of these locations based on preset thresholds of impedances, or based on a pattern of impedance readings as measured by electrodes on the device.

In some embodiments, device 10 comprises an accelerometer or other triangulation tracking sensor that detects and records the motion of device 10 in the GI tract in a time stamped manner. Optionally, a second accelerometer can be worn outside GI tract of the user to negate gross body movements of the user and only look at relative movement of device 10 within the body. By way of example, the external accelerometer can be in a smart phone device carried by the user. By doing so, transit times and a virtual path of device 10 through the GI tract can be reconstructed to associate the collected gastrointestinal samples to specific regions of the GI tract.

In some embodiments, device 10 comprises a sensor that activates when moisture is detected in collecting member 18, indicating the collection of a gastrointestinal sample. Activation of the moisture sensor triggers an identification element such as an active radio frequency identification (RFID) chip to indicate the time or position of device 10 at the initiation of sample collection.

In some embodiments, the rate of exposure of collecting member 18 to the GI tract is not uniform. Sampling occurs at different rates in different parts of the GI tract based on the expected or measured transit time of device 10 through the GI tract. For example, the sampling rate is at least two times faster than normal in the mouth and esophagus where transit is fastest, normal in the stomach and small intestine where transit time slows, and half the normal rate or less in the colon where transit time is slowest. In this manner, the sampling rate can vary by a factor of 4 or more to achieve more uniform sampling of device 10 per distance of GI tract covered.

In some embodiments, device 10 contains a radio-opaque marker to make the capsule visible in x-rays or fluoroscopy.

In some embodiments, device 10 comprises a radio frequency ID (RFID) chip to make the capsule detectable with an external reader.

In some embodiments, device 10 comprises a bar code readable by an external reader.

In some embodiments, sample collection is initiated by exposing collecting member 18 to fluid communication with the GI tract using an actuator driven by a potential or chemical energy power source in device 10. At the end of the sample collection process, sealing of collecting member 18 is accomplished via an actuator driven by a second potential or chemical energy power source in device 10. By way of example, the collecting member is movable or the opening 42 openable by a spring or elastic member, which in turn is restrained from expanding by a fuse wire. At the time of sample collection, the fuse wire is burned by an electric current and the spring or elastic element expands in order to expose collecting member 18 to the GI tract. At the end of the sampling window, collecting member 18 is moveable into a sealed position or the opening 42 is sealed by a second spring or elastic element which is also restrained by a fuse. At the end of sample collection, this second fuse is burned by an electrical current and the second spring or elastic element expands in order to seal the collecting member from further exposure to the GI tract.

In some embodiments, a valve blocks opening 42. At the desired time of sampling, an electrical signal or resistive heating element opens the valve and gastrointestinal samples 40 flow through opening 42 into an elastically collapsed or under-pressured collecting member 18 via one way valve 24. In this manner, only a single signal is required to initiate sample collection and isolate gastrointestinal samples inside collecting member 18.

In some embodiments, the valve is a membrane that blocks opening 42 and the resistive heating element destroys the membrane. In some embodiments, the membrane blocking opening 42 comprises a metal.

In some embodiments, the membrane blocking opening 42 comprises a polymer.

In some embodiments, the membrane blocking opening 42 comprises a resistive heater.

In some embodiments, the membrane blocking opening 42 comprises poly(L-lactic acid) or poly(lactide-co-glycolide).

In some embodiments, the valve blocking opening 42 comprises a material that changes phases from solid to liquid upon heating. Examples of such materials comprise polyethylene glycol, paraffin and other waxes. The material undergoes a change of volume due to the phase change that is utilized as a linear displacement to open a normally closed valve to enable sampling of gastrointestinal samples in a time window of 1 minute to 1 hour before re-sealing the valve when the electrical current is stopped.

In some embodiments, the membrane blocking opening 42 is burst due to high pressure generated by a gas.

In some embodiments, a flexible tube connecting opening 42 to collecting member 18 is pinched closed by a spring element.

In some embodiments, a flexible tube connecting opening 42 to collecting member 18 is kinked in order to close and seal the tube.

In some embodiments, opening 42 is controlled by a bi-stable or flip-flop valve that requires no energy to be in an open or closed configuration, but rather only consumes energy in transitioning between the open and closed states.

In some embodiments, device 10 comprises an electrical or chemical power source that causes a phase change in a material that subsequently enables or triggers sample collection.

In some embodiments, device 10 is placed in capsule 72 comprising covering element 30 that targets device 10 to be exposed to the GI tract fluids in the region of the duodenum where the pH is around 5-6. When device 10 is exposed for the first time to GI tract fluids in the duodenum, a moisture sensitive switch is activated that starts a timing circuit that triggers sampling events at set time points to sample specific sampling regions of the small intestine and colon based on known transit times through these regions. In this manner, a pH range is used for initial delivery of device 10 to the intestines and then thereafter an electronic timing circuit triggers the sampling in a pH independent manner.

In some embodiments, device 10 counts the number of peristaltic pressure waves of the GI tract that act on device 10 via a sensor. Device 10 uses the number of peristaltic pressure waves to estimate the distance device 10 has moved through the GI tract as a sort of "odometer". Device 10 uses the number of peristaltic pressure waves to guide the sampling activity or release profile of an active agent.

Device 10 becomes embedded in stool while in the colon. At the time of defecation, device 10 may be completely embedded inside stool that has the consistency of clay. It is necessary to recover device 10 and extract the gastrointestinal sample therein for further analysis in the easiest and most user-friendly manner possible.

In some embodiments, a toilet collection device comprises slots with a width just slightly smaller than the diameter of device 10 and a length at least as long as the overall length of device 10. Slots are more efficient than holes in letting through the stool and retaining device 10.

In some embodiments, a toilet collection device comprises a rotatable mechanical disrupter, such as an impeller, paddle wheel or whisk, which is positioned beneath the water level of the toilet bowl and rotates to mechanically break up the stool through a passageway. The flushing of the toilet creates a flow of water that helps moves the stool through the mechanical disrupter and the passageway, leaving behind just device 10.

In some embodiments, a collection kit comprises an axial element with radially protruding elements that when spun around the axial axis breaks up the stool and snares device 10. This retrieval device is particularly suited for capturing device 10 when in the form of an elongated tube. The axial element can be retracted with the collected device 10 into a sheath for hygienic transfer of device 10 from the toilet to a secondary collection container.

In some embodiments, a kit is provided comprising device 10 and any of the collection devices described above.

In some embodiments, device 10 is used as a delivery device. Device 10 is pre-loaded with an active agent outside the body before being swallowed. The portion of collecting member 18 that is exposed to the gastrointestinal fluids releases the active agent into the GI tract. By controlling the time, duration and rate of exposure of collecting member 18 to the GI tract, it is possible to control the rate and location of dispensing of the active agent.

In some embodiments, device 10 serves a dual purpose of being a delivery device that releases an active agent in the GI tract, while simultaneously collecting gastrointestinal samples. Device 10 can therefore analyze the effect of the active agent being dispensed.

Additional objects, advantages, and novel features of the present invention will become apparent to one ordinarily skilled in the art upon examination of the following examples, which are not intended to be limiting. Additionally, each of the various embodiments and aspects of the present invention as delineated hereinabove and as claimed in the claims section below finds experimental support in the following examples.

EXAMPLES

Reference is now made to the following examples, which together with the above disclosure, illustrate the invention in a non-limiting fashion.

Example 1. Long Tube-Shaped Collecting Member

There is a concern that any indigestible device might be retained in a patient's GI tract. The larger the diameter of device, the more likely the device is to be retained. Therefore, there is a safety advantage in reducing the diameter of the sampling device to the minimum possible, while still collecting the maximal volume of sample.

In this example, a 50 cm long hollow tube of silicone rubber with an external diameter of 2.0 mm and an internal diameter of 1.5 mm was used as body and the inner lumen formed the collecting member. This tube, when unfolded, is highly unlikely to be retained by the GI tract. A glass capsule micro-RFID tag that serves to both identify the device and also as a radio opaque marker was inserted into one end of the tube which was then sealed with silicone glue. Starting with the sealed end, the tube was coiled around itself tightly enough to collapse the lumen, thereby removing almost all of the gas therein, while at the same time being embedded in a water soluble adhesive that kept the tube from unraveling once the adhesive was dry. The coiled tube, with the dry adhesive keeping it in the shape of a tight coil, was placed inside a size 00 HPMC capsule. The capsule was covered with an enteric coating as the covering element, forming the finished device.

The device capsule was swallowed. The enteric coating kept the body intact until the device was in the proximal small intestines, at which point the enteric covering element and external capsule dissolved. The adhesive holding the coiled tube-shaped body started to dissolve, and the body started to uncoil due to the inherent elasticity and low hysteresis of silicone, and thereby draw in gastrointestinal samples into the sampling opening of the tube which was on the outer most layer of the coil. As the adhesive continued to degrade due to moisture in the GI tract, the tube uncoiled more, drawing in more gastrointestinal sample into the tube. The tube passed into the right colon where it continued to uncoil and collect gastrointestinal samples. Overall sampling time was approximately 6 hours until the adhesive completely degraded and the tube shaped body was completely uncoiled, and the sampling process complete.

The device passed in the stool the next day and was collected from the toilet using a rotating hooked retrieval wand. The collected gastrointestinal samples formed a linear array inside the 50 cm long tube, with the small intestine samples closest to the sealed end of the tube and the colonic sample closer to the open end of the tube. 455 microliters of gastrointestinal samples were recovered from the tube and analyzed. The recovered samples had a pH of 5.5 towards the closed end of the tube, representing the proximal small intestine, rising to a pH of 8 towards the middle of the tube representing the jejunum and ileum, and ending with pH of 6 towards the open end of the tube, representing samples taken from the ascending colon. Relative to the 900 microliter volume of the ingested HPMC size 00 capsule, the collected volume percentage was 455 microliters/900 microliters, or 51%.

The device as described in this example is highly unlikely to be retained in the GI tract of a patient, since all of the components of device dissolve in the GI tract within several hours, with the exception of a 50 cm long silicone tube that is only 2 mm in diameter with a maximal cross sectional area of only 3.1 square millimeters. Such a long and slender tube does not have sufficient size or cross sectional area to block any part of the human GI tract for a patient who is asymptomatic of a pre-existing intestinal stricture.

Example 2. Segmented Collecting Member

In this example, a segmented closed-ended tube-shaped body was made from silicone with a duck-bill one-way valve at the sampling opening as illustrated in FIG. 34. The body is 5 mm in outer diameter and 65 mm long. The collecting member is divided into 4 segments, each approximately 13 mm long, separated by narrow portions 2.2 mm in outer diameter to enable axial flexure of the device while moving through the highly-curved small intestine. The thickness of the body walls is 0.3 mm and made of shore 70 silicone so that the maximal outward radial pressure exerted by expanding tube-shaped body is about 50 grams-force per cm length of tube-shaped body. The collecting member was radially collapsed to minimize the lumen volume and wound in a spiral fashion with axial offset about a central axis as illustrated in FIG. 36 and packaged inside a size 2 HPMC capsule.

Five devices were prepared in an identical manner except for the enteric coatings applied to the outside surface of the HPMC capsule of each, as specified in Table 5 below. Once the covering element dissolves, the body expands in approximately 1 minute to sample only one specific region of the GI tract.

TABLE 5

Coating of five sampling devices

| Device number | Target pH of enteric coating (covering element) | Target region | pH of recovered samples |
|---|---|---|---|
| 1 | None | Stomach | 1.8 |
| 2 | pH 5.5 | Duodenum | 5.8 |
| 3 | pH 6.5 | Jejunum | 6.9 |
| 4 | pH 7.5 | Ileum | 8.0 |
| 5 | pH >6.5 over pH <6.5 ("inverse pH coating") | Ascending colon | 6.7 |

A subject swallowed the five devices comprising the segmented collecting member. After recovery from the stool of the subject the next day, the devices contained approximately 1 ml of gastrointestinal samples each, which resulted in a collection volume percentage of 277% relative to the 0.36 ml volume of the size 2 capsule that contained the device at the time of swallowing. The recovered samples had pH levels as per Table 5 above. The pH of the samples was used as a position identification parameter to verify the location of sampling as per Table 4.

A gas chromatography-mass spectrometric analysis was conducted on the recovered samples and a representative sample of 30 metabolites out of the 657 metabolites that were positively identified and quantified is shown in Table 6 below. The higher the number, the more of that specific metabolite is present in that region of the GI tract. The variability of absolute numbers of each metabolite across the columns informs us as to the biochemical and physiological functions occurring in that region of the GI tract. This demonstrates the importance of tightly controlling the location of sampling in the different regions of the GI tract, versus simply measuring at a single point or profiling the metabolites in the stool. The metabolites with only a number as their identifier are uncharacterized metabolites, which demonstrates the ability of the present invention to identify novel metabolites and profile their presence in the different regions of the GI tract.

TABLE 6

Metabolites found in the different regions of the GI tract using the sampling device of Example 2.

| Metabolite | Stomach | Duodenum | Jejunum | Ileum | Ascending colon |
|---|---|---|---|---|---|
| Urea | 300,659 | 393,582 | 300,122 | 5,147 | 422,339 |
| Hydroxylamine | 95,562 | 257,776 | 197,103 | 173,725 | 126,381 |
| 209175 | 252,852 | 220,380 | 239,197 | 220,437 | 241,682 |
| Valine | 889,576 | 130,076 | 307,284 | 139,980 | 171,653 |
| Isoleucine | 589,914 | 122,106 | 208,208 | 124,524 | 176,824 |
| Alanine | 774,812 | 113,268 | 247,677 | 138,271 | 158,737 |
| Oxoproline | 339,857 | 100,258 | 136,278 | 35,704 | 76,562 |
| Serine | 399,685 | 98,964 | 32,943 | 61,435 | 57,736 |
| Leucine | 995,892 | 90,992 | 330,123 | 104,143 | 269,620 |
| Tyrosine | 533,684 | 90,914 | 120,659 | 125,259 | 137,611 |
| Glycine | 576,710 | 84,336 | 761,457 | 42,345 | 61,797 |
| Stearic acid | 74,727 | 75,973 | 98,124 | 70,426 | 303,496 |
| Butanoic acid | 13,504 | 73,886 | 24,125 | 1,591 | 3,193 |
| Glycerol | 533,347 | 69,212 | 282,590 | 56,275 | 1,424,295 |
| 137 | 68,306 | 62,245 | 68,693 | 65,887 | 64,366 |
| Proline | 527,366 | 58,763 | 100,072 | 60,047 | 69,112 |
| Phenylalanine | 297,498 | 54,945 | 80,107 | 70,563 | 77,771 |
| Hexuronic acid | 156,779 | 48,840 | 83,768 | 911 | 50,835 |
| Uric acid | 75,040 | 48,487 | 14,345 | 574 | 17,497 |
| 120562 | 37,784 | 40,918 | 48,675 | 32,659 | 12,970 |
| 107077 | 37,784 | 40,918 | 43,483 | 38,261 | 16,187 |
| 209688 | 33,755 | 40,918 | 48,675 | 38,261 | 16,187 |
| Aspartic acid | 242,003 | 39,222 | 76,749 | 57,326 | 33,190 |
| 479 | 37,784 | 34,996 | 48,675 | 38,261 | 16,187 |
| 3228 | 40,755 | 28,749 | 32,208 | 69,490 | 31,987 |
| Galactinol | 1,046 | 25,008 | 3,381 | 1,092 | 26,618 |
| Threonine | 201,986 | 24,770 | 15,521 | 13,671 | 23,229 |
| 321061 | 19,642 | 23,832 | 7,051 | 7,782 | 6,183 |
| Galactose | 5,196 | 22,778 | 11,248 | 31,515 | 540,089 |
| Cholesterol | 49,545 | 22,316 | 36,689 | 21,710 | 83,790 |

When a feature or element is herein referred to as being "on" another feature or element, it can be directly on the other feature or element or intervening features and/or elements may also be present. In contrast, when a feature or element is referred to as being "directly on" another feature or element, there are no intervening features or elements present. It will also be understood that, when a feature or element is referred to as being "connected", "attached" or "coupled" to another feature or element, it can be directly connected, attached or coupled to the other feature or element or intervening features or elements may be present. In contrast, when a feature or element is referred to as being "directly connected", "directly attached" or "directly coupled" to another feature or element, there are no intervening features or elements present. Although described or shown with respect to one embodiment, the features and elements so described or shown can apply to other embodiments. It will also be appreciated by those of skill in the art that references to a structure or feature that is disposed "adjacent" another feature may have portions that overlap or underlie the adjacent feature.

Terminology used herein is for the purpose of describing particular embodiments only and is not intended to be limiting of the invention. For example, as used herein, the singular forms "a", "an" and "the" are intended to include the plural forms as well, unless the context clearly indicates otherwise. It will be further understood that the terms "comprises" and/or "comprising," when used in this specification, specify the presence of stated features, steps, operations, elements, and/or components, but do not preclude the presence or addition of one or more other features, steps, operations, elements, components, and/or groups thereof. As used herein, the term "and/or" includes any and all combinations of one or more of the associated listed items and may be abbreviated as "/".

Spatially relative terms, such as "under", "below", "lower", "over", "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if a device in the figures is inverted, elements described as "under" or "beneath" other elements or features would then be oriented "over" the other elements or features. Thus, the exemplary term "under" can encompass both an orientation of over and under. The device may be otherwise oriented (rotated 90 degrees or at other orientations) and the spatially relative descriptors used herein interpreted accordingly. Similarly, the terms "upwardly", "downwardly", "vertical", "horizontal" and the like are used herein for the purpose of explanation only unless specifically indicated otherwise.

Although the terms "first" and "second" may be used herein to describe various features/elements (including steps), these features/elements should not be limited by these terms, unless the context indicates otherwise. These terms may be used to distinguish one feature/element from another feature/element. Thus, a first feature/element discussed below could be termed a second feature/element, and similarly, a second feature/element discussed below could be termed a first feature/element without departing from the teachings of the present invention.

Throughout this specification and the claims which follow, unless the context requires otherwise, the word "comprise", and variations such as "comprises" and "comprising" means various components can be co-jointly employed in the methods and articles (e.g., compositions and apparatuses including device and methods). For example, the term "comprising" will be understood to imply the inclusion of any stated elements or steps but not the exclusion of any other elements or steps.

As used herein in the specification and claims, including as used in the examples and unless otherwise expressly specified, all numbers may be read as if prefaced by the word "about" or "approximately," even if the term does not expressly appear. The phrase "about" or "approximately" may be used when describing magnitude and/or position to indicate that the value and/or position described is within a reasonable expected range of values and/or positions. For example, a numeric value may have a value that is +/−0.1% of the stated value (or range of values), +/−1% of the stated value (or range of values), +/−2% of the stated value (or range of values), +/−5% of the stated value (or range of values), +/−10% of the stated value (or range of values), etc. Any numerical values given herein should also be understood to include about or approximately that value, unless the context indicates otherwise. For example, if the value "10" is disclosed, then "about 10" is also disclosed. Any numerical range recited herein is intended to include all sub-ranges subsumed therein. It is also understood that when a value is disclosed that "less than or equal to" the value, "greater than or equal to the value" and possible ranges between values are also disclosed, as appropriately understood by the skilled artisan. For example, if the value "X" is disclosed the "less than or equal to X" as well as "greater than or equal to X" (e.g., where X is a numerical value) is also disclosed. It is also understood that the throughout the application, data is provided in a number of different formats, and that this data, represents endpoints and starting points, and ranges for any combination of the data points. For example, if a particular data point "10" and a particular data point "15" are disclosed, it is understood that greater than, greater than or equal to, less than, less than or equal to, and equal to 10 and 15 are considered disclosed as well as between 10 and 15. It is also understood that each unit between two particular units are also disclosed. For example, if 10 and 15 are disclosed, then 11, 12, 13, and 14 are also disclosed.

Although various illustrative embodiments are described above, any of a number of changes may be made to various embodiments without departing from the scope of the invention as described by the claims. For example, the order in which various described method steps are performed may often be changed in alternative embodiments, and in other alternative embodiments one or more method steps may be skipped altogether. Optional features of various device and system embodiments may be included in some embodiments and not in others. Therefore, the foregoing description is provided primarily for exemplary purposes and should not be interpreted to limit the scope of the invention as it is set forth in the claims.

The examples and illustrations included herein show, by way of illustration and not of limitation, specific embodiments in which the subject matter may be practiced. As mentioned, other embodiments may be utilized and derived there from, such that structural and logical substitutions and changes may be made without departing from the scope of this disclosure. Such embodiments of the inventive subject matter may be referred to herein individually or collectively by the term "invention" merely for convenience and without intending to voluntarily limit the scope of this application to any single invention or inventive concept, if more than one is, in fact, disclosed. Thus, although specific embodiments have been illustrated and described herein, any arrangement calculated to achieve the same purpose may be substituted for the specific embodiments shown. This disclosure is intended to cover any and all adaptations or variations of various embodiments. Combinations of the above embodiments, and other embodiments not specifically described herein, will be apparent to those of skill in the art upon reviewing the above description.

I claim:

1. A device for collecting gastrointestinal samples, the device comprising:
    a collapsed tube-shaped body with one closed end and one open end, wherein said collapsed state is formed by winding or folding said tube-shaped body, and
    an element configured to degrade over time to allow said collapsed tube-shaped body to gradually expand and collect a series of gastrointestinal samples through said open end from more than one region of a gastrointestinal tract, the degradation over time prevents the collapsed tube-shaped body from expanding all at once,
    wherein said tube-shaped body is coiled around an axis into one or more layers,
    wherein the one or more layers comprises an outer layer covered by an outer portion of the element and an inner layer covered by an inner portion of the element, and
    wherein degradation of the outer portion of the element and the inner portion of the element is controlled so that the outer layer is free to expand before the inner layer.

2. The device of claim 1, wherein a ratio of a length to a diameter of said tube-shaped body when fully expanded is 5 or greater.

3. The device of claim 1, wherein said tube-shaped body expands from said collapsed state in a radial direction with a length of said tube-shaped body remaining constant.

4. The device of claim 1, wherein a rate of expansion of said tube-shaped body is controlled by the rate of degradation of said element.

5. The device of claim 1, wherein a rate of expansion of said tube-shaped body is controlled by a size of said open end.

6. The device of claim 1, wherein said element includes time-dependent moisture degradable material and said tube-shaped body is covered by an acid resistant material.

7. The device of claim 1, wherein gastrointestinal samples are collected as a linear array within said tube-shaped body.

8. The device of claim 1, wherein the more than one region of the gastrointestinal tract are selected from a stomach, a duodenum, a jejunum, an ileum, an ascending colon, a transverse colon, and a descending colon.

9. The device of claim 1, wherein the device is autonomous and configured to be swallowed and recovered from stool.

10. The device of claim 1, wherein the collapsed tube-shaped body gradually expands for a time period of about 1 hour to 8 hours to collect the series of gastrointestinal samples.

* * * * *